(12) United States Patent
Mandelboim et al.

(10) Patent No.: US 12,077,583 B2
(45) Date of Patent: Sep. 3, 2024

(54) ANTIBODIES SPECIFIC TO HUMAN NECTIN4

(71) Applicants: YISSUM RESEARCH DEVELOPMENT COMPANY OF THE HEBREW UNIVERSITY OF JERUSALEM LTD., Jerusalem (IL); NECTIN THERAPEUTICS LTD., Jerusalem (IL)

(72) Inventors: Ofer Mandelboim, Shoham (IL); Adi Reches, Koranit (IL); Stipan Jonjic, Rijeka (HR); Pinchas Tsukerman, Jerusalem (IL)

(73) Assignees: NECTIN THERAPEUTICS LTD., Jerusalem (IL); YISSUM RESEARCH DEVELOPMENT COMPANY OF THE HEBREW, Jerusalem (IL)

( * ) Notice: Subject to any disclaimer, the term of this patent is extended or adjusted under 35 U.S.C. 154(b) by 906 days.

(21) Appl. No.: 17/052,960

(22) PCT Filed: May 6, 2019

(86) PCT No.: PCT/IL2019/050508
§ 371 (c)(1),
(2) Date: Nov. 4, 2020

(87) PCT Pub. No.: WO2019/215728
PCT Pub. Date: Nov. 14, 2019

(65) Prior Publication Data
US 2021/0130459 A1  May 6, 2021

Related U.S. Application Data

(60) Provisional application No. 62/668,824, filed on May 9, 2018.

(51) Int. Cl.
| | | |
|---|---|---|
| C07K 16/00 | (2006.01) | |
| A61K 45/06 | (2006.01) | |
| A61P 35/00 | (2006.01) | |
| C07K 16/28 | (2006.01) | |
| A61K 39/00 | (2006.01) | |

(52) U.S. Cl.
CPC .......... C07K 16/2803 (2013.01); A61K 45/06 (2013.01); A61P 35/00 (2018.01); *A61K 2039/505* (2013.01)

(58) Field of Classification Search
CPC .......... C07K 16/2803; C07K 2317/732; A61P 35/00; A61K 2039/505; A61K 39/0011; A61K 39/395
See application file for complete search history.

(56) References Cited

U.S. PATENT DOCUMENTS

| | | |
|---|---|---|
| 4,816,567 A | 3/1989 | Cabilly |
| 4,946,778 A | 8/1990 | Ladner |
| 5,225,539 A | 7/1993 | Winter |
| 5,530,101 A | 6/1996 | Queen |
| 5,585,089 A | 12/1996 | Queen |
| 5,641,870 A | 6/1997 | Rinderknecht |
| 5,693,761 A | 12/1997 | Queen |
| 5,693,762 A | 12/1997 | Queen |
| 2007/0041985 A1 | 2/2007 | Unger |
| 2009/0214517 A1 | 8/2009 | Wong |
| 2009/0215175 A1 | 8/2009 | Unger |
| 2014/0271635 A1 | 9/2014 | Brogdon |

FOREIGN PATENT DOCUMENTS

| | | |
|---|---|---|
| CN | 101663322 A | 3/2010 |
| EP | 0404097 A2 | 12/1990 |
| JP | 2016502554 A | 1/2016 |
| RU | 2258367 C2 | 8/2005 |
| WO | 8601533 A1 | 3/1986 |
| WO | 9007861 A1 | 7/1990 |
| WO | 9222653 A1 | 12/1992 |
| WO | 9311161 A1 | 6/1993 |
| WO | 9315210 A1 | 8/1993 |
| WO | 9613583 A2 | 5/1996 |
| WO | 9637621 A2 | 11/1996 |
| WO | 2016028656 A1 | 2/2016 |
| WO | 2016134333 A1 | 8/2016 |
| WO | 2017037707 A1 | 3/2017 |
| WO | 2017042210 A1 | 3/2017 |
| WO | WO2017042210 * | 3/2017 |
| WO | 2017149538 A1 | 9/2017 |
| WO | 2018158398 A1 | 9/2018 |
| WO | 2022056304 A1 | 3/2022 |

OTHER PUBLICATIONS

Campbell Dean et al Molecular Imaging and Biology 18: 768-775, 2016 (Year: 2016).*
Challita-Eid et al, Cancer Research 75: 3003-3013, 2016 (Year: 2016).*
Pavlova et al, elife Sciences Publication 2: e00358-1, 2013 (Year: 2013).*
Challita-Eid et al, Cancer Res 76 (10): 3003-3013 , 2016 (Year: 2016).*
Anderson et al., (2016) Lag-3, Tim-3, and TIGIT: Co-inhibitory Receptors with Specialized Functions in Immune Regulation. Immunity. 44(5): 989-1004.
Arnon et al., (2008) Harnessing soluble NK cell killer receptors for the generation of novel cancer immune therapy. PLoS One 3(5): e2150; 10 pages.

(Continued)

*Primary Examiner* — Lei Yao
(74) *Attorney, Agent, or Firm* — RAPHAEL BELLUM PLLC; Stephen C. Bellum

(57) ABSTRACT

The present invention provides monoclonal antibodies that recognize human Nectin4 with high affinity and specificity and inhibit its binding to T cell immunoreceptor with Ig and ITIM domains (TIGIT). The present invention further provides pharmaceutical compositions comprising the antibodies and methods for their use in cancer immunotherapy and in diagnosis.

13 Claims, 19 Drawing Sheets

Specification includes a Sequence Listing.

(56) References Cited

OTHER PUBLICATIONS

Bird et al., (1988) Single-chain antigen-binding proteins. Science 242(4877): 423-426.
Brennan et al., (1985) Preparation of bispecific antibodies by chemical recombination of monoclonal immunoglobulin G1 fragments. Science 229(4708): 81-83.
Campbell et al., (2016) Preclinical Evaluation of an Anti-Nectin-4 ImmunoPET Reagent in Tumor-Bearing Mice and Biodistribution Studies in Cynomolgus Monkeys. Mol Imaging Biol 18(5): 768-775.
Carter et al., (1992) High level Escherichia coli expression and production of a bivalent humanized antibody fragment. Biotechnology (N Y) 10(2): 163-167.
Challita-Eid et al., (2016) Enfortumab Vedotin Antibody-Drug Conjugate Targeting Nectin-4 Is a Highly Potent Therapeutic Agent in Multiple Preclinical Cancer Models. Cancer Res 76(10): 3003-3013.
Clackson et al., (1991) Making antibody fragments using phage display libraries. Nature 352(6336): 624-628.
Fabre-Lafay et al., (2007) Nectin-4 is a new histological and serological tumor associated marker for breast cancer. BMC Cancer 7: 73; 16 pages.
Fields et al., (2013) Creation of recombinant antigen-binding molecules derived from hybridomas secreting specific antibodies. Nat Protoc 8(6): 1125-1148.
Glasner et al., (2012) Elucidating the mechanisms of influenza virus recognition by Ncr1. PLoS One 7(5): e36837; 10 pages.
Glasner et al., (2015) Expression, Function, and Molecular Properties of the Killer Receptor Ncr1-Noé. J Immunol 195 (8): 3959-3969.
Gur et al., (2010) The activating receptor NKp46 is essential for the development of type 1 diabetes. Nat Immunol 11 (2): 121-128.
Gur et al., (2015) Binding of the Fap2 protein of Fusobacterium nucleatum to human inhibitory receptor TIGIT protects tumors from immune cell attack. Immunity 42(2): 344-355.
Hanna et al., (2006) Decidual NK cells regulate key developmental processes at the human fetal-maternal interface. Nat Med 12(9): 1065-1074.
Holliger et al., (1993) "Diabodies": small bivalent and bispecific antibody fragments. Proc Natl Acad Sci U S A 90(14): 6444-6448.
Houston et al., (2016) Pregnancy-specific glycoprotein expression in normal gastrointestinal tract and in tumors detected with novel monoclonal antibodies. MAbs 8(3): 491-500.
Huston et al., (1988) Protein engineering of antibody binding sites: recovery of specific activity in an anti-digoxin single-chain Fv analogue produced in Escherichia coli. Proc Natl Acad Sci U S A 85(16): 5879-5883.
June and Sadelain (2018) Chimeric Antigen Receptor Therapy. N Engl J Med 379(1): 64-73.
Kochenderfer et al., (2009) Construction and preclinical evaluation of an anti-CD19 chimeric antigen receptor. J Immunother. Author manuscript; available in PMC Sep. 1, 2010. Published in final edited form as: J Immunother. Sep. 2009; 32(7): 689-702.
Kohler and Milstein (1975) Continuous cultures of fused cells secreting antibody of predefined specificity. Nature 256 (5517): 495-497.
Ankry et al., (2010) Expression and function of CD300 in NK cells. J Immunol 185(5): 2877-2886.
Lankry et al., (2013) The interaction between CD300a and phosphatidylserine inhibits tumor cell killing by NK cells. Eur J Immunol 43(8): 2151-2161.
Lee et al., (2011) In vivo inhibition of human CD19-targeted effector T cells by natural T regulatory cells in a xenotransplant murine model of B cell malignancy. Cancer Res 71(8): 2871-2881.
Lefranc et al., (2003) IMGT unique numbering for immunoglobulin and T cell receptor variable domains and Ig superfamily V-like domains. Dev Comp Immunol 27(1): 55-77.

Mandelboim et al., (1996) Protection from lysis by natural killer cells of group 1 and 2 specificity is mediated by residue 80 in human histocompatibility leukocyte antigen C alleles and also occurs with empty major histocompatibility complex molecules. J Exp Med 184(3): 913-922.
Marks et al., (1991) By-passing immunization. Human antibodies from V-gene libraries displayed on phage. J Mol Biol 222(3): 581-597.
Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-117.
Morrison et al., (1984) Chimeric human antibody molecules: mouse antigen-binding domains with human constant region domains. Proc Natl Acad Sci U S A 81(21): 6851-6855.
Pavlova et al., (2013) A role for PVRL4-driven cell-cell interactions in tumorigenesis. Elife 2: e00358; 24 pages.
Scarano et al., (2010) Surface plasmon resonance imaging for affinity-based biosensors. Biosens Bioelectron 25(5): 957-966.
Siddharth et al., (2017) Nectin-4 is a breast cancer stem cell marker that induces WNT/β-catenin signaling via Pi3k/Akt axis. Accepted Manuscript. International Journal of Biochemistry and Cell Biology http://dx.doi.org/10.1016/j.biocel.2017.06.007. 33 pages.
Stanietsky et al., (2009) The interaction of TIGIT with PVR and PVRL2 inhibits human NK cell cytotoxicity. Proc Natl Acad Sci U S A 106(42): 17858-17863.
Stanietsky et al., (2013) Mouse TIGIT inhibits NK-cell cytotoxicity upon interaction with PVR. Eur J Immunol 43(8): 2138-2150.
Tsukerman et al., (2014) Expansion of CD16 positive and negative human NK cells in response to tumor stimulation. Eur J Immunol 44(5): 1517-1525.
Ward et al., (1989) Binding activities of a repertoire of single immunoglobulin variable domains secreted from Escherichia coli. Nature 341(6242): 544-546.
Wienken et al., (2010) Protein-binding assays in biological liquids using microscale thermophoresis. Nat Commun 1: 100; 7 pages.
Wu and Kabat (1970) An analysis of the sequences of the variable regions of Bence Jones proteins and myeloma light chains and their implications for antibody complementarity. J Exp Med 132(2): 211-250.
Yossef et al., (2015) Targeting natural killer cell reactivity by employing antibody to NKp46: implications for type 1 diabetes. PLoS One 10(2): e0118936; 15 pages.
Zapata et al., (1995) Engineering linear F(ab')2 fragments for efficient production in Escherichia coli and enhanced antiproliferative activity. Protein Eng 8(10): 1057-1062.
Zdravkovic et al., (1999) Susceptibility of MHC class I expressing extravillous trophoblast cell lines to killing by natural killer cells. Placenta 20(5-6): 431-440.
Zhu et al., (2016) Identification of CD112R as a novel checkpoint for human T cells. J Exp Med 213(2): 167-176.
Rudikoff et al., (1982) Single amino acid substitution altering antigen-binding specificity. Proc Natl Acad Sci U S A 79(6): 1979-1983.
Badri et al., (2016) Optimization of radiation dosing schedules for proneural glioblastoma. J Math Biol 72(5): 1301-1336. Abstract.
Baylot et al., (2017) TCTP Has a Crucial Role in the Different Stages of Prostate Cancer Malignant Progression. Results Probl Cell Differ 64: 255-261. Abstract.
Beisenayeva (2015) Role of immunohistochemical cancer research, Department of Oncology of Karaganda State Medical University. Medicine and Ecology 2(75): 12-17. With machine translated abstract.
Yin Dongdong et al., (2016) Prokaryotic expression of Nectin-4 gene and preparation of polyclonal antibodies. Journal of Yangzhou University 37(3): 6-10. Machine translated abstract.

* cited by examiner

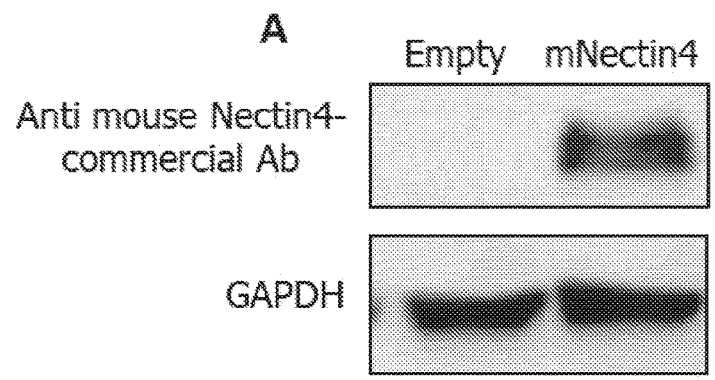
FIGURE 5A
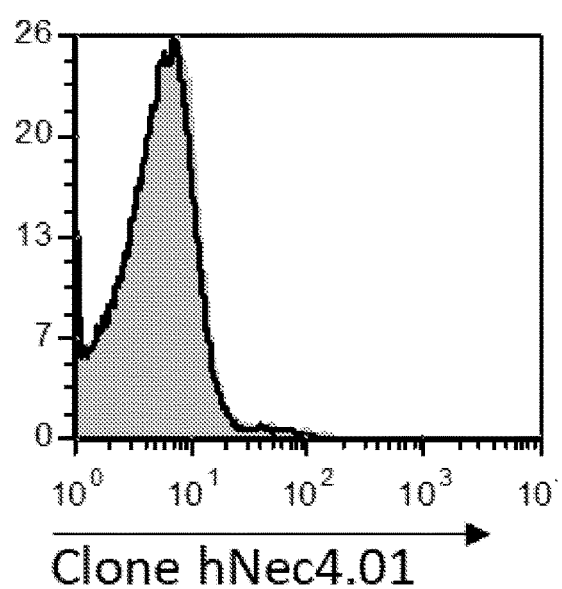 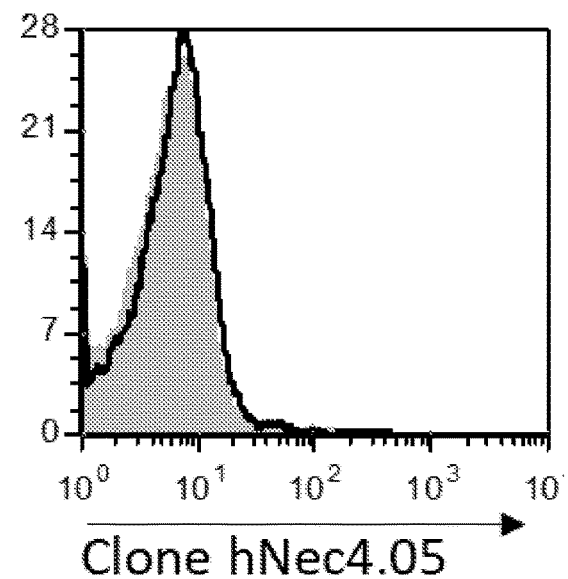
FIGURE 5B					FIGURE 5C

ANTIBODIES SPECIFIC TO HUMAN NECTIN4

FIELD OF THE INVENTION

The invention is in the field of immunotherapy and relates to antibodies and fragments thereof which bind to the human protein Nectin4, to polynucleotide sequences encoding these antibodies and to cells producing these antibodies. The invention further relates to therapeutic and diagnostic compositions comprising these antibodies and to methods of treating and diagnosing diseases, particularly cancer, using these antibodies.

BACKGROUND OF THE INVENTION

Immunotherapy is one of the most promising advancements made in the past decade in cancer treatment. Cancer immunotherapy is utilized for generating and augmenting an anti-tumor immune response, e.g., by treatment with antibodies specific to antigens on tumor cells, with fusions of antigen presenting cells with tumor cells, or by activation of anti-tumor T cells. The ability of recruiting immune cells (e.g. T cells) against tumor cells in a patient provides a therapeutic modality of fighting cancer types and metastasis that so far were considered incurable.

T cell mediated immune response includes multiple sequential steps regulated by a balance between co-stimulatory and co-inhibitory signals that control the magnitude of the immune response. The inhibitory signals, referred to as immune checkpoints, are crucial for the maintenance of self-tolerance and for limiting immune-mediated collateral tissue damage. These signals change as an infection or immune provocation is cleared, worsens, or persists, and these changes affect and re-shape the immune response.

The expression of immune checkpoint proteins can be regulated by tumors. For example, upregulation of programmed death ligand-1 (PD-L1) on the cancer cell surface allows them to evade the host immune system by inhibiting T cells via binding to PD-1 that might otherwise attack these tumor cells. Thus, immune checkpoints represent significant barriers to activation of functional cellular immunity against cancer. Accordingly, antagonistic antibodies specific for inhibitory ligands on immune cells are considered viable anti-cancer agents and they are being used in cancer treatment (e.g. Nivolumab and Pembrolizumab). Another example for immune checkpoint molecule is "T cell immunoreceptor with Ig and ITIM domains" (TIGIT). TIGIT is a co-inhibitory molecule expressed on various immune cells including T cells and Natural Killer cells (NK cells). TIGIT binds with high affinity to polio-virus receptor (PVR, CD155). Monoclonal antibodies (mAbs) specific for TIGIT are disclosed for example in WO 2016/028656 and WO 2017/037707.

Poliovirus receptor (PVR), is a transmembrane glycoprotein involved in mediating cell adhesion to extracellular matrix molecules. PVR is a known tumor antigen and a target for therapeutic interventions. Blocking of PVR on tumor cells is anticipated to reduce viability of tumor cells. PVR has also a critical role in angiogenesis and metastasis. Several patent applications including U.S. Patent Application No. 20070041985, U.S. Patent Application No. 20090215175 and WO 2017149538, disclose molecules and antibodies that specifically bind to PVR and their use against cancer.

Nectin Cell Adhesion Molecule 4 (Nectin4), also termed poliovirus receptor-related 4 (PVRL4), is a type I transmembrane protein and member of the Nectin family of related immunoglobulin-like adhesion molecules. Nectin4 is a tumor associated marker for many tumors including lung, breast, colon, and ovarian cancers.

Chailta-Eid at al. 2016 (Cancer Res. 2016; 76:3003-13) discloses anti Nectin4 (Enfortumab) antibody-drug conjugate as a highly potent therapeutic agent in multiple pre-clinical cancer models. The antibody, conjugated with the microtubule inhibitor vedotin, binds human, as well as rat and monkey nectin4 and inhibits growth of several cell lines and xenografts that express nectin4.

Despite of the success made in cancer immunotherapy, there is still an unmet need for additional approaches, and more effective and specific agents and drug combinations to potentiate cells of the immune system to attack tumor cells. One such approach involves inhibiting Nectin4 binding to TIGIT by specific monoclonal antibodies.

SUMMARY OF THE INVENTION

The present invention provides antibodies and fragments thereof which bind to the human protein Nectin4, to polynucleotide sequences encoding these antibodies and to cells producing these antibodies. The present invention is based in part on the discovery that Nectin4, previously known as a receptor for measles virus and a tumor antigen, is a ligand for the immune-inhibitory molecule TIGIT and therefore proposed for the first time as a target for inhibition of the suppressive effect of TIGIT on anti-cancer immunity. The present invention further provides in some embodiments chimeric antigen receptors (CARs) comprising a binding site to Nectin4.

The present invention provides highly effective monoclonal antibodies (mAbs) specific to human Nectin4, which not only block the interaction between Nectin4 and the inhibitory receptor TIGIT, but also have direct effect on target cells expressing this receptor. These antibodies, having binding constant to Nectin4 in the sub-nanomolar range, reverse TIGIT inhibition of the immune system and directly enhance elimination of tumor cells, without being conjugated to any toxin or anti-tumor agent. The antibodies of the present invention are therefore useful for inhibition of the interaction between Nectin4 on target cells and TIGIT on immune cells, for example in cancer immunotherapy. Moreover, some intact antibodies described herein induce ADCC (antibody-dependent cell-mediated cytotoxicity) activity. Nectin4 is specifically overexpressed on tumor cells. ADCC activity induction together with the high affinity of the antibodies of the present invention to Nectin4 and their ADCC activity, makes them ideal candidates for immunotherapy.

The present invention provides antibodies and fragments thereof that recognize the protein Nectin4, prevent its binding to the protein TIGIT and inhibit suppressive activity on lymphocytes such as natural killer (NK) cells and T-cells. The anti-Nectin4 antibodies disclosed herein are capable of binding to Nectin4 present on target cells such as cancer cells. The antibodies and fragment of the present invention are characterized by having unique sets of complementarity-determining regions (CDR) sequences, high affinity and high specificity to human Nectin4, and are useful in cancer immunotherapy for combating tumor immune evasion, as stand-alone therapy and in combination with other anti-cancer agents. The antibodies are also useful in preventing viral infections, in particular, prevention of measles infection.

It is now disclosed that the high affinity anti-Nectin4 antibodies disclosed herein block TIGIT-Nectin4 interaction and restore T and NK cells activity.

Some of the monoclonal antibodies of the present invention are also capable of blocking the interaction between Nectin4 and Nectin1, indicating their ability to interfere with invasiveness of tumors expressing Nectin4. In addition, anti Nectin4 mAbs were able to induce NK cell activation in most target cells. Advantageously, the anti-Nectin4 mAbs according to the invention have direct effect on target cancer cells, inducing their killing without the need of NK cells and/or of a toxin. It is further disclosed that the anti-Nectin4 antibodies of the invention had no blocking effect on signaling of the co-stimulatory receptors such as DNAM1, therefore they are expected to have no deleterious effects on other immune induction signals.

Interestingly, despite high sequence similarity between human and rodent Nectin4 sequences, some of the antibodies of the present invention are highly specific to human Nectin4 and do not bind rodent Nectin4.

Some of the anti-Nectin4 mAbs described herein were able to reduce tumor cells viability in an immune independent manner by blocking of Nectin4 on tumor cells. In some embodiments, the Nectin4 antibodies described herein inhibit proliferation of tumor cells, via immune independent interference with binding to Nectin1 on tumor cells, without being bound to any toxic molecule.

According to one aspect, the present invention provides an isolated monoclonal antibody (mAb), or an antibody fragment thereof comprising at least the antigen binding portion, which specifically binds to human Nectin4 and inhibits its binding to TIGIT.

The present invention also provides a mAb or antibody fragment thereof, capable of inhibiting the binding of human Nectin4 to human TIGIT, for use in treatment of cancer, together with T-cell lymphocytes and/or natural killer (NK) cells.

According to some embodiments, the mAb is not conjugated to any toxin or anti-tumor agent.

According to some embodiments, the isolated antibody or antibody fragment comprises a set of six complementarity determining region (CDR) sequences selected from the group consisting of:
  i. three CDRs of a heavy chain (HC) variable region comprising SEQ ID NO: 22 and three CDRs of a light chain (LC) variable comprising SEQ ID NO: 24, or an analog or derivative thereof having at least 90% sequence identity with said antibody or fragment sequence;
  ii. three CDRs of a HC variable region comprising SEQ ID NO: 2 and three CDRs of a LC variable comprising SEQ ID NO: 4, or an analog or derivative thereof having at least 90% sequence identity with said antibody or fragment sequence; and
  iii. three CDRs of a HC variable region comprising SEQ ID NO: 6 and three CDRs of a LC variable region comprising SEQ ID NO: 8, or an analog or derivative thereof having at least 90% sequence identity with said antibody or fragment sequence.

According to some embodiments, the isolated antibody or antibody fragment comprises a set of six CDR sequences selected from the group consisting of:
  iv. three CDRs of a HC variable region comprising SEQ ID NO: 39 and three CDRs of a LC variable comprising SEQ ID NO: 40, or an analog or derivative thereof having at least 90% sequence identity with said antibody or fragment sequence;
  v. three CDRs of a HC variable region comprising SEQ ID NO: 35 and three CDRs of a LC variable comprising SEQ ID NO: 36, or an analog or derivative thereof having at least 90% sequence identity with said antibody or fragment sequence; and
  vi. three CDRs of a HC variable region comprising SEQ ID NO: 37 and three CDRs of a LC variable region comprising SEQ ID NO: 38, or an analog or derivative thereof having at least 90% sequence identity with said antibody or fragment sequence.

There are several methods known in the art for determining the CDR sequences of a given antibody molecule, but there is no standard unequivocal method. Determination of CDR sequences from antibody heavy and light chain variable regions can be made according to any method known in the art, including but not limited to the methods known as KABAT, Chothia and IMGT. A selected set of CDRs may include sequences identified by more than one method, namely, some CDR sequences may be determined using KABAT and some using IMGT, for example. According to some embodiments, the CDR sequences of the mAb variable regions are determined using the IMGT method.

According to some embodiments, the isolated monoclonal antibody or fragment comprises the CDR sequences of a monoclonal antibody denoted hNec4.11 (or Nectin4.11, or clone 11), namely, the three CDR sequences contained in heavy chain variable region set forth in SEQ ID NO: 39 and the three CDR sequences contained in light chain variable region set forth in SEQ ID NO: 40.

According to some embodiments, the isolated monoclonal antibody or the antibody fragment comprises heavy chain CDR1 comprising the sequence SYYIH (SEQ ID NO: 25). According to some embodiments, the isolated monoclonal antibody or the antibody fragment comprises heavy chain CDR2 comprising the sequence WIYPGNVNTKYNERFKG (SEQ ID NO: 26). According to some embodiments, the isolated monoclonal antibody or the antibody fragment comprises heavy chain CDR3 comprising the sequence SNPYVMDY (SEQ ID NO: 27).

According to certain embodiments, the isolated monoclonal antibody or the antibody fragment comprises: (i) HC CDR1 comprising the sequence SYYIH (SEQ ID NO: 25); (ii) HC CDR2 comprising the sequence: WIYPGNVNTKYNERFKG (SEQ ID NO: 26); and (iii) HC CDR3 comprising the sequence: SNPYVMDY (SEQ ID NO: 27).

According to some embodiments, the isolated monoclonal antibody or the antibody fragment comprises light chain CDR1 comprising the sequence KASQSVNNDVA (SEQ ID NO: 28). According to some embodiments, the isolated monoclonal antibody or the antibody fragment comprises light chain CDR2 comprising the sequence YASNRFT (SEQ ID NO: 29). According to some embodiments, the isolated monoclonal antibody or the antibody fragment comprises light chain CDR3 comprising the sequence QQAYRSPYT (SEQ ID NO: 30).

According to certain embodiments, the isolated monoclonal antibody or the antibody fragment comprises: (i) LC CDR1 comprising the sequence KASQSVNNDVA (SEQ ID NO: 28); (ii) LC CDR2 comprising the sequence: YASNRFT (SEQ ID NO: 29); and (iii) HC CDR3 comprising the sequence: QQAYRSPYT (SEQ ID NO: 30).

According to some specific embodiments the isolated monoclonal antibody or fragment comprises heavy chain CDR1 sequence comprising the sequence: SYYIH (SEQ ID NO: 25), heavy chain CDR2 comprising the sequence: WIYPGNVNTKYNERFKG (SEQ ID NO: 26), heavy chain CDR3 comprising the sequence: SNPYVMDY (SEQ ID NO: 27), light chain CDR1 comprising the sequence: KASQSVNNDVA (SEQ ID NO: 28), light chain CDR2 comprising the sequence: YASNRFT (SEQ ID NO: 29), and light chain CDR3 comprising the sequence: QQAYRSPYT (SEQ ID NO: 30), or analogs thereof comprising no more than 5% amino acid substitution, deletion and/or insertion in the hypervariable region (HVR) sequence.

According to some specific embodiments, the isolated monoclonal antibody or fragment comprises a set of six CDR sequences consisting of:
 i. heavy chain CDR1 having a sequence set forth in SEQ ID NO: 25;
 ii. heavy chain CDR2 having a sequence set forth in SEQ ID NO: 26;
 iii. heavy chain CDR3 having a sequence set forth in SEQ ID NO: 27;
 iv. light chain CDR1 having a sequence set forth in SEQ ID NO: 28;
 v. light chain CDR2 having a sequence set forth in SEQ ID NO: 29; and
 vi. light chain CDR3 having a sequence set forth in SEQ ID NO: 30.

According to some embodiments, the isolated monoclonal antibody or fragment thereof comprises heavy chain variable region set forth in SEQ ID NO: 39, or an analog or derivative thereof having at least 90% sequence identity with the heavy chain variable region sequence.

According to some embodiments, the isolated monoclonal antibody or fragment thereof comprises light chain variable region set forth in SEQ ID NO: 40, or an analog thereof having at least 90% sequence identity with the light chain variable region sequence.

According to a specific embodiment, the isolated monoclonal antibody or fragment thereof comprises a heavy chain variable region having a sequence set forth in SEQ ID NO: 39, and a light chain variable region having a sequence set forth in SEQ ID NO: 40, or an analog thereof having at least 90% sequence identity with the light and/or heavy chain sequence.

The invention also encompasses antibody or antibody fragment capable of binding with high affinity to an epitope within the human Nectin4 protein to which monoclonal antibody hNec4.11 binds.

According to some embodiments, the isolated monoclonal antibody or fragment comprises the CDR sequences of a monoclonal antibody denoted hNec4.01 (or Nectin4.01), namely, the three CDR sequences contained in heavy chain variable region set forth in SEQ ID NO: 35 and the three CDR sequences contained in light chain variable region set forth in SEQ ID NO: 36.

According to some embodiments, the isolated monoclonal antibody or the antibody fragment comprises heavy chain CDR1 comprising the sequence AYNIH (SEQ ID NO: 9). According to some embodiments, the isolated monoclonal antibody or the antibody fragment comprises heavy chain CDR2 comprising the sequence YIYPNNGGSGY-NQKFMN (SEQ ID NO: 10). According to some embodiments, the isolated monoclonal antibody or the antibody fragment comprises heavy chain CDR3 comprising the sequence FDYDEAWFIY (SEQ ID NO: 11).

According to certain embodiments, the isolated monoclonal antibody or the antibody fragment comprises: (i) HC CDR1 comprising the sequence AYNIH (SEQ ID NO: 9); (ii) HC CDR2 comprising the sequence: YIYPNNGGSGY-NQKFMN (SEQ ID NO: 10); and (iii) HC CDR3 comprising the sequence: FDYDEAWFIY (SEQ ID NO: 11).

According to some embodiments, the isolated monoclonal antibody or the antibody fragment comprises light chain CDR1 comprising the sequence SASSSVSYMH (SEQ ID NO: 12). According to some embodiments, the isolated monoclonal antibody or the antibody fragment comprises light chain CDR2 comprising the sequence DTSKLAS (SEQ ID NO: 13). According to some embodiments, the isolated monoclonal antibody or the antibody fragment comprises light chain CDR3 comprising the sequence FQGSGSPYT (SEQ ID NO: 14).

According to certain embodiments, the isolated monoclonal antibody or the antibody fragment comprises: (i) LC CDR1 comprising the sequence SASSSVSYMH (SEQ ID NO: 12); (ii) LC CDR2 comprising the sequence: DTSK-LAS (SEQ ID NO: 13); and (iii) HC CDR3 comprising the sequence: FQGSGSPYT (SEQ ID NO: 14).

According to some specific embodiments the isolated monoclonal antibody or fragment comprises heavy chain CDR1 sequence comprising the sequence: AYNIH (SEQ ID NO: 9), heavy chain CDR2 comprising the sequence: YIYPNNGGSGYNQKFMN (SEQ ID NO: 10), heavy chain CDR3 comprising the sequence: FDYDEAWFIY (SEQ ID NO: 11), light chain CDR1 comprising the sequence: SASSSVSYMH (SEQ ID NO: 12), light chain CDR2 comprising the sequence: DTSKLAS (SEQ ID NO: 13), and light chain CDR3 comprising the sequence: FQGSGSPYT (SEQ ID NO: 14), or analogs thereof comprising no more than 5% amino acid substitution, deletion and/or insertion in the hypervariable region (HVR) sequence.

According to some specific embodiments the isolated monoclonal antibody or fragment comprises a set of six CDR sequences consisting of:
 i. heavy chain CDR1 having a sequence set forth in SEQ ID NO: 9;
 ii. heavy chain CDR2 having a sequence set forth in SEQ ID NO: 10;
 iii. heavy chain CDR3 having a sequence set forth in SEQ ID NO: 11;
 iv. light chain CDR1 having a sequence set forth in SEQ ID NO: 12;
 v. light chain CDR2 having a sequence set forth in SEQ ID NO: 13; and
 vi. light chain CDR3 having a sequence set forth in SEQ ID NO: 14.

According to some embodiments, the isolated monoclonal antibody or fragment thereof comprises heavy chain variable region set forth in SEQ ID NO: 35, or an analog or derivative thereof having at least 90% sequence identity with the heavy chain variable region sequence.

According to some embodiments, the isolated monoclonal antibody or fragment thereof comprises light chain variable region set forth in SEQ ID NO: 36, or an analog thereof having at least 90% sequence identity with the light chain variable region sequence.

According to a specific embodiment, the isolated monoclonal antibody or fragment thereof comprises a heavy chain variable region having a sequence set forth in SEQ ID NO: 35, and a light chain variable region having a sequence set forth in SEQ ID NO: 36, or an analog thereof having at least 90% sequence identity with the light and/or heavy chain sequence.

The invention also encompasses antibody or antibody fragment capable of binding with high affinity to an epitope within the human Nectin4 protein to which monoclonal antibody hNec4.01 binds.

According to some embodiments, the isolated monoclonal antibody or fragment comprises the CDR sequences of a monoclonal antibody denoted hNec4.05 (or Nectin4.05), namely, the three CDR sequences contained in heavy chain variable region set forth in SEQ ID NO: 37 and the three CDR sequences contained in light chain variable region set forth in SEQ ID NO: 38.

According to some embodiments, the isolated monoclonal antibody or the antibody fragment comprises heavy chain CDR1 comprising the sequence TYYIH (SEQ ID NO: 15). According to some embodiments, the isolated monoclonal antibody or the antibody fragment comprises heavy chain CDR2 comprising the sequence WIYPGNVNT-KNNEKFKV (SEQ ID NO: 16). According to some embodiments, the isolated monoclonal antibody or the antibody fragment comprises heavy chain CDR3 comprising the sequence SNPYVMDY (SEQ ID NO: 17).

According to certain embodiments, the isolated monoclonal antibody or the antibody fragment comprises: (i) HC CDR1 comprising the sequence TYYIH (SEQ ID NO: 15); (ii) HC CDR2 comprising the sequence: WIYPGNVNT-KNNEKFKV (SEQ ID NO: 16); and (iii) HC CDR3 comprising the sequence: SNPYVMDY (SEQ ID NO: 17).

According to some embodiments, the isolated monoclonal antibody or the antibody fragment comprises light chain CDR1 comprising the sequence KASQSVSNDVA (SEQ ID NO: 18). According to some embodiments, the isolated monoclonal antibody or the antibody fragment comprises light chain CDR2 comprising the sequence YASNRYT (SEQ ID NO: 19). According to some embodiments, the isolated monoclonal antibody or the antibody fragment comprises light chain CDR3 comprising the sequence QQD-YSSPYT (SEQ ID NO: 20).

According to certain embodiments, the isolated monoclonal antibody or the antibody fragment comprises: (i) LC CDR1 comprising the sequence KASQSVSNDVA (SEQ ID NO: 18); (ii) LC CDR2 comprising the sequence: YASN-RYT (SEQ ID NO: 19); and (iii) HC CDR3 comprising the sequence: QQDYSSPYT (SEQ ID NO: 20).

According to some specific embodiments the isolated monoclonal antibody or fragment comprises heavy chain CDR1 sequence comprising the sequence: TYYIH (SEQ ID NO: 15), heavy chain CDR2 comprising the sequence: WIYPGNVNTKNNEKFKV (SEQ ID NO: 16), heavy chain CDR3 comprising the sequence: SNPYVMDY (SEQ ID NO: 17), light chain CDR1 comprising the sequence: KASQSVSNDVA (SEQ ID NO: 18), light chain CDR2 comprising the sequence: YASNRYT (SEQ ID NO: 19), and light chain CDR3 comprising the sequence: QQDYSSPYT (SEQ ID NO: 20), or analogs thereof comprising no more than 5% amino acid substitution, deletion and/or insertion in the hypervariable region (HVR) sequence.

According to some specific embodiments the isolated monoclonal antibody or fragment comprises a set of six CDR sequences consisting of:
i. heavy chain CDR1 having a sequence set forth in SEQ ID NO: 15;
ii. heavy chain CDR2 having a sequence set forth in SEQ ID NO: 16;
iii. heavy chain CDR3 having a sequence set forth in SEQ ID NO: 17;
iv. light chain CDR1 having a sequence set forth in SEQ ID NO: 18;
v. light chain CDR2 having a sequence set forth in SEQ ID NO: 19; and
vi. light chain CDR3 having a sequence set forth in SEQ ID NO: 20.

According to some embodiments, the isolated monoclonal antibody or fragment thereof comprises heavy chain variable region sequence set forth in SEQ ID NO: 37, or an analog or derivative thereof having at least 90% sequence identity with the heavy chain variable region sequence.

According to some embodiments, the isolated monoclonal antibody or fragment thereof comprises light chain variable region set forth in SEQ ID NO: 38, or an analog thereof having at least 90% sequence identity with the light chain variable region sequence.

According to a specific embodiment, the isolated monoclonal antibody or fragment thereof comprises a heavy chain variable region having a sequence set forth in SEQ ID NO: 37, and a light chain variable region having a sequence set forth in SEQ ID NO: 38, or an analog thereof having at least 90% sequence identity with the light and/or heavy chain sequence.

The invention also encompasses antibody or antibody fragment capable of binding with high affinity to an epitope within the human Nectin4 protein to which monoclonal antibody hNec4.05 binds.

According to some embodiments, the isolated antibody or fragment thereof recognizes human Nectin4 with an affinity of at least $10^{-8}$M. According to other embodiments, the antibody or antibody fragment binds human Nectin4 with an affinity of $10^{-8}$M, $5\times10^{-9}$M, $10^{-9}$M, $5\times10^{-10}$M, $10^{-10}$M, $5\times10^{-11}$M or even higher. According to some embodiments, the antibody or antibody fragment binds to human Nectin4 with an affinity of $10^{-9}$M to $10^{-10}$M. Each possibility represents a separate embodiment of the invention.

Analogs and derivatives of the isolated mAbs, and the fragments described above, are also within the scope of the invention.

According to some embodiments, the antibody or antibody fragment analog have at least 90% sequence identity with the hypervariable region of the reference antibody sequence.

According to certain embodiments, the analog or derivative of the isolated antibody or fragment thereof has at least 91, 92, 93, 94, 95, 96, 97, 98 or 99% sequence identity with a variable region of the reference antibody sequence. Each possibility represents a separate embodiment of the invention.

According to some embodiments, the antibody or antibody fragment according to the invention comprises a heavy chain variable region set forth in SEQ ID NO: 39, SEQ ID NO: 35 or SEQ ID NO: 37, or an analog having at least 95% sequence similarity with said sequence.

According to some embodiments, the antibody or antibody fragment comprises a light chain variable region set forth in SEQ ID NO: 40, SEQ ID NO: 36 or SEQ ID NO: 38, or an analog having at least 95% sequence similarity with said sequence.

According to some embodiments, the antibody or antibody fragment comprises a heavy chain and a light chain, wherein: (i) the heavy chain comprises SEQ ID NO: 39 and the light chain comprises SEQ ID NO: 40; (ii) the heavy chain comprises SEQ ID NO: 35 and the light chain comprises SEQ ID NO: 36; or (iii) the heavy chain comprises SEQ ID NO: 37 and the light chain comprises SEQ ID NO: 38. Analogs of the antibodies or fragments, having at least 95% sequence similarity with said heavy or light chains are also included.

According to some embodiments, the analog has at least 96, 97, 98 or 99% sequence identity with an antibody light or heavy chain variable regions described above. According to some embodiments, the analog comprises no more than one amino acid substitution, deletion or addition to one or more CDR sequences of the hypervariable region, namely, any one of the CDR sequences set forth in SEQ ID NOs: 25, 26, 27, 28, 29, 30, 9, 10, 11, 12, 13, 14, 15, 16, 17, 18, 19 and 20. Each possibility represents a separate embodiment of the present invention. According to some embodiments, the amino acid substitution is a conservative substitution.

According to some embodiments, the antibody or antibody fragment comprises a hypervariable region (HVR) having light and heavy chain regions defined above, in which 1, 2, 3, 4, or 5 amino acids were substituted, deleted and/or added. Each possibility represents a separate embodiment of the invention.

According to some embodiments, the antibody or antibody fragment comprises an HVR having light and heavy chain regions defined above, in which one amino acid was substituted. According to specific embodiments, the antibody or antibody fragment comprises a CDR as defined above, in which one amino acid was substituted.

According to some embodiments, the isolated monoclonal antibody or the antibody fragment comprises a CDR set selected from the group consisting of:
 i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);
 ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and
 iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

The present invention also provides monoclonal antibodies and binding fragments thereof, comprising a heavy chain and a light chain, wherein said chains comprises a set of heavy chain variable region sequence and light chain variable region sequence, said set is selected from the group consisting of:
 i. a set comprising SEQ ID NOs: 39 and 40;
 ii. a set comprising SEQ ID NOs: 35 and 36; and
 iii. a set comprising SEQ ID NOs: 37 and 38.

According to some embodiments, the antibody or antibody fragment is capable of inhibiting human Nectin4 binding to TIGIT expressed on T cells or NK cells.

According to a specific embodiment, the mAb is selected from the group consisting of: chimeric antibody and an antibody fragment comprising at least the antigen-binding portion of an antibody. According to specific embodiments, the antibody is a chimeric antibody. According to yet other embodiments, the chimeric antibody comprised human constant region. According to a specific embodiment, the antibody fragment is selected from the group consisting of: Fab, Fab', F(ab')₂, Fd, Fd', Fv, dAb, isolated CDR region, single chain variable region (scFV), single chain antibody (scab), "diabodies", and "linear antibodies". Each possibility represents a separate embodiment of the present invention.

A single chain variable region (scFV) comprising the heavy chain and light chain variable regions of the antibodies described herein is also provided according to the present invention. According to certain embodiments, there is a hinge region between the variable regions.

According to some embodiments, the scFV sequence is set forth in SEQ ID NO: 32, SEQ ID NO: 34, or an analog thereof having at least 90% sequence similarity to said sequences.

According to some embodiments, the antibody comprises a constant region sequence selected from the group consisting of: mouse IgG1, mouse IgG2a, mouse IgG2b, mouse IgG3, human IgG1, human IgG2, human IgG3 and human IgG4. Each possibility represents a separate embodiment of the present invention.

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, human IgG3, and human IgG4.

According to specific embodiments, the antibody is a human IgG1. According to some embodiments, a human IgG comprising the variable regions of the antibodies described herein is provided.

According to some embodiments, a conjugate comprising an antibody or fragment thereof as described above is provided.

According to some embodiments, the conjugate comprises a carrier protein.

A chimeric antigen receptor (CAR) comprising an extracellular portion (binding domain), capable of binding to Nectin4 is provided according to another aspect of the present invention.

According to some embodiments, the CAR comprises an extracellular portion containing any of the provided antibodies or fragment thereof as described herein.

According to some embodiments, the CAR comprises a Nectin4 binding site comprising a CDR set selected from the group consisting of:
 i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);
 ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and
 iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

According to some embodiments, the CAR comprises an antigen binding domain comprising SEQ ID NOs: 32 or 34, a transmembrane domain, and an intracellular T cell signaling domain.

According to an aspect, the present invention provides an isolated nucleic acid molecule encoding a CAR comprising an antibody or antibody fragment which includes Nectin4 binding domain comprising a CDR set selected from the group consisting of:

i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);

ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

According to some embodiments, a vector comprises a polynucleotide sequence set forth in SEQ ID NO: 31 or SEQ ID NO: 33, or an analog having at least 95% similarity with said sequence is provided.

According to some embodiments, a T cell engineered to express the CAR described herein is provided.

According to additional embodiments, an NK cell engineered to express the CAR described herein is provided.

Polynucleotide sequences encoding monoclonal antibodies, having high affinity and specificity for human Nectin4, as well as vectors and host cells carrying these polynucleotide sequences, are provided according to another aspect of the present invention.

According to some embodiments, polynucleotide sequences encoding the amino acid sequences of heavy chain variable region and light chain variable region described above are provided.

According to some embodiments, the polynucleotide sequence encodes an antibody or antibody fragment or chain capable of binding to an epitope within the human Nectin4 protein to which binds: (i) a monoclonal antibody (herein identified as hNec4.11) having a heavy chain variable region of SEQ ID NO: 39 and a light chain variable region of SEQ ID NO: 40; (ii) a monoclonal antibody (herein identified as hNec4.01) having a heavy chain variable region of SEQ ID NO: 35 and a light chain variable region of SEQ ID NO: 36; or (iii) a monoclonal antibody (herein identified as hNec4.05) having a heavy chain variable region of SEQ ID NO: 37 and a light chain variable region of SEQ ID NO: 38.

According to some embodiments, the polynucleotide sequence encodes an antibody or antibody fragment or chain comprising the sequence set forth in a sequence selected from the group consisting of: SEQ ID NO: 39 and SEQ ID NO: 40; SEQ ID NO: 35 and SEQ ID NO: 36; or SEQ ID NO: 37 and SEQ ID NO: 38. Each possibility represents a separate embodiment of the present invention.

According to yet some embodiments, the polynucleotide sequence according to the invention encodes an antibody or antibody fragment or chain comprising:

i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);

ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

Each possibility represents a separate embodiment of the present invention.

According to some embodiments, the polynucleotide sequences defined above encode a molecule selected from the group consisting of: an antibody, an antibody fragment comprising at least an antigen-binding portion, and an antibody conjugate comprising said antibody or antibody fragment. Each possibility represents a separate embodiment of the present invention.

According to some embodiments, the polynucleotide sequence encoding a monoclonal antibody heavy chain variable region comprises a sequence set forth in SEQ ID NO: 21 or a variant thereof having at least 90% sequence identity.

According to some embodiments, the polynucleotide sequence encoding a monoclonal antibody heavy chain variable region comprises a sequence set forth in SEQ ID NO: 1 or a variant thereof having at least 90% sequence identity.

According to some embodiments, the polynucleotide sequence encoding a monoclonal antibody heavy chain variable region, comprises a sequence set forth in SEQ ID NO: 5, or a variant thereof having at least 90% sequence identity.

According to some embodiments, the polynucleotide sequence encoding a monoclonal antibody light chain variable region comprises a sequence set forth in SEQ ID NO: 23 or a variant thereof having at least 90% sequence identity.

According to some embodiments, the polynucleotide sequence encoding a monoclonal antibody light chain variable region comprises a sequence set forth in SEQ ID NO: 3 or a variant thereof having at least 90% sequence identity.

According to some embodiments, the polynucleotide sequence encoding a monoclonal antibody light chain variable region comprises a sequence set forth in SEQ ID NO: 7, or a variant thereof having at least 90% sequence identity.

According to some embodiments, the polynucleotide sequence encoding a monoclonal antibody heavy chain variable region comprises a sequence set forth in SEQ ID NO: 45 or a variant thereof having at least 90% sequence identity.

According to some embodiments, the polynucleotide sequence encoding a monoclonal antibody heavy chain variable region comprises a sequence set forth in SEQ ID NO: 41 or a variant thereof having at least 90% sequence identity.

According to some embodiments, the polynucleotide sequence encoding a monoclonal antibody heavy chain variable region, comprises a sequence set forth in SEQ ID NO: 43, or a variant thereof having at least 90% sequence identity.

According to some embodiments, the polynucleotide sequence encoding a monoclonal antibody light chain variable region comprises a sequence set forth in SEQ ID NO: 46 or a variant thereof having at least 90% sequence identity.

According to some embodiments, the polynucleotide sequence encoding a monoclonal antibody light chain variable region comprises a sequence set forth in SEQ ID NO: 42 or a variant thereof having at least 90% sequence identity.

According to some embodiments, the polynucleotide sequence encoding a monoclonal antibody light chain variable region comprises a sequence set forth in SEQ ID NO: 44, or a variant thereof having at least 90% sequence identity.

The present invention provides, according to some embodiments, a polypeptide comprising at least one sequence encoded by at least one polynucleotide sequence disclosed above.

In a further aspect, the present invention provides a nucleic acid construct comprising a nucleic acid molecule encoding at least one antibody chain or fragment thereof according to the present invention. According to some embodiments the nucleic acid construct is a plasmid.

According to some embodiments the plasmid comprises at least one polynucleotide sequence set forth in a sequence selected from the group consisting of SEQ ID NO: 45, SEQ ID NO: 46, SEQ ID NO: 41, SEQ ID NO: 42, SEQ ID NO: 43 and SEQ ID NO: 44. Each possibility represents a separate embodiment of the present invention.

In still another aspect the present invention provides a cell capable of producing an antibody or an antibody fragment comprising the specific CDR sequences and/or specific heavy and light chain variable regions defined above.

According to some embodiments, a cell is provided comprising at least one polynucleotide sequence disclosed above.

According to some embodiments, the cell is cable of producing a monoclonal antibody comprising:
  i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);
  ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and
  iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

Each possibility represents a separate embodiment of the present invention.

According to some embodiments, the cell producing the monoclonal antibody in a hybridoma cell.

Antibodies or fragments thereof according to the present invention may be attached to a cytotoxic moiety, a radioactive moiety, or an identifiable moiety.

The present invention provides, according to another aspect, a pharmaceutical composition comprising as an active ingredient, at least one antibody, antibody fragment or conjugates thereof, that recognizes human Nectin4 with high affinity and specificity, and optionally at least one pharmaceutical acceptable excipient, diluent, salt or carrier, wherein said at least one antibody or antibody fragment is capable of inhibiting the binding of human Nectin4 to human TIGIT.

According to some embodiments, the pharmaceutical composition comprises a mAb specific to Nectin4, wherein the mAb is not conjugated to any toxin or anti-tumor agent.

According to some embodiments, the pharmaceutical composition comprises a monoclonal antibody or a fragment thereof which is capable of binding to an epitope within the human Nectin4 protein to which binds a monoclonal antibody selected from the group consisting of: hNec4.11, hNec4.01 and hNec4.05 having variable region and CDR sequences disclosed above.

According to some embodiments, the pharmaceutical composition comprises at least one monoclonal antibody comprising:
  i. a set of six CDRs wherein: HC CDR1 is SEQ ID NO: 25; HC CDR2 is SEQ ID NO: 26; HC CDR3 is SEQ ID NO: 27; LC CDR1 is SEQ ID NO: 28; LC CDR2 is SEQ ID NO: 29; and LC CDR3 is SEQ ID NO: 30;
  ii. a set of six CDRs wherein: HC CDR1 is SEQ ID NO: 9; HC CDR2 is SEQ ID NO: 10; HC CDR3 is SEQ ID NO: 11; LC CDR1 is SEQ ID NO: 12; LC CDR2 is SEQ ID NO: 13; and LC CDR3 is SEQ ID NO: 14; or
  iii. a set of six CDRs wherein: HC CDR1 sequence is SEQ ID NO: 15; HC CDR2 is SEQ ID NO: 16; HC CDR3 is SEQ ID NO: 17; LC CDR1 is SEQ ID NO: 18; LC CDR2 is SEQ ID NO: 19; and LC CDR3 is SEQ ID NO: 20.

Each possibility represents a separate embodiment of the present invention.

According to some embodiments, the pharmaceutical composition comprises a monoclonal antibody or fragment thereof comprising a heavy chain variable region having a sequence selected from the group consisting of SEQ ID NO: 39, SEQ ID NO: 35, and SEQ ID NO: 37. Each possibility represents a separate embodiment of the invention According to some embodiments, the pharmaceutical composition comprises a monoclonal antibody or fragment thereof comprising a light chain variable region having a sequence selected from the group consisting of SEQ ID NO: 40, SEQ ID NO: 36, and SEQ ID NO: 38. Each possibility represents a separate embodiment of the invention.

According to a specific embodiment, the pharmaceutical composition comprises a monoclonal antibody or fragment thereof comprising a heavy chain variable region having the sequence set forth in SEQ ID NO: 39 and a light chain variable region having the sequence set forth in SEQ ID NO: 40.

According to a specific embodiment, the pharmaceutical composition comprises a monoclonal antibody or fragment thereof comprising a heavy chain variable region having the sequence set forth in SEQ ID NO: 35 and a light chain variable region having the sequence set forth in SEQ ID NO: 36.

According to a specific embodiment, the pharmaceutical composition comprises a monoclonal antibody or fragment thereof comprising a heavy chain variable region having the sequence set forth in SEQ ID NO: 37 and a light chain variable region having the sequence set forth in SEQ ID NO: 38.

Also provided are pharmaceutical compositions, comprising at least one antibody, antibody fragment or antibody conjugate according to the invention, for use in restoring NK cytotoxicity by inhibiting binding of Nectin4 to TIGIT expressed on NK cells.

According to some embodiments, the antibody, antibody fragment or antibody conjugate is capable of inhibiting human Nectin4 binding to TIGIT expressed on T-cells.

According to some embodiments, the pharmaceutical composition according to the present invention is for use in cancer immunotherapy or in enhancing immune response.

According to some embodiments, the pharmaceutical composition further comprises human lymphocytes expressing TIGIT.

According to some embodiments, the human lymphocytes are killer cells selected from the group consisting of: T cells, NK cells and natural killer T (NKT cells).

According to some embodiments, the killer cells are autologous or allogenic.

According to some embodiments, the pharmaceutical composition comprises autologous or allogenic NK cells expressing TIGIT.

The cancer treatable with a composition according to the present invention may be any cancer that expresses Nectin4. According to some embodiments, the cancer overexpresses Nectin4. According to some embodiments of the invention, the cancer is a metastatic cancer. According to some embodiments, the pharmaceutical composition according to the present invention is for use in inhibiting formation or distribution of metastases or reducing the total number of metastases in a subject.

According to some embodiments of the invention, the cancer is selected from the group consisting of a melanoma, a breast cancer, an ovarian cancer, a pancreatic cancer, a colorectal cancer, a colon cancer, a cervical cancer, a kidney cancer, a lung cancer, a thyroid cancer, a prostate cancer, a brain cancer, a renal cancer, a throat cancer, a laryngeal carcinoma, a bladder cancer, a hepatic cancer, a fibrosarcoma, an endometrial cells cancer, a glioblastoma, sarcoma, a myeloid, a leukemia and a lymphoma. Each possibility represents a separate embodiment of the invention.

According to some embodiments, the cancer is a solid cancer. According to some specific embodiments, the solid cancer is selected from the group consisting breast cancer, lung cancer, bladder cancer, pancreatic cancer and ovarian cancer.

According to other embodiments, the cancer is hematologic cancer. According to some embodiments, the pharmaceutical composition if for use of treating cancer, together with human lymphocytes.

According to some embodiments, the human lymphocytes are killer cells selected from the group consisting of: T cells, NK cells and NKT cells.

According to some embodiments, the killer cells are autologous or allogenic.

According to some embodiments, the killer cells are NK cells.

According to some embodiments, the pharmaceutical composition according to the present invention is for use in preventing or treating a viral infection.

According to some embodiments, the pharmaceutical composition is for use of preventing infection with measles virus.

According to yet another aspect, the present invention provides a method of inhibiting binding of human Nectin4 to TIGIT by using a monoclonal antibody or antibody fragment defined above.

According to yet another aspect, the present invention provides a method of treating cancer comprising administering to a subject in need thereof, an antibody or fragment thereof which binds to Nectin4 wherein the antibody of fragment thereof is not conjugated to any toxin or anti-tumor agent.

According to an additional aspect, the present invention provides a method for enhancing immune response in a subject in need thereof comprising administering to said subject a therapeutically effective amount of a monoclonal antibody, antibody fragment or antibody conjugate defined above.

According to yet another aspect, the present invention provides a method of treating cancer comprising administering to a subject in need thereof, a pharmaceutical composition comprising a therapeutically effective amount at least one antibody or antibody fragment thereof, that recognizes human Nectin4 with high affinity and specificity and capable of inhibiting its binding to its ligand TIGIT.

According to some embodiments of the invention, the therapeutically effective amount results in a decrease in tumor size or in the number of metastases in the subject.

According to some embodiments, the method comprises administering a pharmaceutical composition comprising a mAb that is not conjugated to any toxin or anti-tumor agent.

According to some embodiments, the method of treating cancer comprises administering or performing at least one additional anti-cancer therapy. According to certain embodiments, the additional anticancer therapy is surgery, chemotherapy, radiotherapy, or immunotherapy.

According to some embodiments, the method of treating cancer comprises administration of a monoclonal antibody that recognizes human Nectin4 with high affinity and specificity and an additional anti-cancer agent. According to some embodiments, the additional anti-cancer agent is selected from the group consisting of: immune-modulator, activated lymphocyte cell, kinase inhibitor and chemotherapeutic agent.

According to other embodiments, the additional immune-modulator is an antibody, antibody fragment or antibody conjugate that binds to an antigen other than human Nectin4.

According to some embodiments, the additional immune-modulator is an antibody against an immune checkpoint molecule. According to some embodiments, the additional immune modulator is an antibody against an immune checkpoint molecule selected from the group consisting of human programmed cell death protein 1 (PD-1), PD-L1 and PD-L2, carcinoembryonic antigen-related cell adhesion molecule 1 (CEACAM1), lymphocyte activation gene 3 (LAG3), CD137, OX40 (also referred to as CD134), killer cell immunoglobulin-like receptors (KIR), TIGIT, PVR, CTLA-4, NKG2A, GITR and any other checkpoint molecule or a combination thereof. Each possibility represents a separate embodiment of the invention.

According to some embodiments, the anti-cancer agent is selected from the group consisting of: Erbitux, cytarabine, fludarabine, fluorouracil, mercaptopurine, methotrexate, thioguanine, gemcitabine, vincristine, vinblastine, vinorelbine, carmustine, lomustine, chlorambucil, cyclophosphamide, cisplatin, carboplatin, ifosfamide, mechlorethamine, melphalan, thiotepa, dacarbazine, bleomycin, dactinomycin, daunorubicin, doxorubicin, idarubicin, mitomycin, mitoxantrone, plicamycin, etoposide, teniposide and any combination thereof. Each possibility represents a separate embodiment of the invention.

According to some embodiments, the anti-cancer agent is epidermal growth factor receptor (EGFR) inhibitor. According to some embodiments, the EGFR inhibitor is selected from the group consisting of: Cetuximab (Erbitux®), Panitumumab (Vectibix®), and necitumumab (Portrazza®). According to some embodiments, the EGFR inhibitor is Cetuximab (Erbitux®).

According to some embodiments of the invention, the subject is a human subject.

According to some embodiments of the invention, the use further comprises the use of an agent that downregulates the activity or expression of an immune co-inhibitory receptor.

According to some embodiments of the invention, the immune cell is a T cell.

According to some embodiments of the invention, the immune co-inhibitory receptor is selected from the group consisting of PD-1, TIGIT, PVR, CTLA-4, LAG3, TIM3, BTLA, VISTA, B7H4, CD96, BY55, LAIR1, SIGLEC10, and 2B4. Each possibility represents a separate embodiment of the invention.

According to an aspect, the present invention provides a method for modulating immune system function and/or activity comprising modulating the binding of Nectin4 to TIGIT using an antibody according to the invention.

According to some embodiments, the method of treating cancer involves preventing or reducing formation, growth or spread of metastases in a subject.

According to some embodiments, the method of treating cancer comprises administering to a subject in need thereof a pharmaceutical composition comprising a mAb or antibody fragment thereof, capable of inhibiting the binding of human Nectin4 to human TIGIT, and further administrating to said subject human lymphocytes.

According to some embodiments, the human lymphocytes are killer cells selected from the group consisting of: T cells, NK cells and NKT cells.

According to some embodiments, the killer cells are autologous or allogenic.

According to some embodiments, the killer cells are NK cells.

The present invention also provides a method of preventing or treating a viral infection comprising administering to a subject at least one mAb specific to human Nectin4, or a fragment thereof comprising at least the antigen binding domain, wherein said mAb or fragment thereof is capable of inhibiting binding of Nectin4 to TIGIT.

According to some embodiments, a method of preventing infection with measles virus is provided comprising administering a mAb specific to human Nectin4, or a fragment thereof comprising at least the antigen binding domain, wherein said mAb or fragment thereof is capable of inhibiting binding of measles virus to human Nectin4 expressed on epithelial cells. According to some embodiments, the cells are epithelial cells. According to an aspect, the present invention provides a method of diagnosing or prognosing cancer or infectious disease in a subject, the method comprises determining the expression level of Nectin4 in a biological sample of said subject using at least one antibody as described herein.

According to yet another aspect, the present invention provides a method of treating cancer comprising administering to a subject in need thereof, a therapeutically effective amount of a cell comprising a CAR molecule as described herein.

The present invention further comprises, according to another aspect, a method of determining or quantifying the expression of Nectin4, the method comprising contacting a biological sample with an antibody or antibody fragment, and measuring the level of complex formation, wherein the antibody or antibody fragment comprises:
  i. a set of six CDRs wherein: HC CDR1 is SEQ ID NO: 25; HC CDR2 is SEQ ID NO: 26; HC CDR3 is SEQ ID NO: 27; LC CDR1 is SEQ ID NO: 28; LC CDR2 is SEQ ID NO: 29; and LC CDR3 is SEQ ID NO: 30;
  ii. a set of six CDRs wherein: HC CDR1 is SEQ ID NO: 9; HC CDR2 is SEQ ID NO: 10; HC CDR3 is SEQ ID NO: 11; LC CDR1 is SEQ ID NO: 12; LC CDR2 is SEQ ID NO: 13; and LC CDR3 is SEQ ID NO: 14; or
  iii. a set of six CDRs wherein: HC CDR1 sequence is SEQ ID NO: 15; HC CDR2 is SEQ ID NO: 16; HC CDR3 is SEQ ID NO: 17; LC CDR1 is SEQ ID NO: 18; LC CDR2 is SEQ ID NO: 19; and LC CDR3 is SEQ ID NO: 20.

Determining and quantifying methods may be performed in-vitro or ex-vivo according to some embodiments or may be used in diagnosing conditions associated with expression of Nectin4. The antibodies according to the present invention may be also used to configure screening methods. For example, an enzyme-linked immunosorbent assay (ELISA), or a radioimmunoassay (RIA), as well as method such as IHC or FACS, can be constructed for measuring levels of secreted or cell-associated polypeptide using the antibodies and methods known in the art.

According to some embodiments, the method for detecting or quantifying the presence of Nectin4 expressed on cells or secreted to a biological medium, comprises the steps of:
  i. incubating a sample with an antibody specific to human Nectin4 or an antibody fragment thereof comprising at least an antigen-binding portion;
  ii. detecting the bound Nectin4 using a detectable probe.
According to some embodiments, the method further comprises the steps of:
  iii. comparing the amount of (ii) to a standard curve obtained from a reference sample containing a known amount of Nectin4; and
  iv. calculating the amount of the Nectin4 in the sample from the standard curve.

According to some particular embodiments the sample is a body fluid.

According to some embodiments, the method is performed in-vitro or ex-vivo.

A kit for measuring the expression or presence of Nectin4 in biological sample is also provided comprising at least one antibody or antibody fragment according to the present invention. According to some embodiments, the kit comprises an antibody or antibody fragment comprising:
  i. a set of six CDRs wherein: HC CDR1 is SEQ ID NO: 25; HC CDR2 is SEQ ID NO: 26; HC CDR3 is SEQ ID NO: 27; LC CDR1 is SEQ ID NO: 28; LC CDR2 is SEQ ID NO: 29; and LC CDR3 is SEQ ID NO: 30;
  ii. a set of six CDRs wherein: HC CDR1 is SEQ ID NO: 9; HC CDR2 is SEQ ID NO: 10; HC CDR3 is SEQ ID NO: 11; LC CDR1 is SEQ ID NO: 12; LC CDR2 is SEQ ID NO: 13; and LC CDR3 is SEQ ID NO: 14; or
  iii. a set of six CDRs wherein: HC CDR1 sequence is SEQ ID NO: 15; HC CDR2 is SEQ ID NO: 16; HC CDR3 is SEQ ID NO: 17; LC CDR1 is SEQ ID NO: 18; LC CDR2 is SEQ ID NO: 19; and LC CDR3 is SEQ ID NO: 20.

According to an aspect, the present invention provides a kit for detecting cancer, the diagnostic kit comprises an antibody or antibody fragment thereof as disclosed herein.

According to some embodiments, the invention provides a method of diagnosing, assessing the severity or staging an immune-related disease or a proliferative disease comprising determining the expression, concentration or activity of Nectin4 in a sample from a subject using an antibody according to the present invention or a fragment or conjugate thereof, and comparing the expression or activity of Nectin4 to a reference amount of Nectin4 expression, concentration or activity. Said reference amount may be obtained from a sample taken from a normal subject, from the same subject while being in a different stage of the disease or is determined from clinical data of a large population of subjects.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 5A-5C Antibody clones do not bind murine Nectin4. (A) Western blots of RAJI cells transfected with murine Nectin4 (indicated as mNectin4) and detected with commercial anti-murine Nectin4 mAb (Clone 356704 which doesn't work for flow cytometry). Expression was compared to RAJI cells expressing empty vector (indicated as Empty). Staining for hGAPDH was used as loading control. (B-C) FACS staining of RAJI cells transfected with murine Nectin4 (black line histograms). Cells were stained with 0.2 μg of (B) clone hNec4.01 or (C) clone hNec4.05.

DETAILED DESCRIPTION OF THE INVENTION

Figure 1:
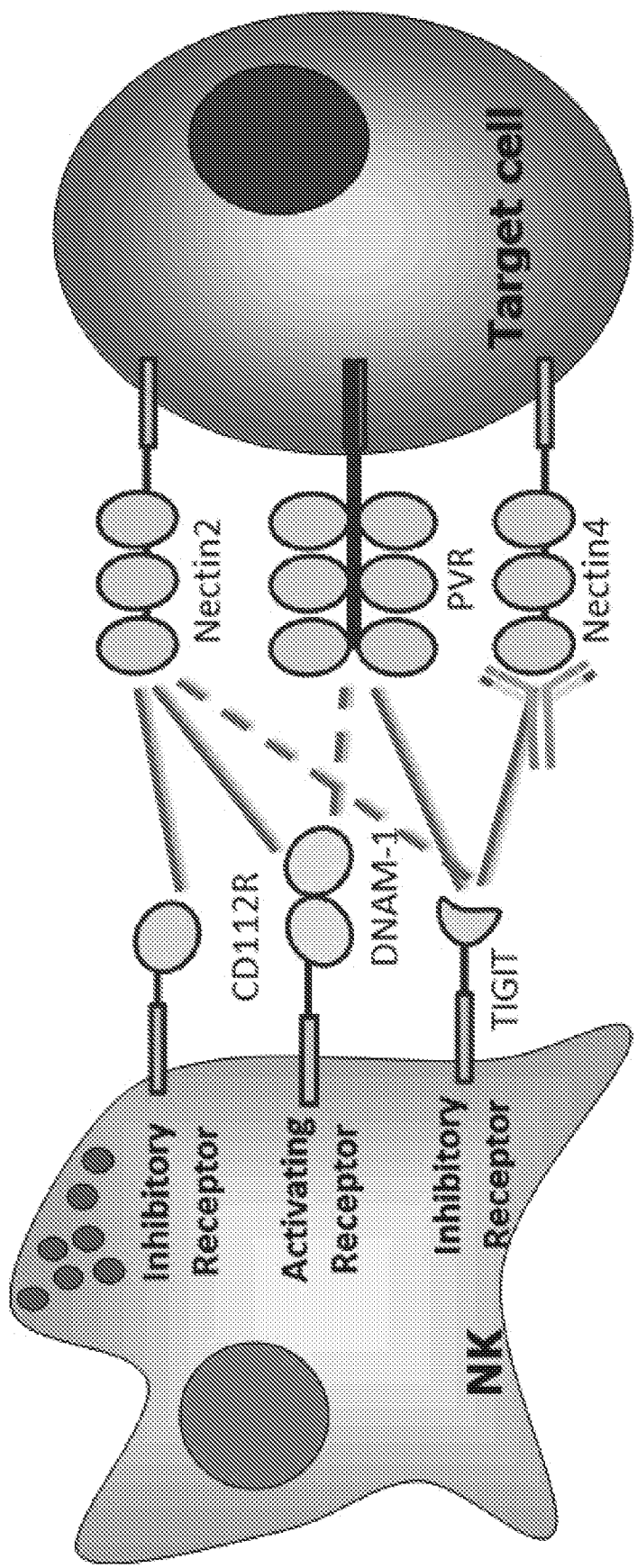
FIG. 1 A schematic illustration of the receptors involved in TIGIT signaling on immune (NK) and tumor cells. Anti nectin4 Ab is depicted.

The present invention provides effective monoclonal antibodies specific to the human Nectin4. The invention also provides production and use of the mAbs as therapeutic agents. In particular, the mAbs of the present invention may be used for restoring and augmenting anti-tumor killing activity of immune cells, and as diagnostic reagents.

While prior publication shows the use of an anti Nectin4 mAb for targeting a drug to tumor cells overexpressing Nectin4, the present invention discloses for the first time monoclonal antibodies that directly potentiate the immune system against tumor cells, by inhibiting the binding to Nectin4 to the inhibitory receptor TIGIT of immune cells such as NK cells.

The antibodies of the present invention overcome the disadvantages of antibodies specific to TIGIT, which are currently tested for treatment of cancer. Anti-TIGIT antibodies may, allegedly, skew the entire immune system towards activation by blocking all immune cells expressing TIGIT receptor and cause, potentially, autoimmune effects, while the anti-Nectin4 antibodies of the present invention target only Nectin4 expressing cells which are known to be overexpressed in tumors.

Furthermore, some of the antibodies of the present invention may also lead to an immune independent killing of tumor cells, potentially via their ability to block nectin4 interactions with nectin1.

The term "antigen" as used herein refers to a molecule or a portion of a molecule capable of eliciting antibody formation and being specifically bound by an antibody. An antigen may have one or more than one epitope. The specific binding referred to above is meant to indicate that the antigen will react, in a highly selective manner, with its corresponding antibody and not with the multitude of other antibodies which may be evoked by other antigens. An antigen according to some embodiments of the present invention is a Nectin4 protein.

The term "Nectin4" or "Nectin Cell Adhesion Molecule 4", as used herein refers to a single-pass type I membrane protein of 510 amino acids and a molecular mass of 55454 Da, also known as PVRL4; LNIR; PRR4; and EDSS1. The Nectin4 protein contains two immunoglobulin-like (Ig-like) C2-type domains and one Ig-like V-type domain. It is involved in cell adhesion through trans-homophilic and -heterophilic interactions. The soluble form is produced by proteolytic cleavage at the cell surface by the metalloproteinase ADAM17/TACE and the secreted form is found in both breast tumor cell lines and breast tumor patients. An exemplary Nectin4 according to the invention is set forth in SwissPort, UniPort and GenBank symbols or accession numbers: Q96NY8-NECT4_HUMAN; Q96NY8; B4DQW3; Q96K15; Q96NY8-1; Q96NY8-2; ENSP00000356991; NP_112178.2; XP_005245565.1; XP_011508323.1; XP_011508324.1; or XP_011508325.1.

The antibodies or a fragment thereof according to the invention binds to an epitope in Nectin4. Specifically, the antibodies bind to an epitope within the ectodomain (extracellular part) of the Nectin4 protein sequence.

The term "antigenic determinant" or "epitope" as used herein refers to the region of an antigen molecule that specifically reacts with a particular antibody. Peptide sequences derived from an epitope can be used, alone or in conjunction with a carrier moiety, applying methods known in the art, to immunize animals and to produce additional polyclonal or monoclonal antibodies. Isolated peptides derived from an epitope may be used in diagnostic methods to detect antibodies.

It should be noted that the affinity can be quantified using known methods such as, Surface Plasmon Resonance (SPR) (described in Scarano S, Mascini M, Turner A P, Minunni M. Surface plasmon resonance imaging for affinity-based biosensors. Biosens Bioelectron. 2010, 25: 957-66), and can be calculated using, e.g., a dissociation constant, Kd, such that a lower Kd reflects a higher affinity.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The antigen binding domains, Fab, include regions where the polypeptide sequence varies. The term F(ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hyper-variable domains known as complementarity determining regions (CDRs 1-3). These domains contribute specificity and affinity of the antigen-binding site.

CDR identification or determination from a given heavy or light chain variable sequence, is typically made using one of few methods known in the art. For example, such determination is made according to the Kabat (Wu T. T and Kabat E. A., *J Exp Med,* 1970; 132:211-50) and IMGT (Lefranc M-P, et al., *Dev Comp Immunol,* 2003, 27:55-77).

When the term "CDR having a sequence", or a similar term is used, it includes options wherein the CDR comprises the specified sequences and also options wherein the CDR consists of the specified sequence.

The antigen specificity of an antibody is based on the hyper variable region (HVR), namely the unique CDR sequences of both light and heavy chains that together form the antigen-binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ). Both isotypes are found in all antibody classes.

The term "antibody" is used in the broadest sense and includes monoclonal antibodies (including full length or intact monoclonal antibodies), polyclonal antibodies, multivalent antibodies, and antibody fragments long enough to exhibit the desired biological activity, namely binding to human Nectin4.

Antibody or antibodies according to the invention include intact antibodies, such as polyclonal antibodies or monoclonal antibodies (mAbs), as well as proteolytic fragments thereof, such as the Fab or F(ab')$_2$ fragments. Single chain antibodies also fall within the scope of the present invention.

Antibody Fragments

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., Proc. Natl. Acad. Sci. (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from *E. coli* and chemically coupled to form F(ab')$_2$ fragments (Carter et at, Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv). Techniques for the production of single-chain antibodies (U.S. Pat. No. 4,946,778) can be adapted to produce single-chain antibodies to Nectin4.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). Monoclonal antibodies may also be isolated from phage antibody libraries using the techniques described, for example, in Clackson et al., Nature 1991, 352, 624-628 or Marks et al., J. Mol. Biol., 1991, 222:581-597.

The design and development of recombinant monovalent antigen-binding molecules derived from monoclonal antibodies through rapid identification and cloning of the functional variable heavy (VH) and variable light (VL) genes and the design and cloning of a synthetic DNA sequence optimized for expression in recombinant bacteria are described in Fields et at. 2013, 8(6):1125-48.

The mAbs of the present invention may be of any immunoglobulin class including IgG, IgM, IgE, IgA, and IgD. A hybridoma producing a mAb may be cultivated in-vitro or in-vivo. High titers of mAbs can be obtained by in-vivo production where cells from the individual hybridomas are injected intra-peritoneally into pristine-primed Balb/c mice to produce ascites fluid containing high concentrations of the desired mAbs. mAbs may be purified from such ascites fluids, or from culture supernatants, using methods well known to those of skill in the art.

Anti-idiotype antibodies specifically immunoreactive with the hypervariable regions of an antibody of the invention are also comprehended.

The invention provides a monoclonal antibody or an antibody fragment comprising an antigen binding domain (ABD) which comprises three CDRs of a light chain and three CDRs of a heavy chain, wherein said ABD has at least 90% sequence identity or similarity with an ABD of a monoclonal mouse antibody comprising: (i) a heavy variable chain comprising the amino acid sequence SEQ ID NO: 39 and a light variable chain comprising the amino acid sequence SEQ ID NO: 40 (herein identified as hNec4.11); (i) a heavy variable chain comprising the amino acid sequence SEQ ID NO: 35 and a light variable chain comprising the amino acid sequence SEQ ID NO: 36 (herein identified as hNec4.01); or (ii) a heavy variable chain comprising the amino acid sequence SEQ ID NO: 37 and a light variable chain comprising the amino acid sequence SEQ ID NO: 38 (herein identified as hNec4.05). Such antibody may have an ABD domain having at least 93%, at least 94%, at least 95%, at least 96, at least 97, at least 98, at least 99% sequence identity or similarity or 100% sequence identity with corresponding ABD of antibodies hNec4.11, hNec4.01 or hNec4.05.

Sequence identity is the amount of amino acids or nucleotides which match exactly between two different sequences. Sequence similarity permits conservative substitution of amino acids to be determined as identical amino acids.

The invention also provides conservative amino acid variants of the antibody molecules according to the invention. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved. The term "antibody analog" as used herein refers to an antibody derived from another antibody by one or more conservative amino acid substitutions.

The term "antibody variant" as used herein refers to any molecule comprising the antibody of the present invention. For example, fusion proteins in which the antibody or an antigen-binding-fragment thereof is linked to another chemical entity is considered an antibody variant.

Analogs and variants of the antibody sequences are also within the scope of the present application. These include, but are not limited to, conservative and non-conservative substitution, insertion and deletion of amino acids within the sequence. Such modification and the resultant antibody analog or variant are within the scope of the present invention as long as they confer, or even improve the binding of the antibody to the human Nectin4.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration, and targeting to specific cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, according to one table known in the art, the following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It should be emphasized that the variant chain sequences are determined by sequencing methods using specific primers. Different sequencing methods employed on the same sequence may result in slightly different sequences due to technical issues and different primers, particularly in the sequence terminals Therefore, different variants of the anti-Nectin4 variable chain sequences are specified along the application.

The terms "molecule having the antigen-binding portion of an antibody" and "antigen-binding-fragments" as used herein are intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see e.g., WO 93/15210, U.S. patent application Ser. No. 08/256,790, WO 96/13583, U.S. patent application Ser. No. 08/817,788, WO 96/37621, U.S. patent application Ser. No. 08/999,554), and single-chain antibodies incorporating such reactive fraction, as well as any other type of molecule in which such antibody reactive fraction has been physically inserted. Such molecules may be provided by any known technique, including, but not limited to, enzymatic cleavage, peptide synthesis or recombinant techniques.

The monoclonal antibodies herein specifically include "chimeric" antibodies in which a portion of the heavy and/or light chain is identical with or homologous to corresponding sequences in antibodies derived from a particular species, or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules of which different portions are derived from different animal species, such as those having a variable region derived from a murine mAb and a human immunoglobulin constant region. Antibodies that have variable region framework residues substantially from human antibody (termed an acceptor antibody) and CDRs substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

According to some specific embodiments, the monoclonal antibody is a chimeric monoclonal antibody.

According to some embodiments, the chimeric antibody comprises human-derived constant regions.

According to some embodiments the human constant regions of the chimeric antibody are selected from the group consisting of: human IgG1, human IgG2, human IgG3, and human IgG4.

According to a particular embodiment, a chimeric monoclonal antibody which recognizes human Nectin4 is provided comprising:

i. a set of six CDRs wherein: HC CDR1 is (SEQ ID NO: 25); HC CDR2 is (SEQ ID NO: 26); HC CDR3 is (SEQ ID NO: 27); LC CDR1 is (SEQ ID NO: 28); LC CDR2 is (SEQ ID NO: 29); and LC CDR3 is (SEQ ID NO: 30);

ii. a set of six CDRs wherein: HC CDR1 is (SEQ ID NO: 9); HC CDR2 is (SEQ ID NO: 10); HC CDR3 is (SEQ ID NO: 11); LC CDR1 is (SEQ ID NO: 12); LC CDR2 is (SEQ ID NO: 13); and LC CDR3 is (SEQ ID NO: 14); or iii. a set of six CDRs wherein: HC CDR1 sequence is (SEQ ID NO: 15); HC CDR2 is (SEQ ID NO: 16); HC CDR3 is (SEQ ID NO: 17); LC CDR1 is (SEQ ID NO: 18); LC CDR2 is (SEQ ID NO: 19); and LC CDR3 is (SEQ ID NO: 20).

According to an aspect, the present invention provides a CAR comprising an antibody fragment that bind specifically to Nectin4.

According to some embodiments, the CAR comprises: i) a specific binding agent that can specifically bind to nectin4; ii) a spacer or hinge domain; iii) a trans-membrane domain (TM) that anchor the CAR within the T cell membrane; iv) an endodomain which transmits signals within the T cell.

According to some embodiments, the CAR comprises a CDR set selected from the group consisting of:
i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);
ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and
iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

According to an aspect, the present invention provides an isolated nucleic acid molecule encoding a CAR comprising an antibody or antibody fragment which includes Nectin4 binding domain comprising a CDR set selected from the group consisting of:
i. a set of six CDRs wherein: HC CDR1 is SYYIH (SEQ ID NO: 25); HC CDR2 is WIYPGNVNTKYNERFKG (SEQ ID NO: 26); HC CDR3 is SNPYVMDY (SEQ ID NO: 27); LC CDR1 is KASQSVNNDVA (SEQ ID NO: 28); LC CDR2 is YASNRFT (SEQ ID NO: 29); and LC CDR3 is QQAYRSPYT (SEQ ID NO: 30);
ii. a set of six CDRs wherein: HC CDR1 is AYNIH (SEQ ID NO: 9); HC CDR2 is YIYPNNGGSGYNQKFMN (SEQ ID NO: 10); HC CDR3 is FDYDEAWFIY (SEQ ID NO: 11); LC CDR1 is SASSSVSYMH (SEQ ID NO: 12); LC CDR2 is DTSKLAS (SEQ ID NO: 13); and LC CDR3 is FQGSGSPYT (SEQ ID NO: 14); and
iii. a set of six CDRs wherein: HC CDR1 sequence is TYYIH (SEQ ID NO: 15); HC CDR2 is WIYPGNVNTKNNEKFKV (SEQ ID NO: 16); HC CDR3 is SNPYVMDY (SEQ ID NO: 17); LC CDR1 is KASQSVSNDVA (SEQ ID NO: 18); LC CDR2 is YASNRYT (SEQ ID NO: 19); and LC CDR3 is QQDYSSPYT (SEQ ID NO: 20).

According to some embodiments, a vector comprises a polynucleotide sequence set forth in SEQ ID NO: 31 or SEQ ID NO: 33 is provided. According to certain embodiments the vector is a viral vector. According to certain embodiments the viral vector is a lentiviral vector.

According to some embodiments, a T cell engineered to express the CAR described herein is provided.

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, or more amino acids of the extracellular region) and/or one or more additional amino acids associated with the intracellular region of the protein from which the transmembrane protein is derived (e.g., 1, 2, 3, 4, 5, or more amino acids of the intracellular region). According to some embodiments, the transmembrane domain can be selected or modified by amino acid substitution to avoid binding of such domains to the transmembrane domains of the same or different surface membrane proteins, e.g., to minimize interactions with other members of the receptor complex.

According to some embodiments, the trans membrane domain is a trans membrane domain of a protein selected from the group consisting of the alpha, beta or zeta chain of the T-cell receptor, CD27, CD28, CD3 epsilon, CD45, CD4, CD5, CD8, CD9, CD16, CD22, CD33, CD37, CD64, CD80, CD86, CD134, CD137 and CD154. Each possibility represents a separate embodiment of the invention.

According to some embodiments, the antibody or antibody fragment which includes Nectin4 binding domain is connected to the transmembrane domain by a hinge region. According to some embodiments, the hinge is from a human protein. According to some embodiments, the hinge is a human Ig (immunoglobulin) hinge. According to certain embodiments, the hinge is an IgG4 hinge or a CD8a hinge.

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. The term intracellular signaling domain is meant to include any truncated portion of the intracellular signaling domain sufficient to transduce the effector function signal. Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

In some embodiments, signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e g, a costimulatory domain).

According to some embodiments, the intracellular signaling domain is designed to comprise two or more, costimulatory signaling domains According to some embodiments, the two or more costimulatory signaling domains, are separated by a linker molecule. According to some embodiments, the linker molecule is a glycine residue. According to some embodiments, the linker is an alanine residue.

According to some embodiments, the CAR comprises a costimulatory domain obtained from a protein selected from the group consisting of OX40, CD2, CD27, CD28, CDS, ICAM-1, LFA-1 (CD11a/CD18), ICOS (CD278), and 4-1BB (CD137). Each possibility represents a separate embodiment of the invention.

The invention also relates to nucleic acid molecules encoding the CARs, together with vectors and host cells. The invention also relates to a (heterologous) T cell comprising a CAR of the invention, together with pharmaceutical compositions comprising such CARs together with a suitable carrier or excipient. The invention also relates to autologous T cell therapies incorporating the T cells, compositions and CARs of the invention (and corresponding medical uses).

According to some embodiments, the CAR-expressing cell described herein can further comprise a second CAR, e.g., a second CAR that includes a different antigen binding domain, e.g., to the same target (Nectin4) or a different target. According to some embodiments, when the CAR-expressing cell comprises two or more different CARs, the antigen binding domains of the different CARs can be such that the antigen binding domains do not interact with one another.

According to some embodiments, a population of cells wherein at least one cell in the population expresses a CAR having an anti-Nectin4 domain described herein, and a second cell expressing another agent, e.g., an agent which enhances the activity of a CAR-expressing cell, is provided.

The invention also relates to a (heterologous) NK cell comprising a CAR of the invention, together with pharmaceutical compositions comprising such CARs together with a suitable carrier or excipient. The invention also relates to autologous NK cell therapies incorporating the NK cells, compositions and CARs of the invention (and corresponding medical uses).

As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell or NK-cell signaling and/or T-cell or NK-cell activation domain CARs have the ability to redirect T-cell or NK-cell specificity and reactivity toward a selected target in a non-MHC-restricted manner, exploiting the antigen-binding properties of monoclonal antibodies. The non-MHC-restricted antigen recognition gives T-cells or NK-cells expressing CARs the ability to recognize an antigen independent of antigen processing, thus bypassing a major mechanism of tumor escape. Most commonly, the CAR's extracellular binding domain is composed of a single chain variable fragment (scFv) derived from fusing the variable heavy and light regions of a murine or humanized monoclonal antibody.

Pharmacology

In pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired exposure.

Typically, the antibodies and fragments and conjugates thereof of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

The pharmaceutical composition of this invention may be administered by any suitable means, such as orally, topically, intranasally, subcutaneously, intramuscularly, intravenously, intra-arterially, intraarticulary, intralesionally, intratumorally or parenterally. Ordinarily, intravenous (i.v.) administration is used for delivering antibodies.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered, its persistence in the blood circulation, and the judgment of the treating physician.

As used herein the term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The cancer amendable for treatment by the present invention includes, but is not limited to: carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL;

mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers.

According to other embodiments, the pharmaceutical composition according to the invention are for use in treating cancer characterized by overexpression of Nectin4. Nectin4 overexpression related cancer types can be identified using known data bases such as The Cancer Genome Atlas (TCGA). According to certain embodiments, the cancer treatable with a composition according to the present invention is selected from the group consisting of adrenocortical carcinoma (ACC), chromophobe renal cell carcinoma (KICH), liver hepatocellular carcinoma (LIHC), colon and rectal adenocarcinoma (COAD, READ), pancreatic ductal adenocarcinoma (PAAD), pheochromocytoma & paraganglioma (PCPG), papillary kidney carcinoma (KIRP), lung adenocarcinoma (LUAD), head and neck squamous cell carcinoma (HNSC), prostate adenocarcinoma (PRAD), uterine corpus endometrial carcinoma (UCEC), cervical cancer (CESC), cutaneous melanoma (SKCM), mesothelioma (MESO), urothelial bladder cancer (BLCA), clear cell kidney carcinoma (KIRC), lung squamous cell carcinoma (LUSC), uterine carcinosarcoma (UCS), sarcoma (SARC), ovarian serous cystadenocarcinoma (OV), papillary thyroid carcinoma (THCA), glioblastoma multiforme (GBM), breast cancer (BRCA), lower grade glioma (LGG), and diffuse large B-cell lymphoma (DLBC). Each possibility represents a separate embodiment of the invention.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The pharmaceutical composition according to the present invention may be administered together with an anti-neoplastic composition.

The term "treatment" as used herein refers to both therapeutic treatment and prophylactic or preventative measures. Those in need of treatment include those already with the disorder as well as those in which the disorder is to be prevented.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of an antimetabolite, a mitotic inhibitor, a taxane, a topoisomerase inhibitor, a topoisomerase II inhibitor, an asparaginase, an alkylating agent, an antitumor antibiotic, and combinations thereof. Each possibility represents a separate embodiment of the invention.

According to some embodiments, the antimetabolite is selected from the group consisting of cytarabine, gludarabine, fluorouracil, mercaptopurine, methotrexate, thioguanine, gemcitabine, and hydroxyurea. According to some embodiments, the mitotic inhibitor is selected from the group consisting of vincristine, vinblastine, and vinorelbine. According to some embodiments, the topoisomerase inhibitor is selected from the group consisting of topotecan and irenotecan. According to some embodiments, the alkylating agent is selected from the group consisting of busulfan, carmustine, lomustine, chlorambucil, cyclophosphamide, cisplatin, carboplatin, ifosamide, mechlorethamine, melphalan, thiotepa, dacarbazine, and procarbazine. According to some embodiments, the antitumor antibiotic is selected from the group consisting of bleomycin, dactinomycin, daunorubicin, doxorubicin, idarubicin, mitomycin, mitoxantrone, and plicamycin. According to some embodiments, the topoisomerase II is selected from the group consisting of etoposide and teniposide. Each possibility represents a separate embodiment of the present invention.

According to some particular embodiments, the additional anti-cancer agent is selected from the group consisting of bevacizumab, carboplatin, cyclophosphamide, doxorubicin hydrochloride, gemcitabine hydrochloride, topotecan hydrochloride, thiotepa, and combinations thereof. Each possibility represents a separate embodiment of the present invention.

Monoclonal antibodies according to the present invention may be used as part of combined therapy with at least one anti-cancer agent. According to some embodiments, the additional anti-cancer agent is an immuno-modulator, an activated lymphocyte cell, a kinase inhibitor or a chemotherapeutic agent.

According to some embodiments, the anti-cancer agent is an immuno-modulator, whether agonist or antagonist, such as antibody against an immune checkpoint molecule.

Checkpoint immunotherapy blockade has proven to be an exciting new venue of cancer treatment Immune checkpoint pathways consist of a range of co-stimulatory and inhibitory molecules which work in concert in order to maintain self-tolerance and protect tissues from damage by the immune system under physiological conditions. Tumors take advantage of certain checkpoint pathways in order to evade the immune system. Therefore, the inhibition of such pathways has emerged as a promising anti-cancer treatment strategy.

The anti-cytotoxic T lymphocyte 4 (CTLA-4) antibody ipilimumab (approved in 2011) was the first immunotherapeutic agent that showed a benefit for the treatment of cancer patients. The antibody interferes with inhibitory signals during antigen presentation to T cells. Anti-programmed cell death 1 (PD-1) antibody pembrolizumab (approved in 2014) blocks negative immune regulatory signaling of the PD-1 receptor expressed by T cells. An additional anti-PD-1 agent was filed for regulatory approval in 2014 for the treatment of non-small cell lung cancer (NSCLC). Active research is currently exploring many other immune checkpoints, among them: CEACAM1, NKG2A, B7-H3, B7-H4, VISTA, CD112R, lymphocyte activation gene 3 (LAG3), CD137, OX40 (also referred to as CD134), and killer cell immunoglobulin-like receptors (KIR).

According to some specific embodiments, the immuno-modulator is selected from the group consisting of: an antibody inhibiting CTLA-4, an anti-human programmed cell death protein 1 (PD-1), PD-L1 and PD-L2 antibody, an activated cytotoxic lymphocyte cell, a lymphocyte activating agent, an antibody against CEACAM, an antibody against TIGIT, and a RAF/MEK pathway inhibitor. Each possibility represents a separate embodiment of the present invention. According to some specific embodiments, the additional immuno-modulator is selected from mAb to PD-1, mAb to PD-L1, mAb to PD-L2, mAb to CEACAM1, mAb to CTLA-4, mAB to TIGIT, PVR, Interleukin 2 (IL-2) or lymphokine-activated killer (LAK) cell.

According to other embodiments the additional anti-cancer agent is a chemotherapeutic agent. The chemotherapy agent, which could be administered together with the antibody according to the present invention, or separately, may comprise any such agent known in the art exhibiting anticancer activity, including but not limited to: mitoxantrone, topoisomerase inhibitors, spindle poison vincas: vinblastine, vincristine, vinorelbine (taxol), paclitaxel, docetaxel; alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan, dacarbazin; antibiotics: doxorubicin (adriamycin), bleomycin, mitomycin; nitrosoureas: carmustine (BCNU), lomustine, epirubicin, idarubicin, daunorubicin; inorganic ions: cisplatin, carboplatin; interferon, asparaginase; hormones: tamoxifen, leuprolide, flutamide, and megestrol acetate.

According to some embodiments, the chemotherapeutic agent is selected from alkylating agents, antimetabolites, folic acid analogs, pyrimidine analogs, purine analogs and related inhibitors, vinca alkaloids, epipodophyllotoxins, antibiotics, L-asparaginase, topoisomerase inhibitor, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. According to another embodiment, the chemotherapeutic agent is selected from the group consisting of 5-fluorouracil (5-FU), leucovorin (LV), irenotecan, oxaliplatin, capecitabine, paclitaxel and doxetaxel. One or more chemotherapeutic agents can be used.

In some embodiments, the pharmaceutical composition according to the present invention is for use in treating cancer or for use in enhancing the immune response.

The term "enhancing immune response" refers to increasing the responsiveness of the immune system and inducing or prolonging its memory. The pharmaceutical composition according to the present invention may be used to stimulate immune system upon vaccination. Thus, in one embodiment the pharmaceutical composition can be used for improving vaccination.

In certain embodiments, the cancer is selected from lung, thyroid, breast, colon, melanoma, prostate, hepatic, bladder, renal, cervical, pancreatic, leukemia, lymphoma, myeloid, ovarian, uterus, sarcoma, biliary, and endometrial cells cancer. Each possibility represents a separate embodiment of the invention.

According to some embodiments, a pharmaceutical composition, comprising at least one antibody or fragment thereof according to the present invention, and a pharmaceutical composition, comprising an additional immuno-modulator or a kinase inhibitor, are used in treatment of cancer by separate administration.

According to still another aspect the present invention provides a method of treating cancer in a subject in need thereof comprising administering to said subject a therapeutically effective amount of a monoclonal antibody or antibody fragment according to the present invention.

According to an additional aspect the present invention provides methods for treating a disease associated with Nectin4 overexpression.

According to an aspect, the present invention provides a method of treating cancer in a subject in need thereof comprising administering to said subject a therapeutically effective amount of a plurality of T-cells comprising a CAR molecule as described herein.

The term "effective amount" as used herein refers to a sufficient amount of the monoclonal antibody of the antibody fragment that, when administered to a subject will have the intended therapeutic effect. The effective amount required to achieve the therapeutic end result may depend on a number of factors including, for example, the specific type of the tumor and the severity of the patient's condition, and whether the combination is further co-administered with radiation. The effective amount (dose) of the active agents, in the context of the present invention should be sufficient to affect a beneficial therapeutic response in the subject over time, including but not limited to inhibition of tumor growth, reduction in the rate of tumor growth, prevention of tumor and metastasis growth and enhanced survival.

Toxicity and therapeutic efficacy of the compositions described herein can be determined by standard pharmaceutical procedures in cell cultures or experimental animals, e.g., by determining the IC50 (the concentration which provides 50% inhibition) and the maximal tolerated dose for a subject compound. The data obtained from these cell culture assays and animal studies can be used in formulating a range of dosages for use in humans. The dosage may vary depending inter alia upon the dosage form employed, the dosing regimen chosen, the composition of the agents used for the treatment and the route of administration utilized, among other relevant factors. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is affected or diminution of the disease state is achieved. The amount of a composition to be administered will, of course, be dependent on the subject being treated, the severity of the affliction, the manner of administration, the judgment of the prescribing physician, and all other relevant factors.

The term "administering" or "administration of" a substance, a compound or an agent to a subject can be carried out using one of a variety of methods known to those skilled in the art. For example, a compound or an agent can be administered enterally or parenterally, Enterally refers to administration via the gastrointestinal tract including per us, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent.

Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric antibodies are expected to have circulatory half-lives of up to 14-21 days. In some cases, it may be advantageous to administer a large loading dose followed by periodic (e.g., weekly) maintenance doses over the treatment period. Antibodies can also be delivered by slow-release delivery systems, pumps, and other known delivery systems for continuous infusion.

The term "about" means that an acceptable error range, e.g., up to 5% or 10%, for the particular value should be assumed.

Diagnosis

The present invention further discloses methods for diagnosing and prognosing cancer.

According to an aspect, the present invention provides a diagnostic and/or prognostic method of cancer or infectious disease in a subject, the method comprises the step of determining the expression level of Nectin4 in a biological sample of said subject using at least one antibody as described herein.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilisation, or enrichment for certain components.

Determining the expression level of Nectin4 can be performed by a labeled anti-Nectin4 antibody as described herein. Determining the expression can be performed, for example, by ELISA. The method of the invention can further comprise the step of comparing said level of expression to a control level.

The following examples are presented in order to more fully illustrate some embodiments of the invention. They should, in no way be construed as limiting the scope of the invention.

EXAMPLES

Experimental Procedures

Reference is now made to the following examples, which together with the above descriptions, illustrate the invention in a non-limiting fashion.

Generally, the nomenclature used herein and the laboratory procedures utilized in the present invention include molecular, biochemical, microbiological, immunological and recombinant DNA techniques. Such techniques are well known in the art. Other general references referring to well-known procedures are provided throughout this document for the convenience of the reader.

Methods

Cell Lines

The cell lines used were LNCap, JEG3, MCF-7, RAJI, MDA-MD-453, HT1376 and CHO cells. In some cases, CHO cells were stably transfected with cynomolgus (Cyno) or murine Nectin-4. The cells were grown at 37° C., >95% humidity and 5% $CO_2$ in DMEM for all cells except RAJI cells, which were cultured in RPMI supplemented with 10% heat inactivated FCS (media and sera from Sigma-Aldrich).

Flow Cytometry

Flow cytometry was performed using anti murine Nectin4 mAb (Clone 356704). Cells were incubated on ice for 30 minutes with 0.2 µg of mAb per 100,000 cells. Detection was performed with a secondary goat Ab coupled to AlexaFluor 647 (Jackson ImmunoResearch) for 30 min on ice.

In some cases, anti-Nectin-4 Abs were used at various concentrations and incubated on ice with target cells for 30 minutes. Detection was performed with secondary Abs directed against murine or human Fc, coupled to AlexaFluor 647 (Jackson ImmunoResearch) for 30 min on ice.

For staining of human TIGIT-Ig or human Nectin1-Ig, cells were incubated on ice for 1 hour with 3 µg of TIGIT-Ig per 100,000 cells. Detection was performed with a secondary Alexa Fluor 647 anti-human (Jackson ImmunoResearch) for 30 min on ice. For blocking experiments cells were pre-incubated with 1 µg of the indicated antibody prior to the TIGIT-Ig or human Nectin1-Ig staining. In some cases, cells were incubated with 8 ug/ml of the indicated Ab together with human TIGIT-Ig or human Nectin-1-Ig (at 20 ug/ml). Detection of ligand binding was performed with a secondary Alexa Fluor 647 anti-human Ab (Jackson ImmunoResearch).

Analysis was performed using the FACS-Calibur (BD Biosciences) or Cytoflex Becman Coulter flow cytometers and FCS express software.

Killing Assay

For evaluation of NK cell cytotoxic activity against targets cells, $S^{35}$ release assays were performed as described (Mandelboim et al., Exp. Med. 184(3):913-22). NK cells were isolated from healthy donors using EasySep human NK separation kit (19055 STEMCELL TECHNOLOGIES) and were grown with PHA and IL-2. Target cells were incubated overnight in methionine free medium with radioactive methionine [$S^{35}$]. Next, the cells were washed and incubated on ice with 1 µg of the antibodies per 5000 cells per well. The cells were then incubated with the NK cells for 5 hours. $S^{35}$ release was measured with β-counter TopCount (Packard). The results are represented as: (CPM(sample)–CPM(spontaneous release))/(CPM(total release)–CPM(spontaneous release))×100, wherein CPM denotes counts per minute.

ADCC Assay

NK cells were isolated from healthy donors using Easy-Sep human NK separation kit (19055 STEMCELL TECHNOLOGIES) and were grown with PHA and IL-2. Target cells were plated at $2.5*10^4$ cells per well in 96U plates and co-incubated with activated NK cells at E:T ratio of 2:1. Incubation was done in the presence of 12 ug/ml chimeric clones hNec4.05hIgG1 and hNec4.11hIgG1 or a control hIgG1. After two hours NK cells were analyzed by FACS for their CD107a (Biolegend cat 328619) degranulation marker expression.

CAR-T Generation and Functional Assay

Figure 11A:
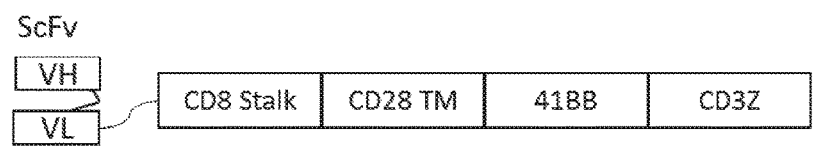
FIGS. 11A-11D CAR-T driven by hNec4.11 leads to specific T cell activation in the presence of tumor cells that express Nectin-4. (A) Schematic drawing of the CART construct. (B) Jurkat cells were transduced by lenti particles encoding for the construct and GFP. The transduction efficacy was above 99% as judged by FACS analysis of GFP expression. (C) Parental Jurkat cells or Jurkat cells expressing the CART construct (Jurkat pHAGE2.4.11) were incubated with the target cells HT1376 or MDA-MD-453 (MDA-453) for 48 hours after which media was collected and tested for IL-2 concentration as a way to assess Jurkat activation. The secretion of IL-2 was significantly induced by the CART expression (*=0.003, =0.00014; two tailed student test). Shown is a representative experiment of the two performed. (D) PBMCs from healthy donor were transduced using the CART construct. The CART PBMCs were incubated with HT1376 cells through a range of E:Ts (indicated at the X axis). Killing of the target cells was significant where marked by asterisk (*p<7*10$^{-5}$).
Figure 11B:
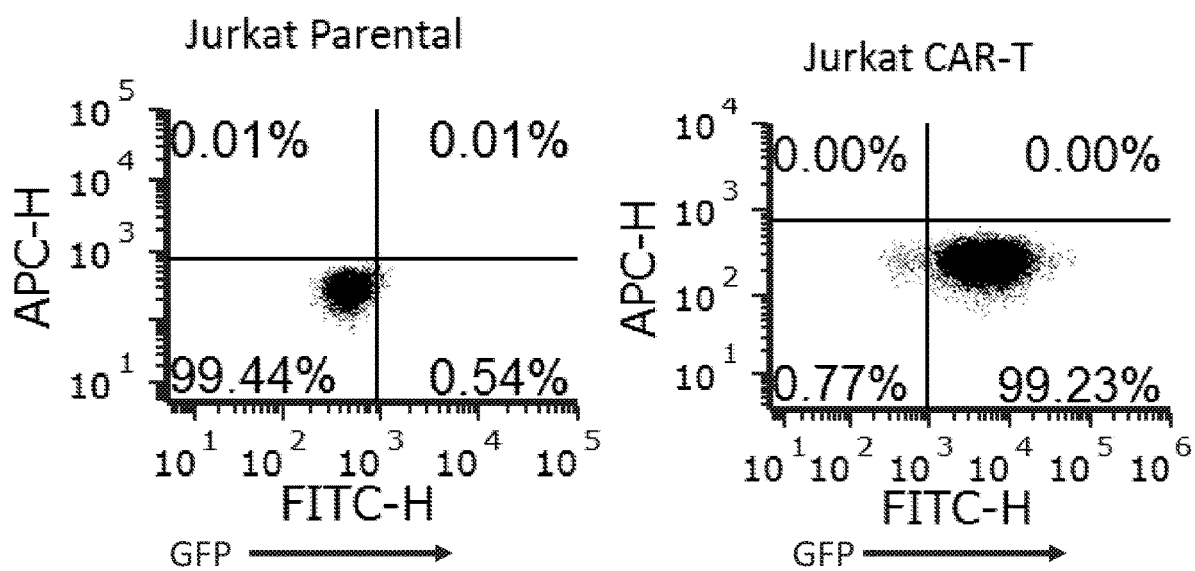

Single chain of the hNec4.11 Ab was cloned in-frame to the CD8 stalk region followed by the CD28 TM domain, 41BB intracellular domain, and the intracellular domain of CD3Zeta chain. A schematic drawing of the CAR-T construct is shown in FIG. 11A. The construct was introduced into a hEf1a containing promoter lentiviral vector (pHAGE2) followed by IRES GFP cassette to monitor transduction efficacy. Jurkat cells were transduced by lenti particles encoding for the construct. The transduction efficacy was above 99% (FIG. 11B).

Parental Jurkat cells or Jurkat cells expressing the CAR-T construct (Jurkat pHAGE2.4.11) ($5*10^4$ per well) were incubated with the target cells HT1376 and MDA-MD-453 at E:T ratio of 1:1 for 48 hours. Sups were collected after centrifugation and IL-2 levels were measured using the IL-2 ELISA kit of Peprotech (cat 900-T12) according to the manufacturer protocol.

PBMCs from healthy donor were preactivated for 72 hours, using ImmunoCult™ Human CD3/CD28 T Cell Activator according to the manufacturer protocol. The cells were transduced using pHAGE2.4.11 lenti according to Kochenderfer J N et al. (J Immunother. 2009 doi: 10.1097/CJI.0b013e3181ac6138) and the expression was validated by GFP levels. The CART PBMCs were incubated with HT1376 ($2.5*10^4$/well) cells through a range of E:Ts. After 48 hours the effector cells were removed, the target cells were washed three times and viability measured using CellTiter-Glo® Luminescent Cell Viability Assay according to the manufacturer protocol.

In Vivo Mice Tumor Model

All experiments were performed using 6-8 weeks old SCID-beige female mice. All mice were housed under SPF conditions, normal light/dark cycles and 22+/−2° C. in a specific pathogen free unit of the Hebrew University Medical School (Ein-Kerem, Jerusalem) and in accordance with the guidelines of the ethics committee. Every group of mice contained 7 females (n=7). Xenografts were generated by administering subcutaneous injection of the indicated cells into the left flank region. Injection of anti Nectin4 clone.05 and control (anti-murine CD3, InVivoMAb-clone 17A2) antibodies was administrated intraperitoneally twice a week. The mice were monitored daily. On the day of assay termination (see figure legends) all mice were sacrificed and individual tumor weights were recorded. No differences were observed between the various mice groups in their general health at baseline.

Example 1. Generation and Selection of Anti-Nectin-4 mAbs

The immunogen (Nec4-Fc) expression technology is based on mammalian HEK 293T cells, a method of choice especially in the case of glycoproteins that gives the best quality, stability, solubility and yield. Nec4-Fc protein which is a fusion protein of the ectodomain of Nectin-4 and human IgG1 Fc domain was produces recombinantly and purified as following:

The coding sequence of human Nectin4 was cloned as a fusion to the Fc fragment of human IgG1 to generate the recombinant Fc-fusion protein. The ectodomain (extracellular) part of the human Nectin4 molecule, spanning residues 32 to 349 was used. C-terminal Serine residue at position 349 of the Nectin4 amino acid sequence was fused to the heavy chain hinge of a deglycosyltaed Fc (N297A) of human IgG1, followed by the CH2 and CH3 constant regions. The open reading frame (ORF) of the recombinant protein was codon optimized for high-level expression in mammalian cells. The optimized DNA sequence was produced by GeneArt synthesis service (Invitrogen) with the addition of flanking DNA sequences corresponding to EcoRI and NotI restriction sites at the 5' and 3' ends of the DNA fragment, respectively. The expression vector was constructed by double digestion of the optimized DNA fragment with EcoRI and NotI, followed by its ligation into pIRE-Spuro3 (Clontech Laboratories, Inc.). The resulting constructs were transfected into HEK-293T cells by using the FuGENE 6 Transfection Reagent (Roche Diagnostics). After 48 h, transfected cells were subjected to antibiotic selection with 5 g/mL puromycin (Sigma-Aldrich). Stable pools were analyzed for protein secretion by SDS/PAGE. Supernatants were collected and purified on a Poros 20 protein G column in the High-Pressure Perfusion Chromatography Station, BioCAD (PerSeptive Biosystems). The resulted fusion protein immunogen is denoted Nectin4-Fc.

For immunization, BALB/c mice were injected with 50 μg of the immunogen in complete Freund's adjuvant (CFA) followed by 50 μg of the immunogen in incomplete Freund's adjuvant (IFA) at day 14 post first immunization. Next, the sera were analyzed for anti-Nec-4-Fc antibody titer by ELISA. The mice with the highest titer were boosted with the 50 μg of the immunogen in PBS. After three days, the spleen of immune mice was taken and, after lysis of red blood cells, the splenocytes were fused with SP2/0 cell line. The potential hybridoma cells were seeded in 20% RPMI 1640 medium containing hypoxanthine, aminopterin, and thymidine (HAT) for selection of stable hybridoma cell lines. The abovementioned procedure was repeated twice and in total, 1034 wells were screened for anti-Nec4-Fc antibody secretion by ELISA. Next, 30 wells that their supernatant where positive for binding to Nec4-Fc coated on ELISA plates, were retested for their positivity, and in parallel a cross-reactivity test was performed on an irrelevant Fc fusion protein. This resulted in 10 hybridoma cell lines that secreted antibodies specifically recognizing Nectin-4 ectodomain. All these candidates that showed the specific signal in ELISA were tested for their ability to recognize a native human Nectin-4 protein on transfectant cell lines.

Figure 2:
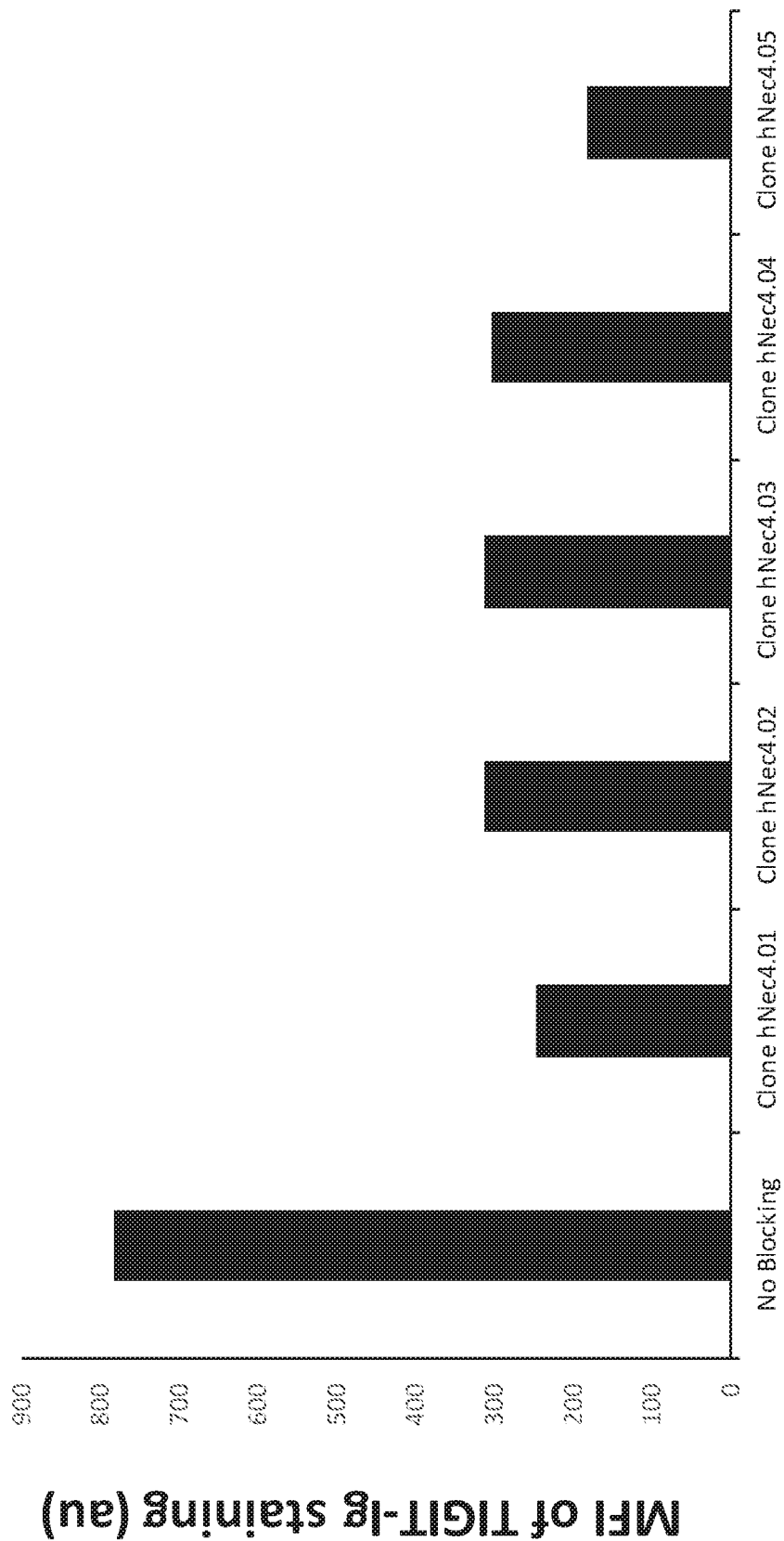
FIG. 2 Antibody clones hNec4.05 and hNec4.01 show the best blocking capability of TIGIT-Nectin4 interactions. The graph depicts the Mean Fluorescence Intensity (MFI) values of FACS staining of RAJI Burkitt's lymphoma cells transfected with Nectin4. The cells were incubated with 0.2 μg of different clones (as indicated) and then incubated with 3 μg of TIGIT-Ig followed by staining with an anti-human secondary antibody.

RAJI Burkitt's lymphoma cells were transfected with human Nectin4 and analyzed by FACS for determining the binding of the five hybridoma clones indicated. The cells were incubated with different clones and then incubated with human TIGIT-Ig and stained with a secondary antibody. The Mean Fluorescence Intensity (MFI) values of the FACS staining are depicted in FIG. 2. As shown, monoclonal antibodies produced by clones hNec4.01 (Clone 1) and hNec4.05 (Clone 5), exhibited the best blocking capability of TIGIT-Nectin4 interactions.

Similar assays, using JEG3 and LNCap cell lines that naturally expressed Nectin4 were also performed and have yielded similar results.

Five antibodies showed positive staining Out of those 5, 4 were further selected for their IgG isotype (and not IgM isotype) Finally, the 4 remaining candidates all showed a strong binding capacity to the native human Nectin-4 molecules expressed on the surface of live cells and were repetitively tested on several irrelevant fusion proteins to select for those with zero cross-reactivity between Nectin-4 and other ligands of the immune cell receptors. However, only 2 of those were shown to be blocking antibodies against Nectin-4. Thus, 2 stable clonal cell lines, hNec4.01 and hNec4.05, have been generated, both of the isotype kappa IgG1. Next, a large-scale Ab production was performed and both monoclonal antibodies were purified from the serum free medium, using GE AKTA Prime Plus Liquid Chromatography System and HiTrap Protein G columns, in an amount of few milligrams.

Similarly to the above, additional clones were identified, out of which clone 11 (hNec4.11) had the best binding and blocking capacities and thus was screened in parallel to hNec4.05 as described below.

Based on the above attempts, it was concluded that even in the case of an immunogen closely resembling the target protein Nectin-4 (in terms that it is a dimer, glycosylated by mammalian cell machinery and produced under non-denaturing conditions), the chance of obtaining a hybridoma cell line secreting blocking anti-Nectin 4 antibodies is less than 2% (per mille).

Example 2. Affinity of the Anti-Nectin-4 mAbs to Human Nectin4

Figure 3:
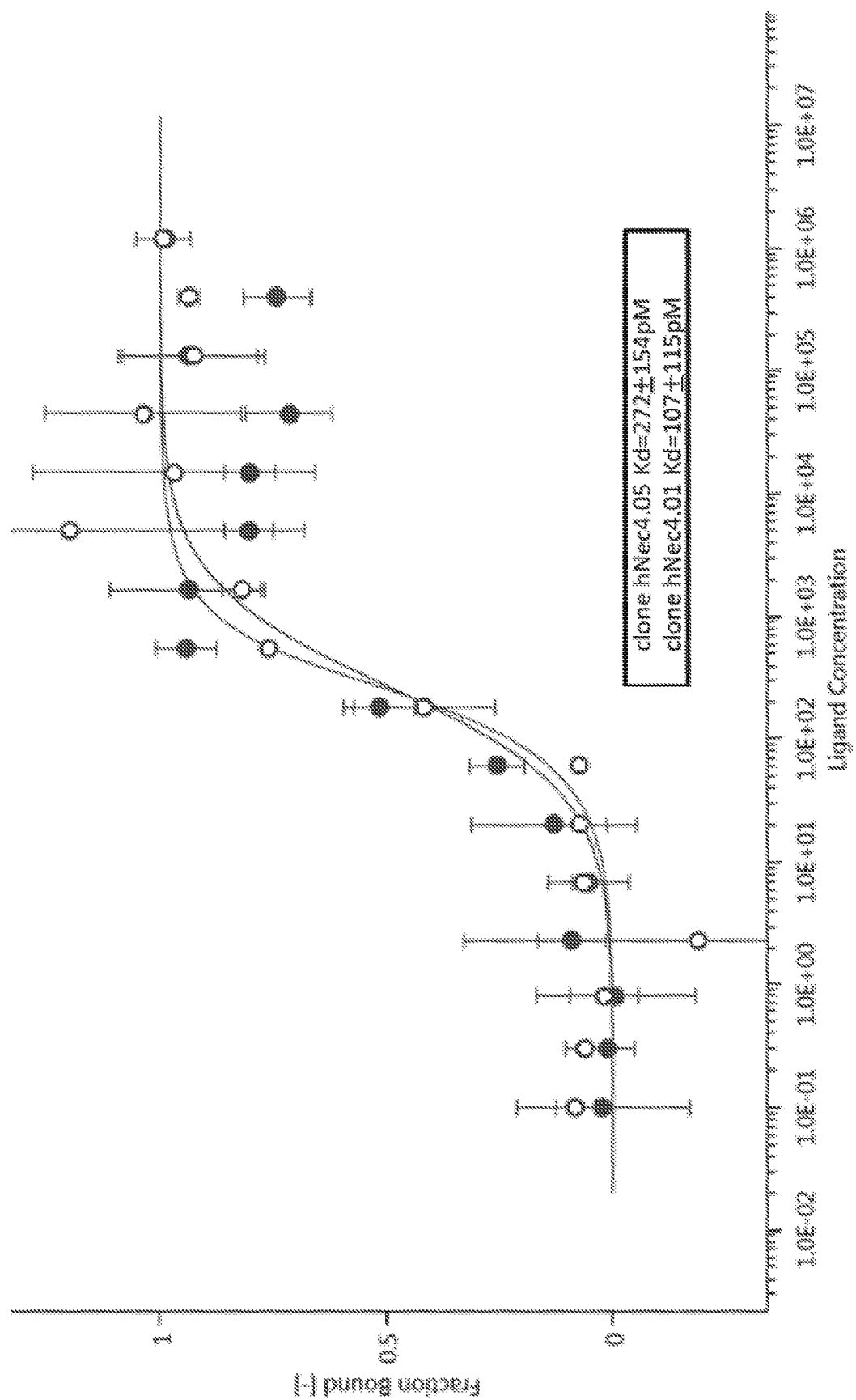
FIG. 3 Quantification of the binding affinity of antibody clones to Nectin4. The binding of fluorophore-labeled Nectin4-Ig and the antibody clones hNec4.05 and clone hNec4.01 observed with microscale thermophoresis. Measurements were repeated with at least three independent protein preparations and average of results are shown (±SEM).

The affinity of antibodies hNec4.01 and hNec4.05 to fluorophore-labeled human Nectin4-Ig molecule was further determined using microscale thermophoresis assay (Wienken et al. 2010, Nat. Commun.1:100). Measurements were repeated with at least three independent protein preparations. As shown in FIG. 3, very high binding affinities were observed for both antibodies. For clone hNec4.05 the calculated Kd is 272±154 pM, and for the hNec4.01 clone the calculated Kd was 107±115 pM.

Example 3. Sequencing of the Anti-Nectin-4 mAbs

The two hybridoma clones, No. 0.1 and No. 0.5, which demonstrated the best inhibition of Nectin4-TIGIT binding, were sent for nucleotide and amino acid sequencing.
Methods Total RNA was isolated from the hybridoma cells following the technical manual of TRIzol® Reagent (Ambion, Cat. No.: 15596-026). Total RNA was then reverse transcribed into cDNA using isotype-specific anti-sense primers or universal primers following the technical manual of PrimeScript™ 1st Strand cDNA Synthesis Kit (Takara, Cat. No.: 6110A). The antibody fragments of $V_H$ and $V_L$ were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence of these clones was provided.

The following tools for sequence analysis of immunoglobulin variable regions were used:
  i. NCBI Nucleotide BLAST;
  ii. IMGT/V Quest program; and
  iii. NCBI IgBLAST.
The obtained sequences are:

```
Clone hNec4.01:
Heavy chain variable region DNA sequence, 414 base pairs (SEQ ID NO: 1):
Leader sequence-FR1-CDR1-FR2-CDR2-FR3-CDR3-FR4
ATGGGATGGAGCTGGATCTTTCTCTTCCTCCTGTCAGGAACTGCAGGCTTCCACTCTGAGGT
CCAACTTCAGCAGTCAGGACCTGAACTGGTGAAACCTGGGGCCTCAGTGAAGATTGCCTGCA
GGGCCTCTGGATACACATTCACTGCCTACAATATCCACTGGGTGAGCCAGAGACATGGAAAG
AGCCTTGAATGGATTGGATATATCTATCCTAACAATGGTGGTTCTGGCTACAACCAGAAATT
CATGAACAAGGCCACATTGACTGTAGACCATTCCTCCAATACAGCCTACATGGAGCTCCGCA
GCCTGACGTCTGAGGACTCTGCAGTCTATTACTGTGCAATATTTGATTACGACGAGGCCTGG
TTTATTTACTGGGGCCAAGGGACTCTGGTCACTGTCTCTGCA Heavy chain variable region polypeptide sequence, 138 amino acids, (SEQ ID NO: 2):
Leader sequence-FR1-CDR1-FR2-CDR2-FR3-CDR3-FR4
MGWSWIFLFLLSGTAGFHSEVQLQQSGPELVKPGASVKIACRASGYTFTAYNIHWVSQRHGK
SLEWIGYIYPNNGGSGYNQKFMNKATLTVDHSSNTAYMELRSLTSEDSAVYYCAIFDYDEAW
FIYWGQGTLVTVSA Heavy chain variable region polypeptide sequence (FR1-CDR1-FR2-CDR2-FR3-CDR3-
FR4 (SEQ ID NO: 35)
EVQLQQSGPELVKPGASVKIACRASGYTFTAYNIHWVSQRHGKSLEWIGYIYPNNGGSGYNQ
KFMNKATLTVDHSSNTAYMELRSLTSEDSAVYYCAIFDYDEAWFIYWGQGTLVTVSA Light chain variable region DNA sequence, 384 base pairs (SEQ ID NO: 3):
Leader sequence-FR1-CDR1-FR2-CDR2-FR3-CDR3-FR4
ATGGATTTTCAAGTGCAGATTTTCAGCTTCCTGCTAATCAGTGCCTCAGTCATAATGTCCAG
AGGAGAAAATGTTCTCACCCAGTCTCCAGAAATCATGTCTGCATCTCCCGGGGAAGAGGTCA
CCATGACCTGTAGTGCCAGCTCAAGTGTTAGTTACATGCACTGGTTCCAGCAGAAGTCAACT
ATCTCCCCCAAACTCTGGATTTATGACACATCCAAACTGGCTTCTGGAGTCCCCGGTCGCTT
CAGTGGCAGTGGGTCTGGCAAGTCTTACTCTCTCACGATCAGAAACATGGAGGCTGAAGATG
TTGCCACCTATTACTGTTTTCAGGGGAGTGGGAGCCCGTACACGTTCGGAGGGGGGACCAAG
CTGGAAATTAAA Light chain variable region polypeptide sequence, 128 amino acids (SEQ ID NO: 4):
Leader sequence-FR1-CDR1-FR2-CDR2-FR3-CDR3-FR4
MDFQVQIFSFLLISASVIMSRGENVLTQSPEIMSASPGEEVTMTCSASSSVSYMHWFQQKST
ISPKLWIYDTSKLASGVPGRFSGSGSGKSYSLTIRNMEAEDVATYYCFQGSGSPYTFGGGTK
LEIK
```

Light chain variable region polypeptide sequence (FR1-CDR1-FR2-CDR2-FR3-CDR3-FR4 (SEQ ID NO: 36)
ENVLTQSPEIMSASPGEEVTMTCSASSSVSYMHWFQQKSTISPKLWIYDTSKLASGVPGRFS
GSGSGKSYSLTIRNMEAEDVATYYCFQGSGSPYTFGGGTKLEIK Clone hNec4.05
Heavy chain variable region DNA sequence, 408 base pairs (SEQ ID NO: 5):
Leader sequence-FR1-CDR1-FR2-CDR2-FR3-CDR3-FR4
*ATGGGATGGAGCCGGATCTTTCTCTTCCTCCTGTCAATAATTGCAGGTGTCCATTGC*CAGGT
CCAGCTGCAGCAGTCTGGACCTGAGCTGGTGAAGCCTGGGGCTTCAGTGAGGATATCCTGCA
AGGCCTCTGGCTACACCTTCACAACCTACTATATACACTGGGTGAAGCAGAGGCCTGGACAG
GGACTTGAGTGGATTGGA**TGGATTTATCCTGGAAATGTTAATACTAAGAACAATGAGAAGTT
CAAGGTC**AAGGCCACACTGACTGCAGACAAATCCTCCAGCACAGCCTACATGCAGCTCAGCA
GCCTGACCTCTGAGGACTCTGCGGTCTATTTCTGTGCAAGA**TCGAACCCCTATGTTATGGAC
TACT**GGGGTCAGGGAACCTCAGTCACCGTCTCCTCA Heavy chain variable region polypeptide sequence, 136 amino acids (SEQ ID NO: 6):
Leader sequence-FR1-CDR1-FR2-CDR2-FR3-CDR3-FR4
*MGWSRIFLFLLSIIAGVH*CQVQLQQSGPELVKPGASVRISCKASGYTFTTYYIHWVKQRPGQ
GLEWIGWIYPGNVNTKNNEKFKVKATLTADKSSSTAYMQLSSLTSEDSAVYFCARS**NPYVMD
Y**WGQGTSVTVSS Heavy chain variable region polypeptide sequence (FR1-CDR1-FR2-CDR2-FR3-CDR3-FR4 (SEQ ID NO: 37)
QVQLQQSGPELVKPGASVRISCKASGYTFTTYYIHWVKQRPGQGLEWIGWIYPGNVNTKNNE
KFKVKATLTADKSSSTAYMQLSSLTSEDSAVYFCARSNPYVMDYWGQGTSVTVSS Light chain variable region DNA sequence, 381 base pairs (SEQ ID NO: 7):
Leader sequence-FR1-CDR1-FR2-CDR2-FR3-CDR3-FR4
*ATGAAGTCACAGACCCAGGTCTTCGTATTTCTACTGCTCTGTGTGTCTGGTGCTCATGGGAG
TATTGTGATGACCCAGACTCCCAAATTCCTGCTTGTATCAGCAGGAGACAGGGTTACCATAA*
CCTGCAAGGCCAGTCAGAGTGTGAGTAATGATGTAGCTTGGTACCAACAGAAGCCAGGGCAG
TCTCCTAAACTGCTGATATACTATGCATCCAATCGCTACACTGGAGTCCCTGATCGCTTCAC
TGGCAGTGGATATGGGACGGATTTCACTTTTCACCATCAGCGCTGTGCAGGCTGAAGACCTGG
CAGTTTATTTCTGTCAGCAGGATTATAGCTCTCCGTACACGTTCGGAGGGGGGACCAAGCTG
GAAATAAAA Light chain variable region polypeptide sequence, 127 amino acids (SEQ ID NO: 8):
Leader sequence-FR1-CDR1-FR2-CDR2-FR3-CDR3-FR4
*MKSQTQVFVFLLLCVSGAH*GSIVMTQTPKFLLVSAGDRVTITCKASQSVSNDVAWYQQKPGQ
SPKLLIYYASNRYTGVPDRFTGSGYGTDFTFTISAVQAEDLAVYFCQQDYSSPYTFGGGTKL
EIK Light chain variable region polypeptide sequence (FR1-CDR1-FR2-CDR2-FR3-CDR3-FR4 (SEQ ID NO: 38)
SIVMTQTPKFLLVSAGDRVTITCKASQSVSNDVAWYQQKPGQSPKLLIYYASNRYTGVPDRF
TGSGYGTDFTFTISAVQAEDLAVYFCQQDYSSPYTFGGGTKLEIK Clone hNec4.11
Heavy chain variable region DNA sequence, 408 base pairs (SEQ ID NO: 21):
Leader sequence-FR1-CDR1-FR2-CDR2-FR3-CDR3-FR4
*ATGGGATGGAGCCGGATCTTTCTCTTCCTCCTGTCAATAATTGCAGGTGTCCATTGC*
CAGGTCCAGCTGCAGCAGTCTGGACCTGAACTGGTGAAGCCTGAGACTTCAGTG
AAGATATCCTGCAAGGCTTCTGGCTACACCTTCACAAGTTACTATATACACTTGG
GTGAAACAGAGGCCTGGACAGGGACTTGAGTGGATTGGC**TGGATTTATCCTGG
AAATGTTAATACTAAGTATAATGAGAGGTTTAAGGGC**AAGGCCACTCTGACTG
CAGACAAATCCTCCAACACAGCCCACATGCAGCTCACCAGCCTGACCTCTGAGG
ACTCTGCGGTCTATTTCTGTGCAAGATCGAACCCCTATGTTATGGACTACTGGG
GTCAAGGAACCTCAGTCACCGTCTCCTCA Heavy chain variable region polypeptide sequence, 136 amino acids (SEQ ID NO: 22):
Leader sequence-FR1-CDR1-FR2-CDR2-FR3-CDR3-FR4
*MGWSRIFLFLLSIIAGVH*CQVQLQQSGPELVKPETSVKISCKASGYTFTSYYIHWVKQR
PGQGLEWIGWIYPGNVNTKYNERFKGKATLTADKSSNTAHMQLTSLTSEDSAVYF
CARSNPYVMDYWGQGTSVTVSS Heavy chain variable region polypeptide sequence (FR1-CDR1-FR2-CDR2-FR3-CDR3-FR4 (SEQ ID NO: 39)
QVQLQQSGPELVKPETSVKISCKASGYTFTSYYIHWVKQRPGQGLEWIGWIYPGNVN
TKYNERFKGKATLTADKSSNTAHMQLTSLTSEDSAVYFCARSNPYVMDYWGQGTS
VTVSS Light chain variable region DNA sequence, 381 base pairs (SEQ ID NO: 23):
Leader sequence-FR1-CDR1-FR2-CDR2-FR3-CDR3-FR4
*ATGAAGTCACAGACCCAGGTCTTCGTATTTCTACTGCTCTGTGTGTCTGGTGCTCATGG
GAGTATTGTGATGACCCAGACTCCCAAATTCCTGCTTGTATCAGCAGGAGACAGA*
GTCACCATAACCTGCAAGGCCAGTCAGAGTGTGAATAATGATGTGGCTTGGTA
TCAACAGAAGCCAGGGCTGTCTCCTGAACTGCTTATGTAT**TATGCATCCAATCG

```
CTTCACTGGAGTCCCTGATCGCTTCACTGGCAGTGGATATGGGACGGATTTCACT
TTCACCATCAGCTCTGTGCAGGCTGAAGACCTGGCAATTTATTTCTGTCAGCAGG
CTTATAGGTCTCCGTACACGTTCGGAGGGGGGACCAAGCTGGAAATTCAA

Light chain variable region polypeptide sequence, 127 amino acids (SEQ ID NO: 24):
Leader sequence-FR1-CDR1-FR2-CDR2-FR3-CDR3-FR4
MKSQTQVFVFLLLCVSGAHGSIVMTQTPKFLLVSAGDRVTITCKASQSVNNDVAWYQ
QKPGLSPELLMYYASNRFTGVPDRFTGSGYGTDFTFTISSVQAEDLAIYFCQQAYRS
PYTFGGGTKLEIQ Light chain variable region polypeptide sequence (FR1-CDR1-FR2-CDR2-FR3-CDR3-
FR4 (SEO ID NO: 40)
SIVMTQTPKFLLVSAGDRVTITCKASQSVNNDVAWYQQKPGLSPELLMYYASNRFT
GVPDRFTGSGYGTDFTFTISSVQAEDLAIYFCQQAYRSPYTFGGGTKLEIQ
```

Figure 4A:
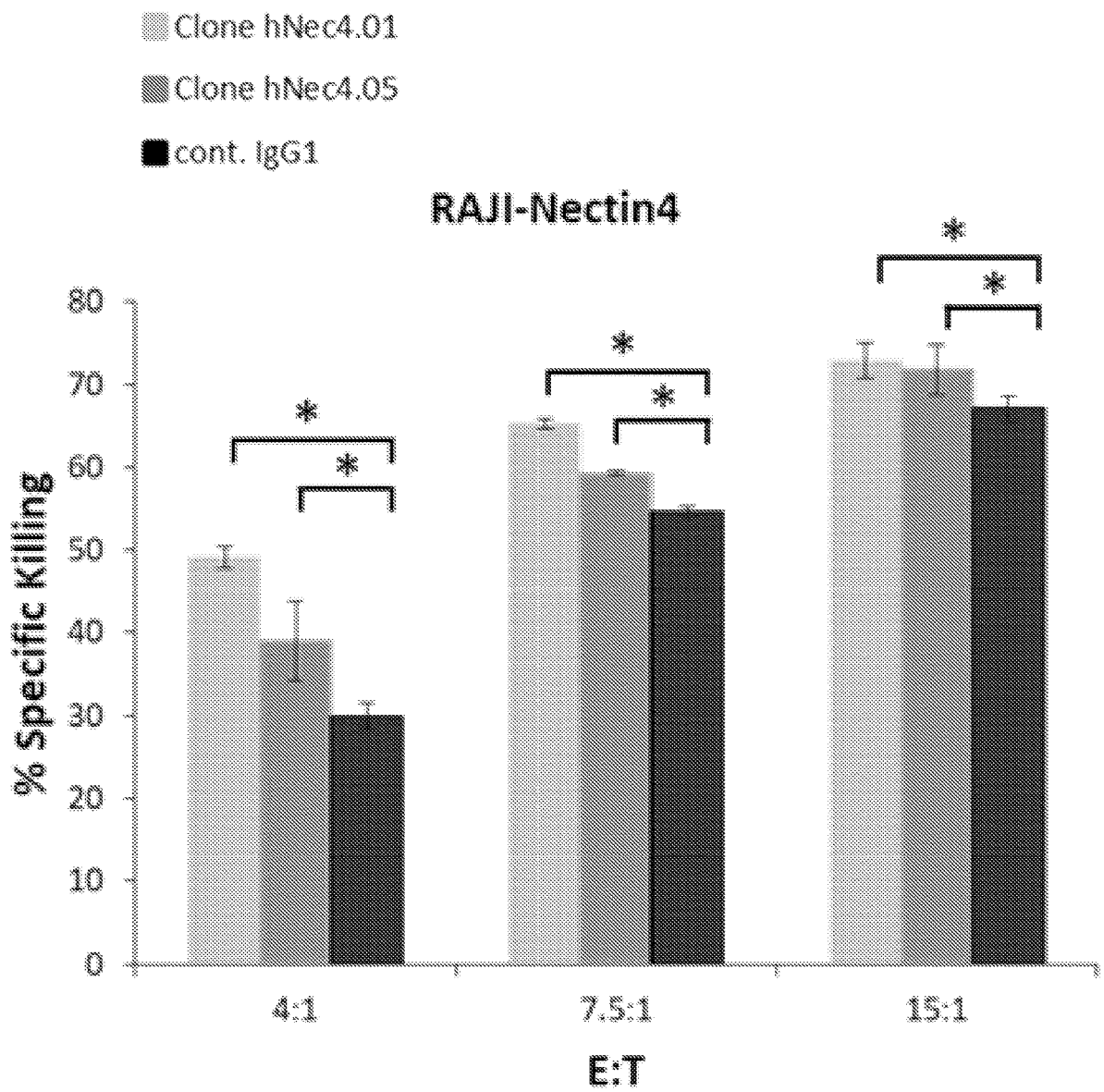
FIGS. 4A and 4B Antibody clones hNec4.05 and hNec4.01 block Nectin4 and increase NK cytotoxicity. [$^{35}$S] methionine-labelled (4A) RAJI Burkitt's lymphoma cells transfected with Nectin4 (4B) LNCap prostate carcinoma cells (naturally expressing Nectin4), were incubated with 1 μg/well of either mouse IgG1 as a control antibody, or anti-Nectin4 antibodies hNec4.01 or hNec4.05. After 1 h the cells were supplemented with NK cells and incubated for 5 hours. The average specific killing (±s.d.) in various Effector:Target (E:T) ratios of the NK:cancer cells is plotted. * indicates significant effect (p<0.05) of the hNec4.01 and hNec4.05 clones in comparison to the control antibody. Figure shows one representative experiment out of three performed. The same effect was determined with MCF-7, MDA-MB-453, SK-BR-3 and T47D cells—all breast cancer cell lines.
Figure 4B:
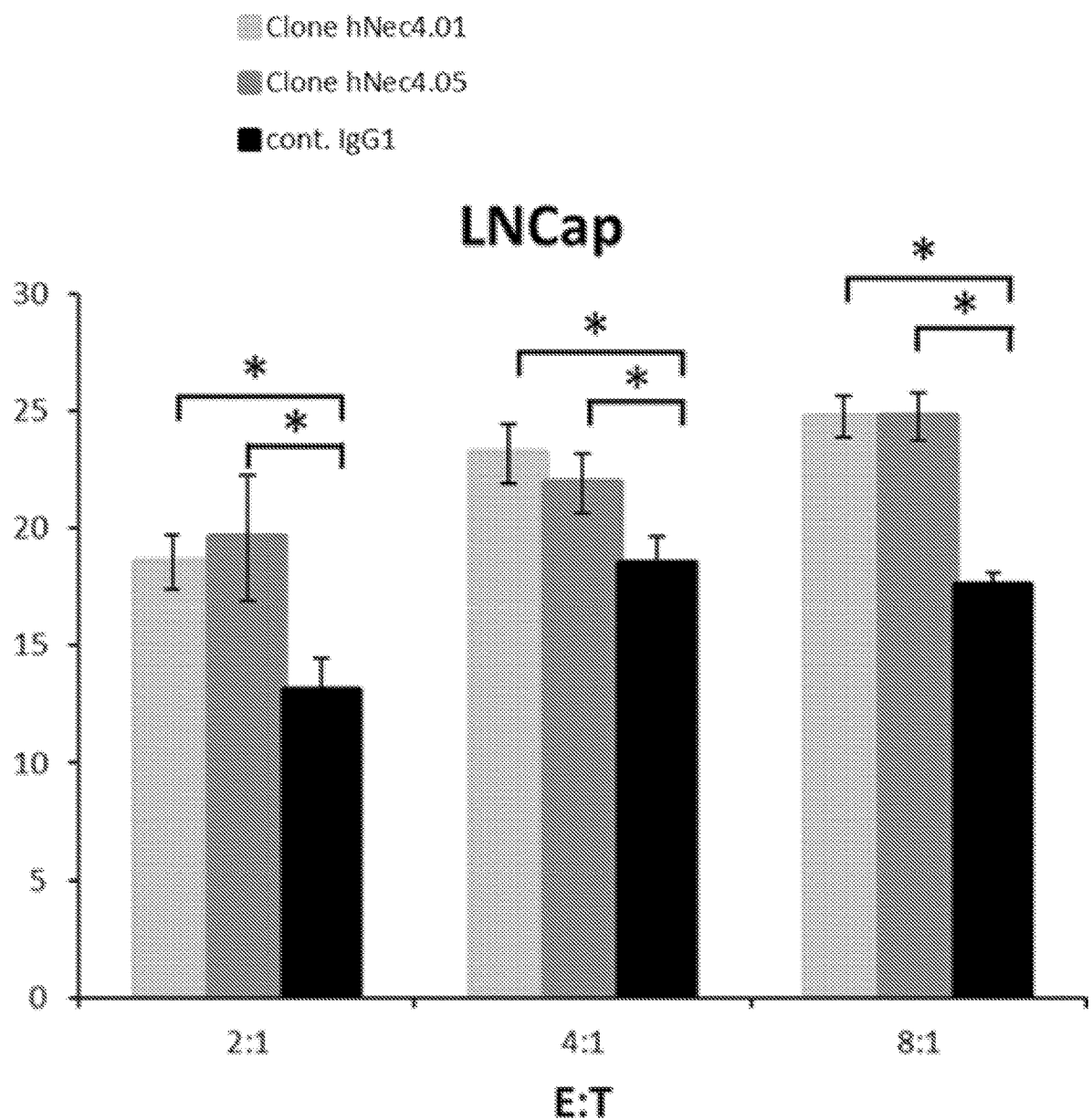

Example 4. Blocking of Nectin4-TIGIT Interactions with Anti-Nectin4 mAb Enhanced NK Cell Killing of Human Cell Lines Antibody clones hNec4.05 and hNec4.01 were tested for blocking Nectin4 binding to TIGIT and inhibiting NK cytotoxicity. [$^{35}$S] methionine-labelled RAJI Burkitt's lymphoma cells transfected with Nectin4, and LNCap prostate carcinoma cells (naturally expressing Nectin4), were incubated with 1 μg/well of either mouse IgG1 as control antibody or mouse anti human Nectin4 mAbs hNec4.01 or hNec4.05. After 1 h the cells were supplemented with NK cells and incubated for 5 hours. The average specific killing (±s.d.) in various Effector:Target (E:T) ratios of the NK:Cancer cells is plotted in FIG. 4A (RAJI cells) and FIG. 4B (LNCap cells). * indicates significant effect (p<0.05) of the hNec4.01 and hNec4.05 clones in comparison with the control antibody. Each figure shows one representative experiment out of three performed. The same effect was determined when using MCF-7-breast cancer cell line.

Example 5. Verifying the Specificity of Binding of the Anti-Nectin4 Antibodies As tested using FACS staining and demonstrated in FIGS. 5A-5C, the mAbs hNec4.01 and hNec4.05 are specific to human Nectin4 and do not bind the murine protein. RAJI cells were transfected with murine Nectin4 (black line histograms). First, RAJI cells transfected with murine Nectin4 lysates was used in Western blot assay with a commercial anti murine Nectin4 mAb (Clone 356704) in order to verify murine Nectin4 expression (A). Next, the cells were stained with 0.2 μg of (B) clone hNec4.01 or (C) clone hNec4.05. Both hNec4.01 and hNec4.05 mAbs do not show binding to murine Nectin4.

Figure 6A:
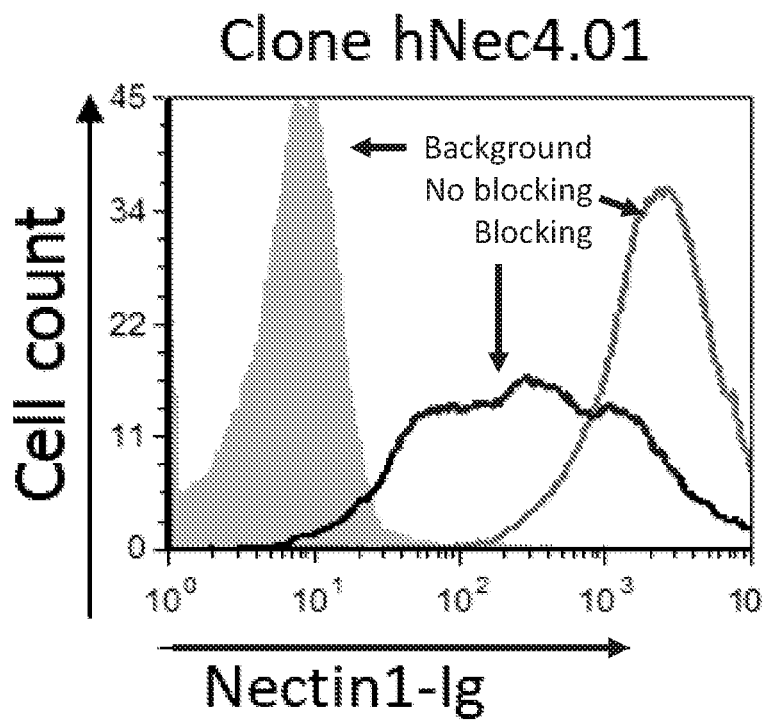
FIGS. 6A-6C Blocking of Nectin4-Nectin1 interactions. (A-B) FACS staining of RAJI cells pre-incubated with human-Nectin4. Cells were pre-incubated with 1 μg of (A) clone hNec4.01, or (B) clone hNec4.05 and then incubated with 3 μg of Nectin1-Ig (black line histograms). Staining without blocking appears as gray line. Grey filled histograms are background control staining of secondary antibody only. (C) Mean Fluorescence Intensity (MFI) values of FACS staining of A and B.
Figure 6B:
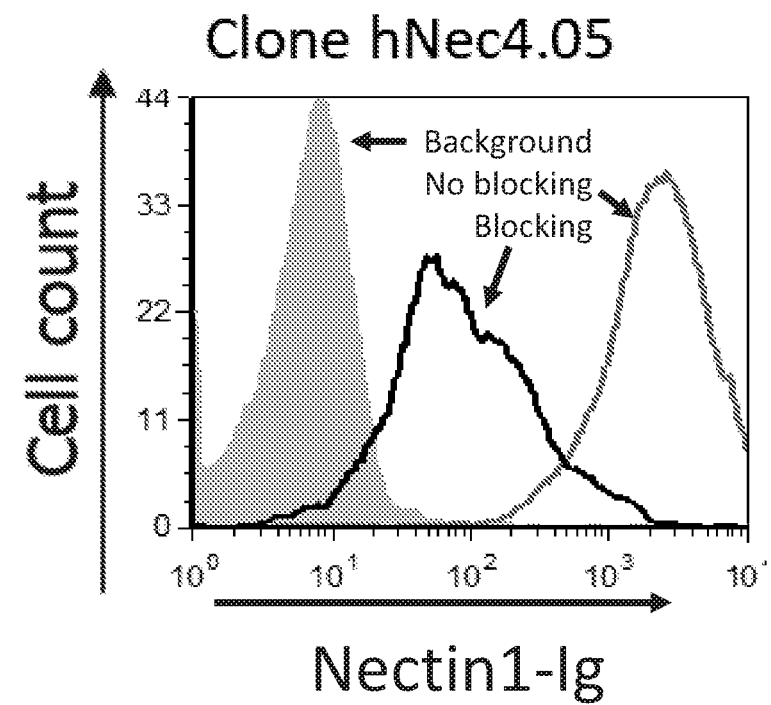
Figure 6C:
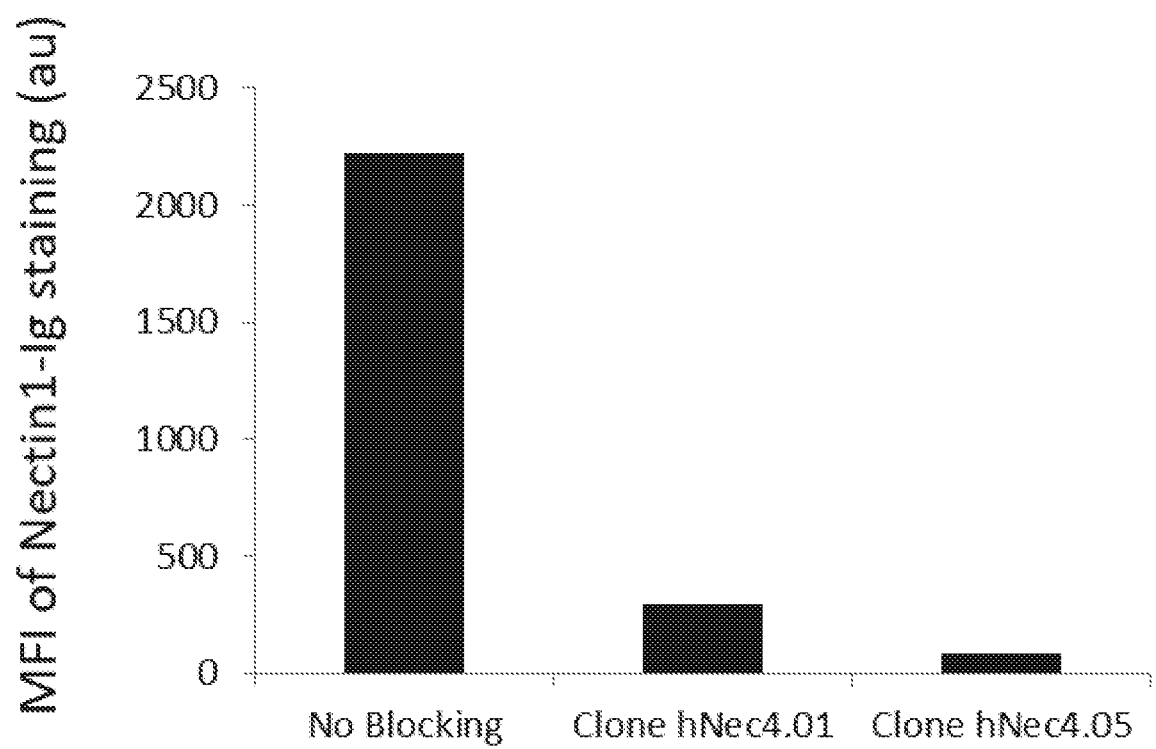

Example 6. Anti-Nectin4 Antibodies are Able to Block Nectin4-Nectin1 Interactions The ability to the anti-Nectin4 to block Nectin4-Nectin1 interactions was also determined. FACS staining of RAJI cells transfected with Nectin4 is demonstrated in FIGS. 6A-6C. Cells were Pre-incubated with 1 μg of (FIG. 6A) clone hNec4.01 or (FIG. 6B) clone hNec4.05 and then incubated with 3 μg of Nectin1-Ig (black line). Staining without blocking appears as gray line. Grey filled histograms are background control staining of secondary antibody only. It is concluded that the mAbs are able to block Nectin4-Nectin1 interaction that is suspected to increase invasiveness of tumors expressing Nectin4.

Example 7. In Vivo Models

The efficacy of the anti-Nectin4 mAbs was determined in vivo in animal models. Cell lines that naturally (MDA-MB-453) or recombinantly (Raji Nectin4 OE) express Nectin4 were injected SC to mice (5×10$^6$ cells per mouse). SCID beige mice, which lack NK, B and T cells were used. In order to study NK cell contribution to tumor cell growth in these models human NK cells at 1×10$^6$ were co injected with the tumor cells in some of the treatment groups.

Figure 7A:
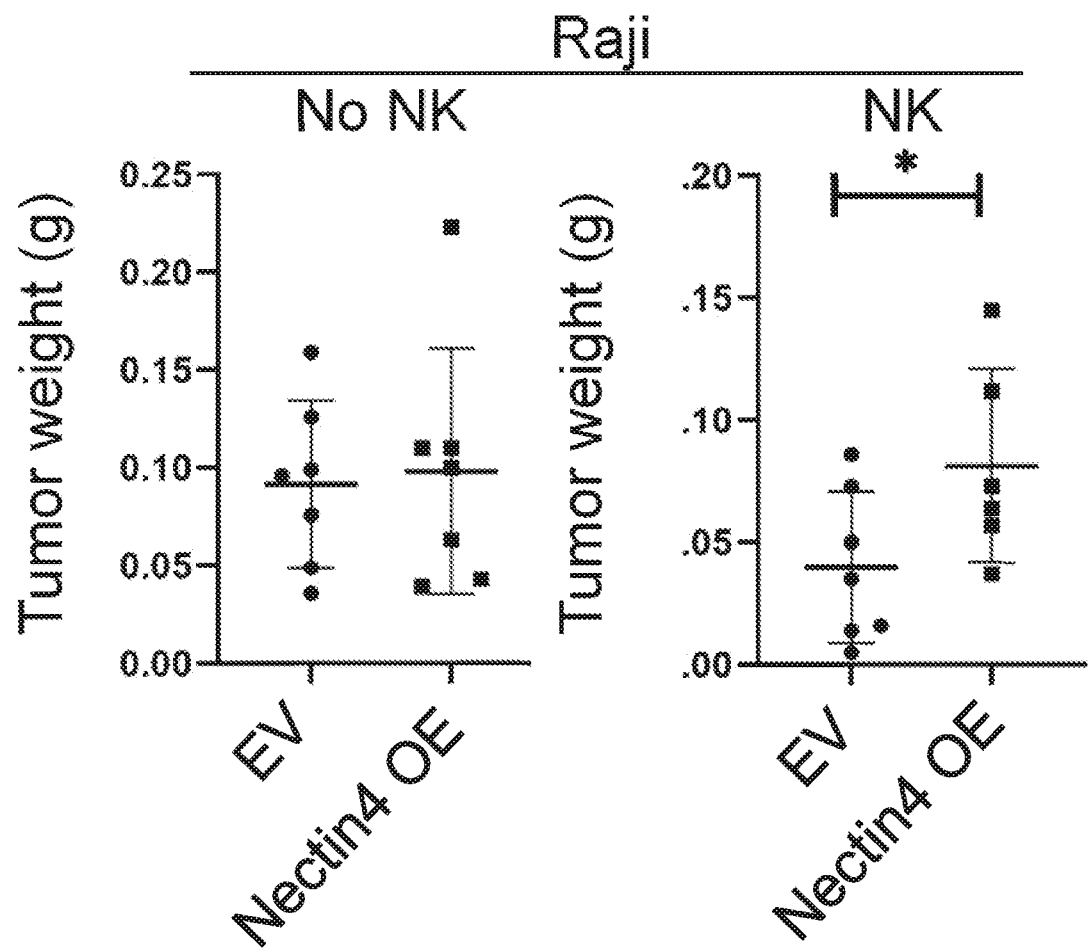
FIGS. 7A-7C In vivo effect of anti-Nectin4 mAb. (A) SCID-beige mice were subcutaneously implanted with 5×10$^6$ Raji cells that were either transfected with empty vector (EV) or over expressed (OE) nectin4, alone (left panel, no NK) or together with 1×10$^6$ NK cells (right panel, NK). (B) SCID-beige mice were subcutaneously implanted with 5×10$^6$ Raji cells over expressing nectin4 together with either 1×10$^6$ NK cells. Mice were treated with 75 ug of either a control Ab or with anti Nectin4 clone hNec4.05 mAb, twice a week by intraperitoneal injection. (C) SCID-beige mice were subcutaneously implanted with 5×10$^6$ MDA-MB-453 cells, alone or with 7×10$^5$ NK cells. Mice were then treated as in (B). Tumors were harvested and weighed at day 21 (A), 27 (B), or 23 (C) post tumor injection. N=7 for all mice experimental groups. (*) p<0.05.
Figure 7B:
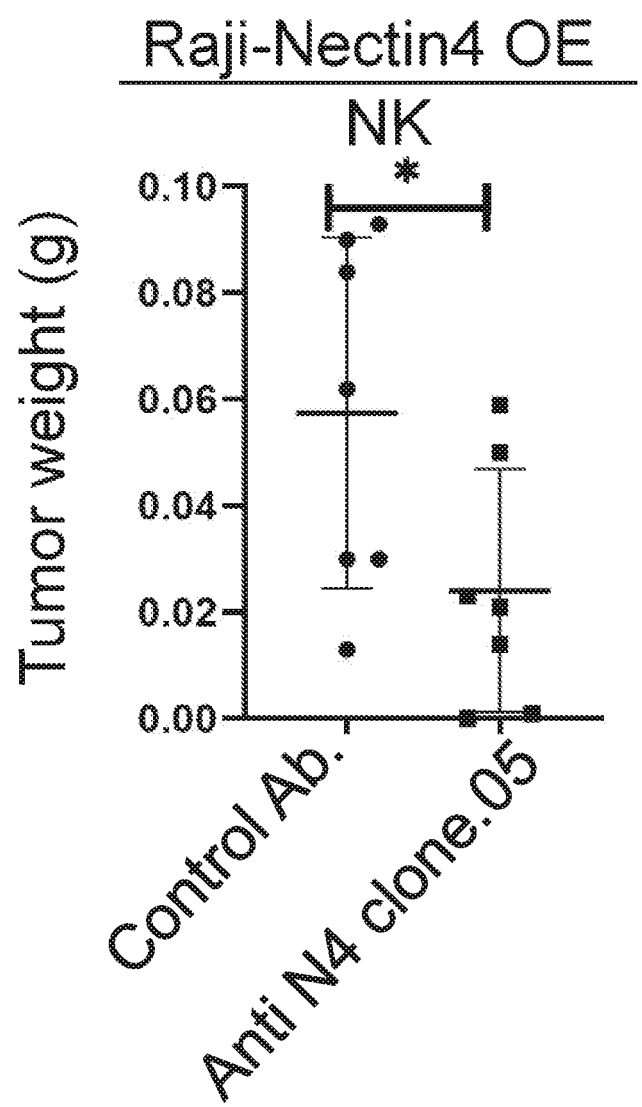
Figure 7C:
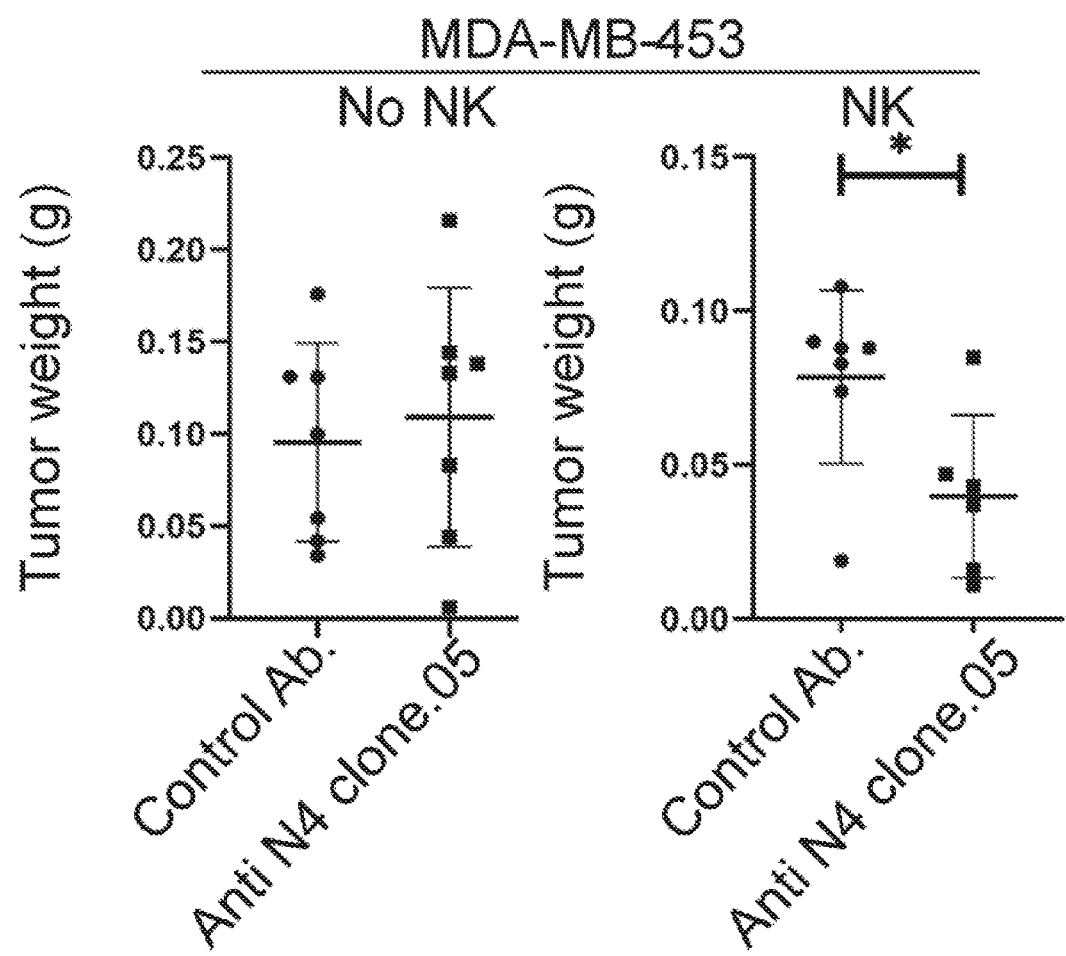

The anti-Nectin4 mAbs clone hNec4.05, or a control Ab (anti murine CD3, InVivoMAb-clone 17A2) were tested for their in vivo effect on tumor growth directly, or together with NK cells. The mAbs were injected IP at 75 μg per mouse, twice a week. Tumor weights were measured at study termination. As seen in FIG. 7 (A), overexpression (OE) of Nectin-4 on Raji cells did not affect their growth in comparison to the growth of their parental cells which were transfected with empty vector (EV). Nevertheless, in the presence of human NK cells, OE of nectin4 increased tumor growth suggesting a negative effect of Nectin4 on NK mediated tumor suppression activity of NK cells. As seen in FIG. 7B, the addition of anti-Nectin4 Ab blocked NK cell suppression leading to reduced tumor growth in comparison to control Ab treated animals Last, and as can be seen in FIG. 7C these effects were also seen when a cell line (MDA-MB-453) that naturally express Nectin4 was used. In the absence of NK cells the Abs had no effect, while the Abs significantly enhanced the anti-tumor effect of human NK cells co injected with the tumor cells. Together, these experiments indicate that anti-Nectin4 antibodies, such as hNec4.05 mAbs, can augment NK cytotoxicity in vivo and lead to tumor growth inhibition.

Figure 8A:
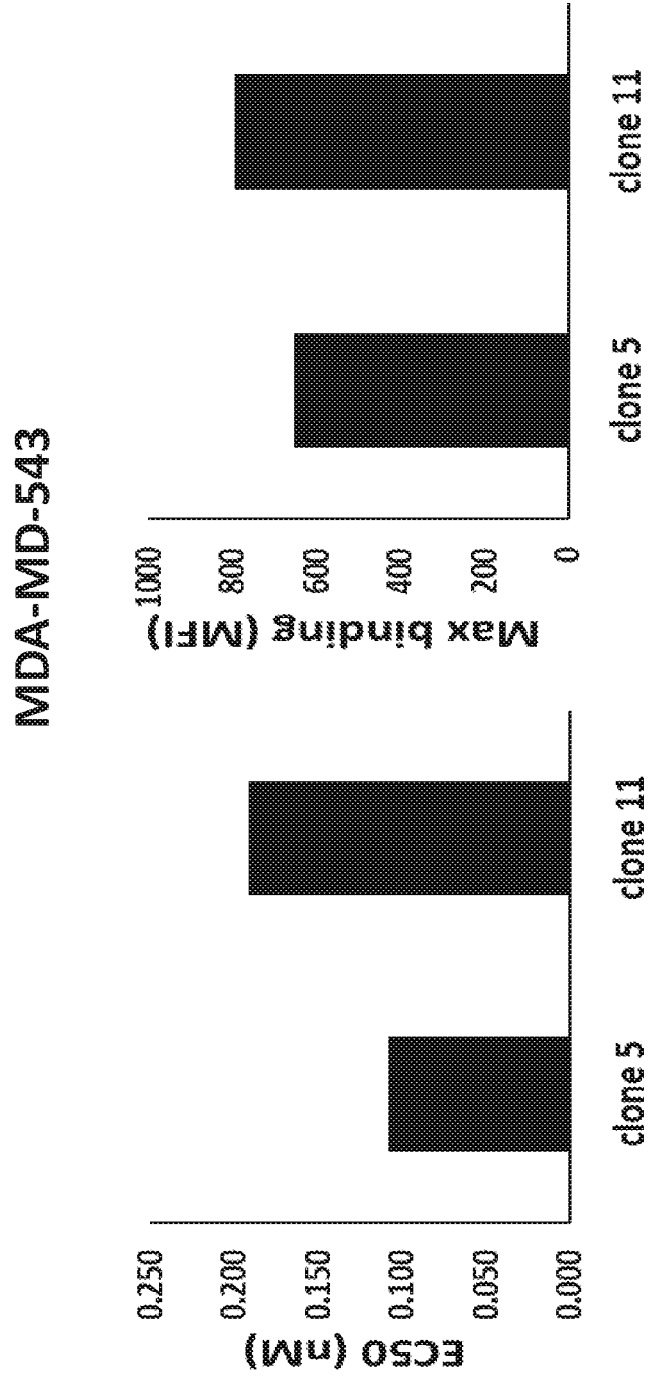
FIGS. 8A-8C Antibody clones hNec4.05 and hNec4.11 binding to cell surface Nectin-4. (A) Antibody binding to Nectin-4 expressed on the human cell line MDA-MD-453 was evaluated by FACS analysis. Shown are the EC50 values that were calculated following titration of Ab binding (range of 20-0.01 nM), and the maximal binding signal for each clone. Of note, similar results were seen with a chimeric version of the Abs in which the murine IgG1 Fc was replaced with human Fc. (B) Antibody binding to CHO cells transfected with Cynomolgus (Cyno)-Nectin-4 and analyzed as in A. (C) Antibody binding to CHO cells transfected with murine-Nectin-4 and analyzed as in A. ND—not detected.
Figure 8B:
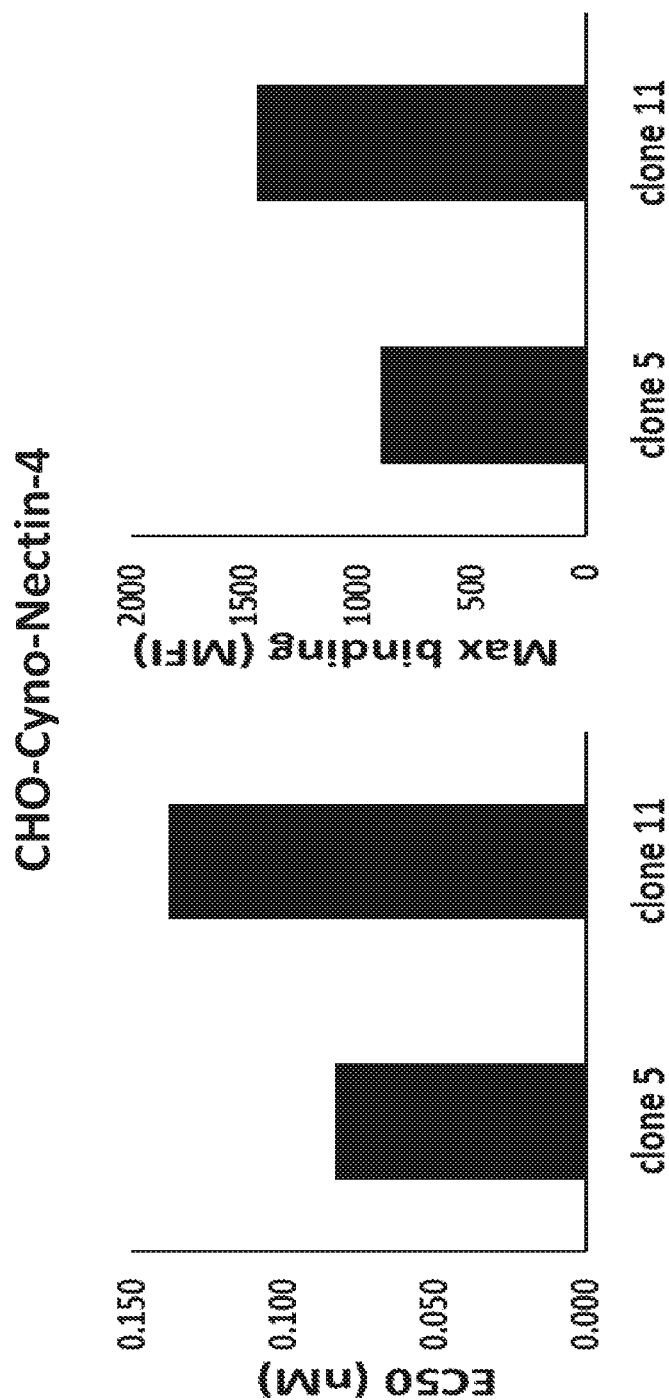
Figure 8C:
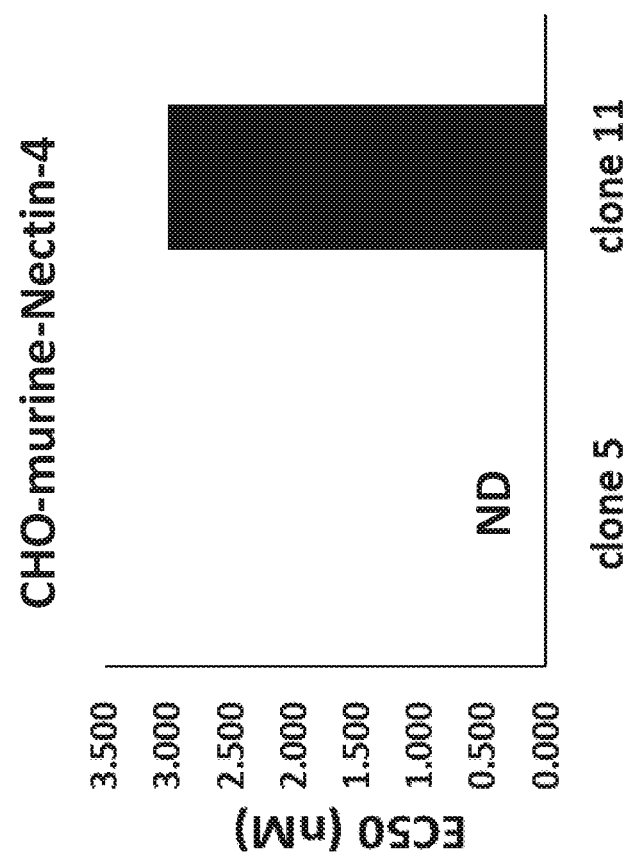
Figure 9A:
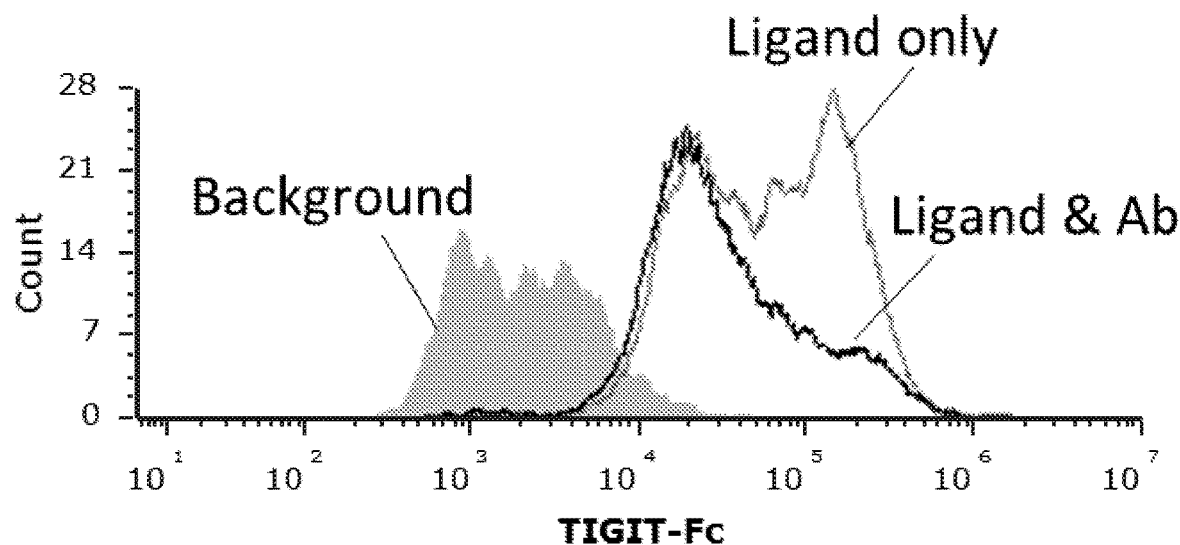
FIGS. 9A-9D Antibody clones hNec4.05 and hNec4.11 block the binding of Nectin-4 to its ligands TIGIT and Nectin-1. Binding of Nectin-4 ligands was assessed by FACS analysis. CHO cells transfected with human-Nectin-4 were incubated with either human TIGIT-Ig (A & C) or with human Nectin-1-Ig (B & D), both at 20 ug/ml, with or without anti-Nectin-4 clone hNec4.05 (A & B) or clone hNec4.11 (C & D), both at 8 ug/ml. Robust binding inhibition by the anti-Nectin-4 Abs is seen in all cases. Remaining signal is likely due to ligand binding to other receptors expressed by CHO cells, such as PVR, which are not affected by the anti-Nectin-4 Abs.
Figure 9B:
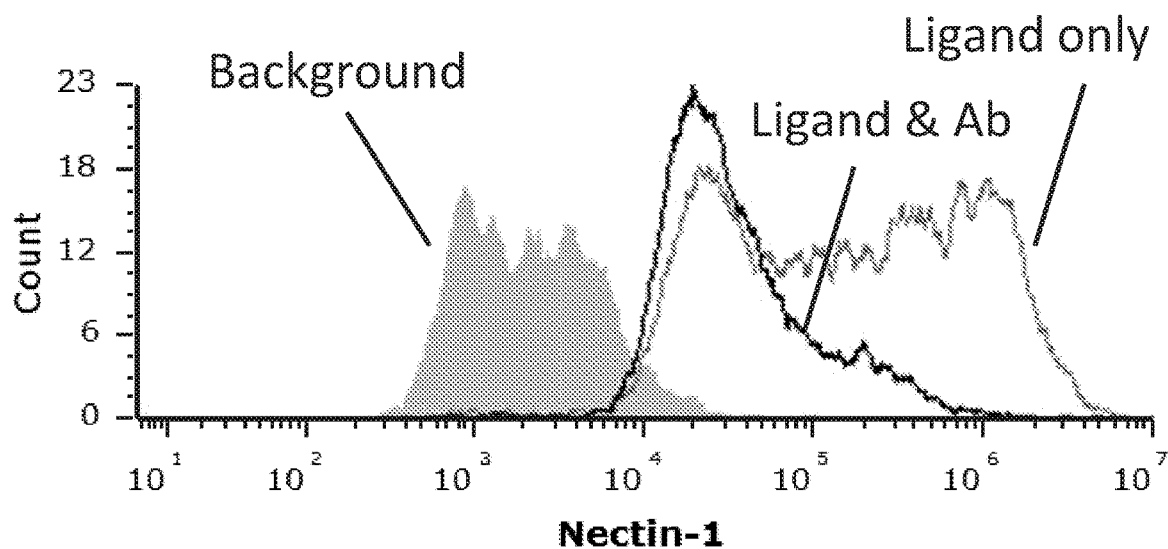
Figure 9C:
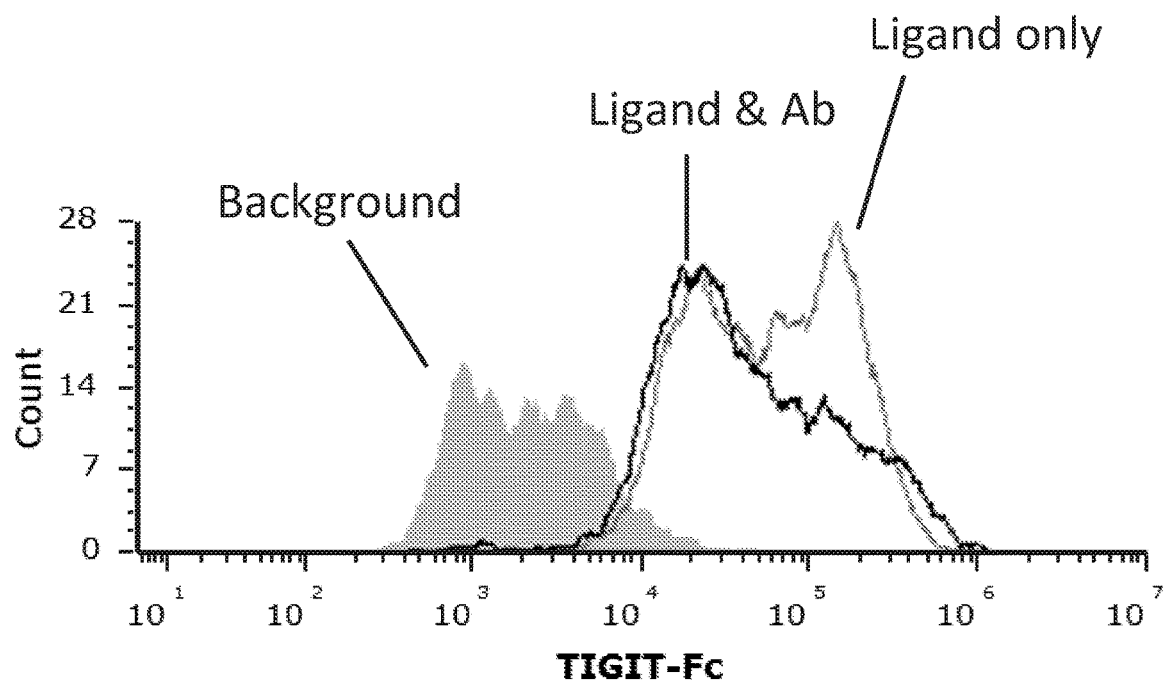
Figure 9D:
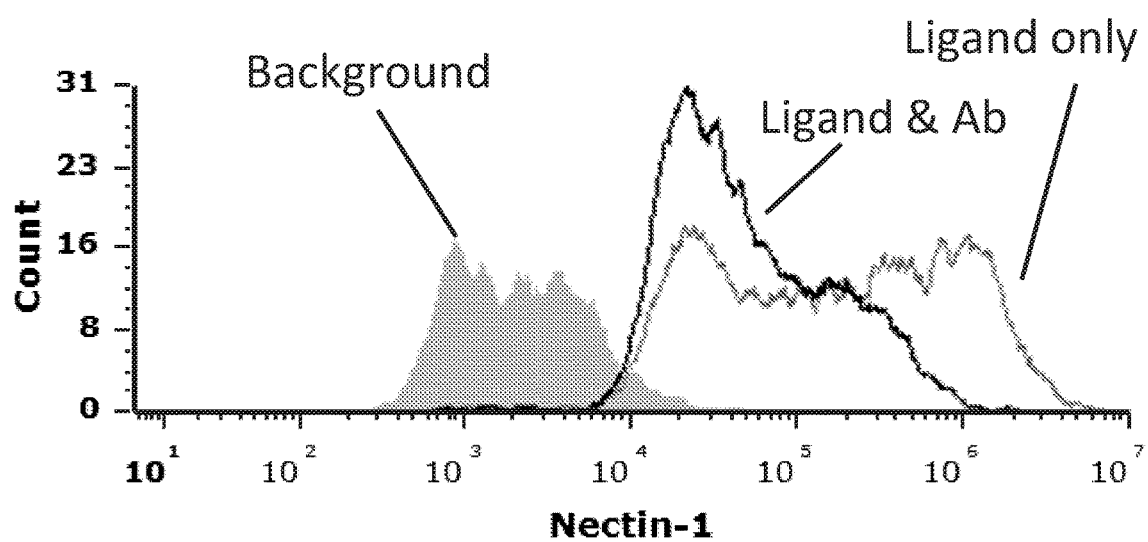

Example 8. Binding of Anti-Nectin-4 Clones to Human, Monkey and Murine Nectin-4 Expressed on Cells Binding of murine anti-human Nectin-4 clones hNec4.05 and hNec4.11 to Nectin-4 expressed on the human cell line MDA-MD-453 was evaluated by FACS analysis. FIG. 8A depicts the EC50 values that were calculated following titration of Ab binding (range of 20-0.01 nM), and the maximal binding signal for each clone Similar values were reached when the chimeric versions of the murine Abs were tested, in which the murine IgG1 Fc chain was replaced with the human IgG1 Fc one. FIG. 8B depicts antibody binding to CHO cells transfected with Cynomolgus (Cyno)-Nectin-4 and FIG. 8C depicts antibody binding to CHO cells transfected with murine-Nectin-4. These data demonstrate EC50 values to the human target at the sub-nanomolar range, which are at the scale of the Kd values presented in FIG. 3 for clones hNec4.01 and hNec4.05. Additionally, these results demonstrate cross reactivity of these two clones to the monkey (cynomolgus) Nectin-4 target, as they bind it with similar EC50 values to the ones calculated for the human target. This may be important for pre-clinical studies of the Ab. Last, clone hNec4.11, but not clone hNec4.05, was shown to also cross react with the murine Nectin-4 target. Yet, in this case the calculated EC50 was about 10-fold higher than the one calculated for the human target.

Example 9. Blocking of Nectin-4 Ligands by Anti-Nectin-4 Clones

Antibody clones hNec4.05 and hNec4.11 block the binding of Nectin-4 to its ligands TIGIT and Nectin-1. Binding of Nectin-4 ligands was assessed by FACS analysis. CHO cells transfected with human-Nectin-4 were incubated with either human TIGIT-Ig (FIGS. 9 A & C) or with human Nectin-1-Ig (FIGS. 9 B & D), both at 20 ug/ml, with or without anti-Nectin-4 clone hNec4.05 (9A & 9B) or clone hNec4.11 (9C & 9D), both at 8 ug/ml. Robust binding inhibition by the anti-Nectin-4 Abs is seen in all cases. Remaining signal is likely due to ligand binding to other receptors expressed by CHO cells, such as PVR, which are not affected by the anti-Nectin-4 Abs. These results suggest that Nectin-4 clones hNec4.05 and hNec4.11 may affect the target cancer cells by blocking signaling through cell surface Nectin-4. Additionally, these Abs may also affect effector cells which express Nectin-4 ligands, such as the inhibitory ligand TIGIT.

Figure 10A:
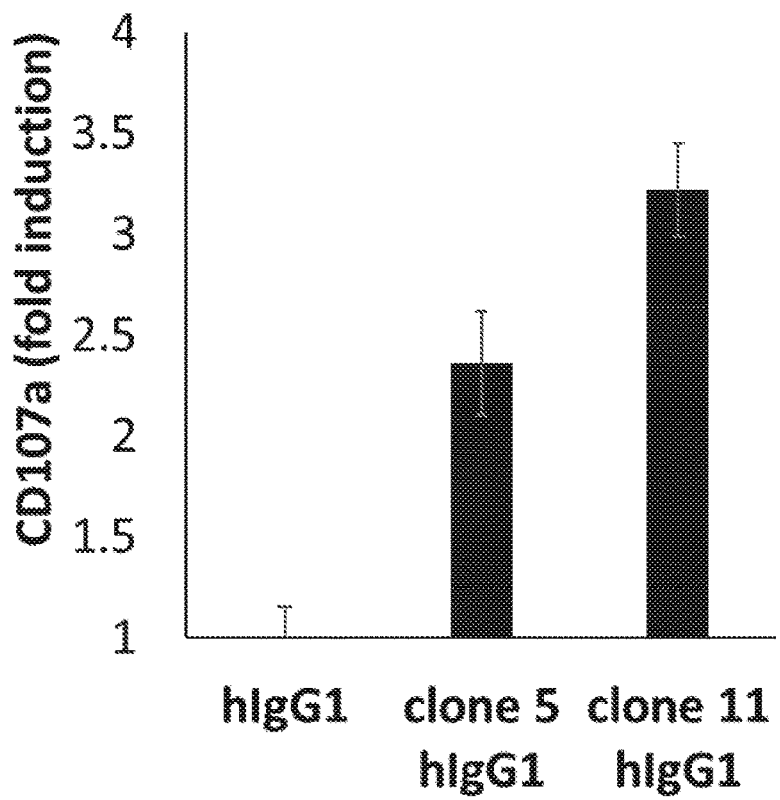
FIGS. 10A-10B Human IgG1 chimeric Ab clones hNec4.05 and hNec4.11 enhance NK cell activation in the presence of tumor cells. Human NK cells (effector, E) were incubated with the target cells (T) HT1376 (A) and MDA-MD-453 (B) at E:T ratio of 2:1. Incubation was done in the presence of 12 ug/ml chimeric clones hNec4.05 and hNec4.11 or a control hIgG1. After two hours, NK cells were assayed for their degranulation and activation status by FACS analysis of CD107a expression. Degranulation of NK cells in presence of control hIgG1 was set as 1 and fold induction was calculated accordingly. Shown are averages of 2-3 repeats and their normalized SDs.
Figure 10B:
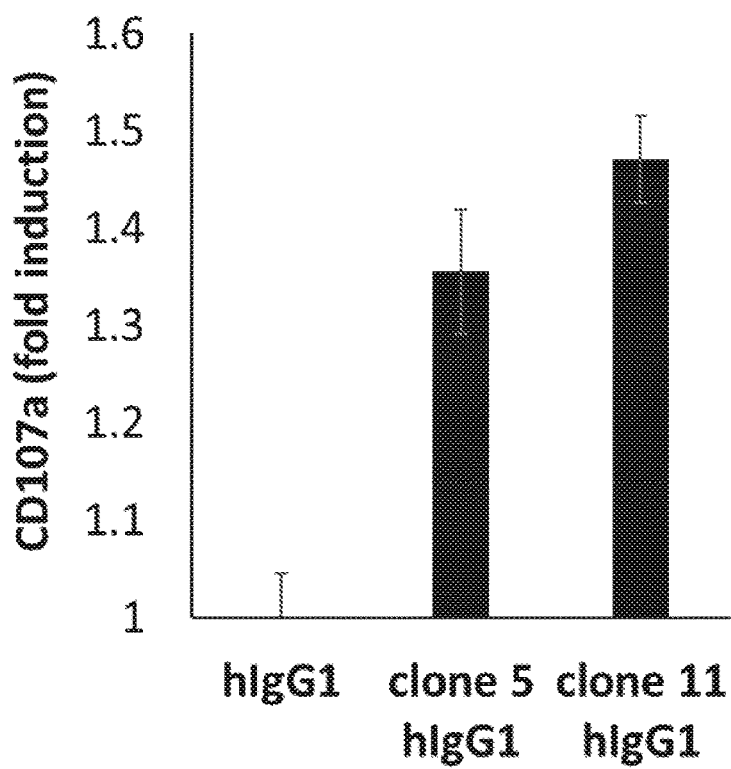

Example 10. Human IgG1 Chimeric Ab Clones hNec4.05 and hNec4.1 Enhance NK Cell Activation in the Presence of Tumor Cells Depicted in FIG. 11 are relative expression levels of the degranulation marker CD107a on NK cells. Human NK cells (effector, E) were incubated with the target cells (T) HT1376 (FIG. 10A) and MDA-MD-453 (FIG. 10B) at E:T ratio of 2:1. Incubation was done in the presence of 12 ug/ml chimeric clones hNec4.05hIgG1, hNec4.11hIgG1 or a control hIgG1. After two hours NK cells were assayed for their degranulation and activation status by FACS analysis of CD107a expression. Degranulation of NK cells in presence of control hIgG1 was set as 1 and fold induction was calculated accordingly. Shown are averages of 2-3 repeats and their normalized SDs. These results suggest an anti-cancer effect for these Abs by enhancing anti-tumor NK cell activity. Slight advantage of clone hNec4.11-hIgG1 over clone hNec4.05hIgG1 in ADCC induction was shown, which is in line with the higher max binding of clone hNec4.11 as shown in FIG. 8A.

Example 11. CAR-T Driven by hNec4.11 Lead to Specific T Cell Activation in the Presence of Tumor Cells Expressing Nectin-4

Figure 11C:
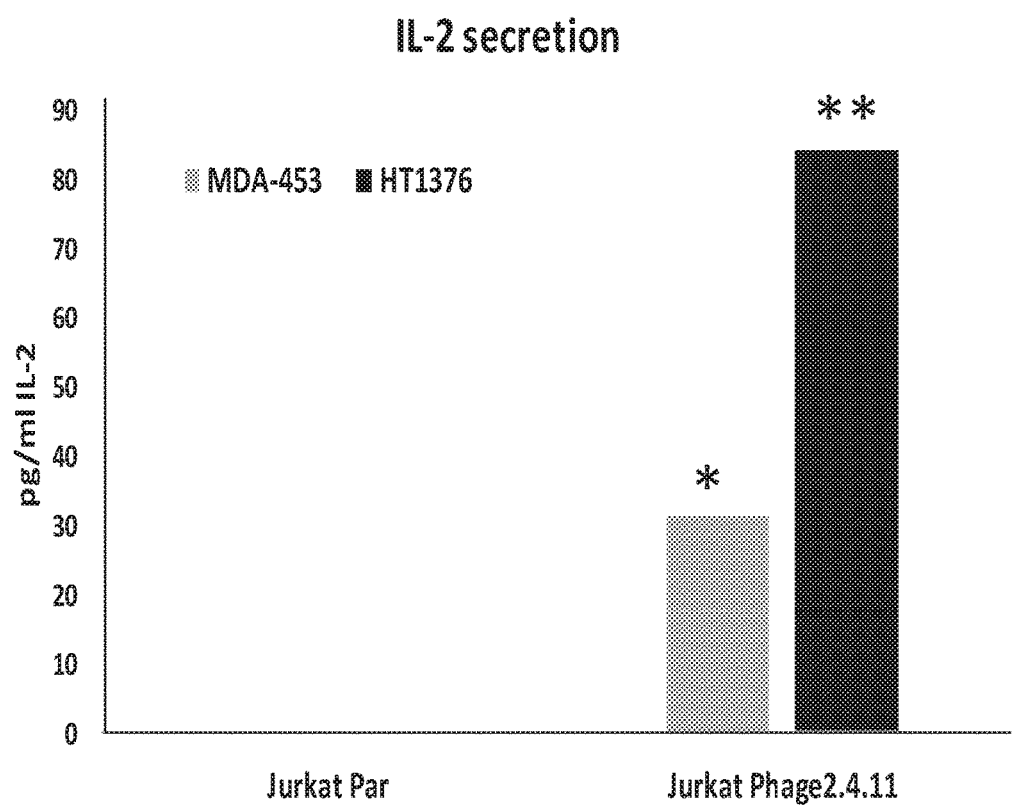
Figure 11D:
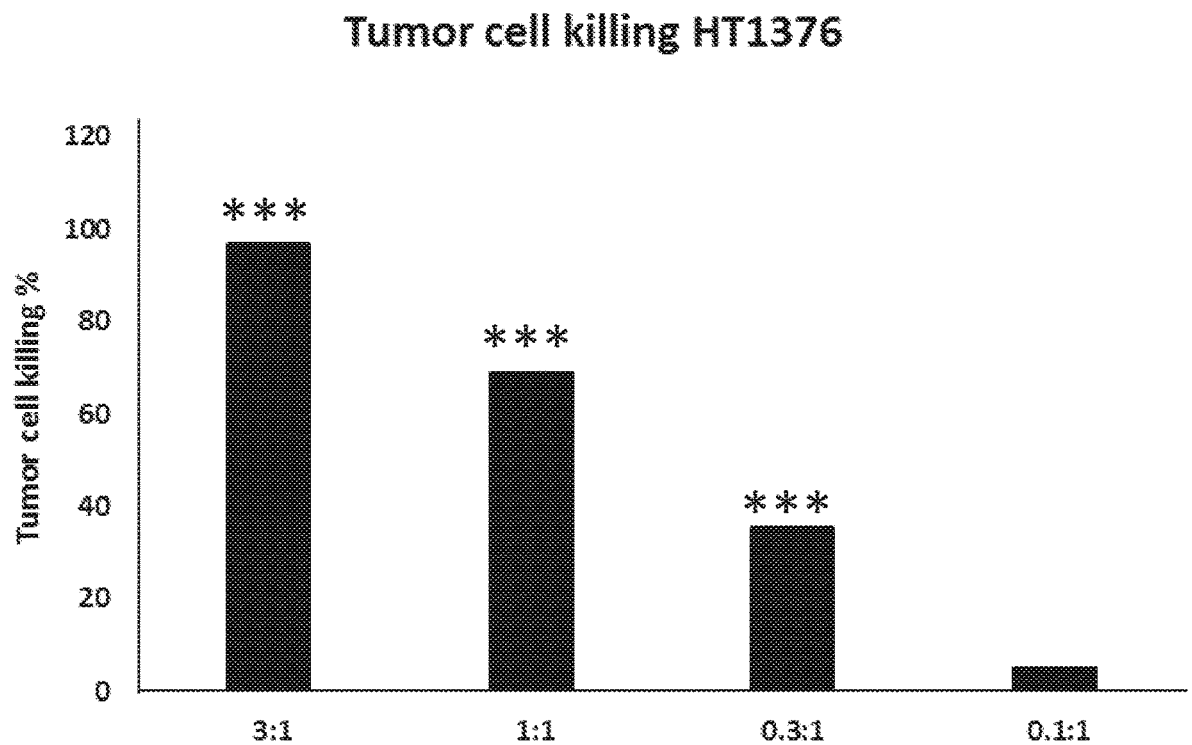

A schematic drawing of the CAR-T construct is seen in FIG. 11A. The transduction efficacy as judged by GFP expression was above 99% (FIG. 11B). Parental Jurkat cells or Jurkat cells expressing the CAR-T construct with hNec4.11-based single chain variable region (scFV) (Jurkat pHAGE2.4.11) were incubated with the target cells HT1376 and MDA-MD-453 (MDA-453) (FIG. 11C). The secretion of IL-2 by the Jurkat cells was significantly induced by the CAR-T expression. Next, PBMCs were transduced using pHAGE2.4.11 lenti particles (FIG. 11D). CAR-T PBMCs were incubated with HT1376 cells through a range of E:Ts. After 48 hours the effector cells were removed, and target cell viability was assessed using CellTiter-Glo® Luminescent Cell Viability Assay. The killing of the target cells was significant. Taken together these observations point to the possibility of further developing CAR-T therapy that is based on the nectin4 Abs described herein.

---

ScFv sequences of CAR construct

Clone 11-Nucleic acids (SEQ ID NO: 31)
ATGGGATGGAGCTGTATCATCCTCTTCTTGGTAGCAACAGCTACAGGTG
TGCATTCACAGGTCCAGCTGCAGCAGTCTGGACCTGAACTGGTGAAGCC
TGAGACTTCAGTGAAGATTTCCTGCAAGGCTTCTGGCTACACCTTCACA
AGTTACTATATACACTGGGTGAAACAGAGGCCTGGACAGGGACTTGAGT
GGATTGGCTGGATTTATCCTGGAAATGTTAATACTAAGTATAATGAGAG
GTTTAAGGGCAAGGCCACTCTGACTGCAGACAAATCCTCCAACACAGCC
CACATGCAGCTCACCAGCCTGACCTCTGAGGACTCTGCGGTCTATTTCT
GTGCAAGATCGAACCCCTATGTTATGGACTACTGGGGTCAAGGAACCTC
AGTCACCGTCTCCTCAGGTGGAGGTGGCTCCGGAGGAGGTGGTTCTGGA
GGAGGTGGTTCTGATATCGTGATGACCCAGACTCCCAAATTCCTGCTTG
TATCAGCAGGAGACAGAGTCACCATAACCTGCAAGGCCAGTCAGAGTGT
GAATAATGATGTGGCTTGGTATCAACAGAAGCCAGGGCTGTCTCCTGAA
CTGCTTATGTATTATGCATCCAATCGCTTCACTGGAGTCCCTGATCGCT
TCACTGGCAGTGGATATGGGACGGATTTCACTTTCACCATCAGCTCTGT
GCAGGCTGAAGACCTGGCAATTTATTTCTGTCAGCAGGCTTATAGGTCT
CCGTACACGTTCGGAGGGGGGACCAAGCTGGAAATTCAA Clone 11-Amino acids  (SEQ ID NO: 32)
MGWSCIILFLVATATGVHSQVQLQQSGPELVKPETSVKISCKASGYTFT
SYYIHWVKQRPGQGLEWIGWIYPGNVNTKYNERFKGKATLTADKSSNTA
HMQLTSLTSEDSAVYFCARSNPYVMDYWGQGTSVTVSSGGGGSGGGGSG
GGGSDIVMTQTPKFLLVSAGDRVTITCKASQSVNNDVAWYQQKPGLSPE
LLMYYASNRFTGVPDRFTGSGYGTDFTFTISSVQAEDLAIYFCQQAYRS
PYTFGGGTKLEIQ Clone 5-Nucleic acids (SEQ ID NO: 33)
ATGGGATGGAGCTGTATCATCCTCTTCTTGGTAGCAACAGCTACAGGTG
TGCATTCACAGGTCCAGCTGCAGCAGTCTGGACCTGAGCTGGTGAAGCC
TGGGGCTTCAGTGAGGATATCCTGCAAGGCCTCTGGCTACACCTTCACA
ACCTACTATATACACTGGGTGAAGCAGAGGCCTGGACAGGGACTTGAGT
GGATTGGATGGATTTATCCTGGAAATGTTAATACTAAGAACAATGAGAA
GTTCAAGGTCAAGGCCACACTGACTGCAGACAAATCCTCCAGCACAGCC
TACATGCAGCTCAGCAGCCTGACCTCTGAGGACTCTGCGGTCTATTTCT
GTGCAAGATCGAACCCCTATGTTATGGACTACTGGGGTCAGGGAACCTC
AGTCACCGTCTCCTCAGGTGGAGGTGGCTCCGGAGGAGGTGGTTCTGGA
GGAGGTGGTTCTAGTATTGTGATGACCCAGACTCCCAAATTCCTGCTTG
TATCAGCAGGAGACAGGGTTACCATAACCTGCAAGGCCAGTCAGAGTGT
GAGTAATGATGTAGCTTGGTACCAACAGAAGCCAGGGCAGTCTCCTAAA
CTGCTGATATACTATGCATCCAATCGCTACACTGGAGTCCCTGATCGCT
TCACTGGCAGTGGATATGGGACGGATTTCACTTTCACCATCAGCGCTGT
GCAGGCTGAAGACCTGGCAGTTTATTTCTGTCAGCAGGATTATAGCTCT
CCGTACACGTTCGGAGGGGGGACCAAGCTGGAAATAAAA Clone 5-Amino acids  (SEQ ID NO: 34)
MGWSCIILFLVATATGVHSQVQLQQSGPELVKPGASVRISCKASGYTFT
TYYIHWVKQRPGQGLEWIGWIYPGNVNTKNNEKFKVKATLTADKSSSTA
YMQLSSLTSEDSAVYFCARSNPYVMDYWGQGTSVTVSSGGGGSGGGGSG
GGGSSIVMTQTPKFLLVSAGDRVTITCKASQSVSNDVAWYQQKPGQSPK
LLIYYASNRYTGVPDRFTGSGYGTDFTFTISAVQAEDLAVYFCQQDYSS
PYTFGGGTKLEIK

---

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

The invention claimed is:

1. An isolated monoclonal antibody which binds to human Nectin4, or an antibody fragment thereof comprising at least the antigen binding portion, wherein the isolated antibody or antibody fragment is capable of inhibiting the binding of Nectin4 to T cell immunoreceptor with Ig and ITIM domains (TIGIT), wherein the isolated antibody or antibody fragment comprises a set of six complementarity determining regions (CDRs) selected from the group consisting of:
  (i) a heavy chain (HC) CDR1 with the amino acid sequence SYYIH (SEQ ID NO: 25); a HC CDR2 with the amino acid sequence WIYPGNVNTKYNERFKG (SEQ ID NO: 26); a HC CDR3 with the amino acid sequence SNPYVMDY (SEQ ID NO: 27); a light chain (LC) CDR1 with the amino acid sequence KASQSVNNDVA (SEQ ID NO: 28); a LC CDR2 with the amino acid sequence YASNRFT (SEQ ID NO: 29); and a LC CDR3 with the amino acid sequence QQAYRSPYT (SEQ ID NO: 30);
  (ii) a HC CDR1 with the amino acid sequence AYNIH (SEQ ID NO: 9), a HC CDR2 is with the amino acid sequence YIYPNNGGSGYNQKFMN (SEQ ID NO: 10), a HC CDR3 with the amino acid sequence FDYDEAWFIY (SEQ ID NO: 11), LC CDR1 is SASSSVSYMH (SEQ ID NO: 12), a LC CDR2 with the amino acid sequence DTSKLAS (SEQ ID NO: 13), and a LC CDR3 with the amino acid sequence FQGSGSPYT (SEQ ID NO: 14); and
  (iii) a HC CDR1 with the amino acid sequence TYYIH (SEQ ID NO: 15), a HC CDR2 with the amino acid sequence WIYPGNVNTKNNEKFKV (SEQ ID NO: 16), a HC CDR3 with the amino acid sequence SNPYVMDY (SEQ ID NO: 17), a LC CDR1 with the amino acid sequence KASQSVSNDVA (SEQ ID NO: 18), a LC CDR2 with the amino acid sequence YASNRYT (SEQ ID NO: 19), and a LC CDR3 with the amino acid sequence QQDYSSPYT (SEQ ID NO: 20).

2. The isolated monoclonal antibody or the antibody fragment according to claim 1, comprising CDR set (i), wherein the 3 HC CDRs and the 3 LC CDRs are contained in a heavy chain and a light chain comprising the amino acid sequence of SEQ ID NO: 39 and SEQ ID NO: 40, respectively.

3. The isolated monoclonal antibody or the antibody fragment according to claim 1, comprising CDR set (ii), wherein the 3 HC CDRs and the 3 LC CDRs are contained in a heavy chain and a light chain, wherein the heavy chain comprises SEQ ID NO: 35 and the light chain comprises SEQ ID NO: 36.

4. The isolated monoclonal antibody or the antibody fragment according to claim 1, comprising CDR set (iii), wherein the 3 HC CDRs and the 3 LC CDRs are contained in a heavy chain and a light chain, wherein the heavy chain comprises SEQ ID NO: 37 and the light chain comprises SEQ ID NO: 38.

5. An isolated monoclonal fragment according to claim 1, wherein the fragment is a single chain Fv (scFv).

6. The scFv of claim 5, comprising a sequence of SEQ ID NO: 32, SEQ ID NO: 34, or a variant thereof having at least 90% sequence similarity with SEQ ID NO: 32 or SEQ ID NO 34, wherein SEQ ID NO: 32 comprises CDR set (i) of claim 1, and SEQ ID NO: 34 comprises CDR set (iii) of claim 1.

7. The isolated monoclonal antibody or antibody fragment according to claim 1, wherein the monoclonal antibody binds to human Nectin4 with an affinity of $10^{-9}$M to $10^{-10}$M.

8. A pharmaceutical composition comprising as an active ingredient, at least one isolated antibody or fragment thereof, according to claim 1, and a pharmaceutical acceptable excipient, diluent, salt, or carrier.

9. The pharmaceutical composition of claim 8 wherein the monoclonal antibody is not conjugated to a cytotoxic moiety.

10. A method of diagnosing a cancer in a subject, the method comprising contacting a biological sample with an antibody or antibody fragment according to claim 1.

11. A chimeric antigen receptor (CAR) comprising at least one antibody or antibody fragment according to claim 1.

12. The CAR according to claim 11, comprising a sequence selected from the group consisting of SEQ ID NOs: 32 and 34, a transmembrane domain, and an intracellular T or NK cell signaling domain.

13. A population of T-cells or NK-cells engineered to express the CAR according to claim 11.

* * * * *

SEQUENCE LISTING

<160> NUMBER OF SEQ ID NOS: 46

<210> SEQ ID NO 1
<211> LENGTH: 414
<212> TYPE: DNA
<213> ORGANISM: Mus musculus

<400> SEQUENCE: 1

```
atgggatgga gctggatctt tctcttcctc ctgtcaggaa ctgcaggctt ccactctgag      60
gtccaacttc agcagtcagg acctgaactg gtgaaacctg gggcctcagt gaagattgcc     120
tgcagggcct ctggatacac attcactgcc tacaatatcc actgggtgag ccagagacat     180
ggaaagagcc ttgaatggat tggatatatc tatcctaaca atggtggttc tggctacaac     240
cagaaattca tgaacaaggc cacattgact gtagaccatt cctccaatac agcctacatg     300
gagctccgca gcctgacgtc tgaggactct gcagtctatt actgtgcaat atttgattac     360
gacgaggcct ggtttattta ctggggccaa gggactctgg tcactgtctc tgca           414
```

<210> SEQ ID NO 2
<211> LENGTH: 138
<212> TYPE: PRT
<213> ORGANISM: Mus musculus

<400> SEQUENCE: 2

```
Met Gly Trp Ser Trp Ile Phe Leu Phe Leu Leu Ser Gly Thr Ala Gly
1               5                   10                  15
Phe His Ser Glu Val Gln Leu Gln Gln Ser Gly Pro Glu Leu Val Lys
            20                  25                  30
Pro Gly Ala Ser Val Lys Ile Ala Cys Arg Ala Ser Gly Tyr Thr Phe
        35                  40                  45
Thr Ala Tyr Asn Ile His Trp Val Ser Gln Arg His Gly Lys Ser Leu
    50                  55                  60
Glu Trp Ile Gly Tyr Ile Tyr Pro Asn Asn Gly Gly Ser Gly Tyr Asn
65                  70                  75                  80
Gln Lys Phe Met Asn Lys Ala Thr Leu Thr Val Asp His Ser Ser Asn
                85                  90                  95
Thr Ala Tyr Met Glu Leu Arg Ser Leu Thr Ser Glu Asp Ser Ala Val
            100                 105                 110
Tyr Tyr Cys Ala Ile Phe Asp Tyr Asp Glu Ala Trp Phe Ile Tyr Trp
        115                 120                 125
Gly Gln Gly Thr Leu Val Thr Val Ser Ala
    130                 135
```

<210> SEQ ID NO 3
<211> LENGTH: 384
<212> TYPE: DNA
<213> ORGANISM: Mus musculus

<400> SEQUENCE: 3

```
atggatttc aagtgcagat tttcagcttc ctgctaatca gtgcctcagt cataatgtcc       60
agaggagaaa atgttctcac ccagtctcca gaaatcatgt ctgcatctcc cggggaagag     120
gtcaccatga cctgtagtgc cagctcaagt gttagttaca tgcactggtt ccagcagaag     180
tcaactatct cccccaaact ctggatttat gacacatcca actggcttc tggagtcccc      240
ggtcgcttca gtggcagtgg gtctgggcaag tcttactctc tcacgatcag aaacatggag    300
gctgaagatg ttgccaccta ttactgtttt caggggagtg ggagcccgta cacgttcgga    360
```

```
gggggggacca agctggaaat taaa                                          384
```

<210> SEQ ID NO 4
<211> LENGTH: 128
<212> TYPE: PRT
<213> ORGANISM: Mus musculus

<400> SEQUENCE: 4

```
Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Glu Ile
            20                  25                  30

Met Ser Ala Ser Pro Gly Glu Val Thr Met Thr Cys Ser Ala Ser
        35                  40                  45

Ser Ser Val Ser Tyr Met His Trp Phe Gln Gln Lys Ser Thr Ile Ser
    50                  55                  60

Pro Lys Leu Trp Ile Tyr Asp Thr Ser Lys Leu Ala Ser Gly Val Pro
65                  70                  75                  80

Gly Arg Phe Ser Gly Ser Gly Ser Gly Lys Ser Tyr Ser Leu Thr Ile
                85                  90                  95

Arg Asn Met Glu Ala Glu Asp Val Ala Thr Tyr Tyr Cys Phe Gln Gly
            100                 105                 110

Ser Gly Ser Pro Tyr Thr Phe Gly Gly Gly Thr Lys Leu Glu Ile Lys
        115                 120                 125
```

<210> SEQ ID NO 5
<211> LENGTH: 408
<212> TYPE: DNA
<213> ORGANISM: Mus musculus

<400> SEQUENCE: 5

```
atgggatgga gccggatctt tctcttcctc ctgtcaataa ttgcaggtgt ccattgccag    60
gtccagctgc agcagtctgg acctgagctg gtgaagcctg gggcttcagt gaggatatcc   120
tgcaaggcct ctggctacac cttcacaacc tactatatac actgggtgaa gcagaggcct   180
ggacagggac ttgagtggat tggatggatt tatcctggaa atgttaatac taagaacaat   240
gagaagttca aggtcaaggc cacactgact gcagacaaat cctccagcac agcctacatg   300
cagctcagca gcctgacctc tgaggactct gcggtctatt tctgtgcaag atcgaacccc   360
tatgttatgg actactgggg tcagggaacc tcagtcaccg tctcctca              408
```

<210> SEQ ID NO 6
<211> LENGTH: 136
<212> TYPE: PRT
<213> ORGANISM: Mus musculus

<400> SEQUENCE: 6

```
Met Gly Trp Ser Arg Ile Phe Leu Phe Leu Leu Ser Ile Ile Ala Gly
1               5                   10                  15

Val His Cys Gln Val Gln Leu Gln Gln Ser Gly Pro Glu Leu Val Lys
            20                  25                  30

Pro Gly Ala Ser Val Arg Ile Ser Cys Lys Ala Ser Gly Tyr Thr Phe
        35                  40                  45

Thr Thr Tyr Tyr Ile His Trp Val Lys Gln Arg Pro Gly Gln Gly Leu
    50                  55                  60

Glu Trp Ile Gly Trp Ile Tyr Pro Gly Asn Val Asn Thr Lys Asn Asn
65                  70                  75                  80
```

```
Glu Lys Phe Lys Val Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Asn Pro Tyr Val Met Asp Tyr Trp Gly Gln
        115                 120                 125

Gly Thr Ser Val Thr Val Ser Ser
        130             135

<210> SEQ ID NO 7
<211> LENGTH: 381
<212> TYPE: DNA
<213> ORGANISM: Mus musculus

<400> SEQUENCE: 7
atgaagtcac agacccaggt cttcgtattt ctactgctct gtgtgtctgg tgctcatggg      60
agtattgtga tgacccagac tcccaaattc ctgcttgtat cagcaggaga cagggttacc     120
ataacctgca aggccagtca gagtgtgagt aatgatgtag cttggtacca acagaagcca     180
gggcagtctc ctaaactgct gatatactat gcatccaatc gctacactgg agtccctgat     240
cgcttcactg gcagtggata tgggacggat ttcactttca ccatcagcgc tgtgcaggct     300
gaagacctgg cagtttattt ctgtcagcag gattatagct ctccgtacac gttcggaggg     360
gggaccaagc tggaaataaa a                                              381

<210> SEQ ID NO 8
<211> LENGTH: 127
<212> TYPE: PRT
<213> ORGANISM: Mus musculus

<400> SEQUENCE: 8

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Ala Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Lys
        115                 120                 125

<210> SEQ ID NO 9
<211> LENGTH: 5
<212> TYPE: PRT
<213> ORGANISM: Mus musculus

<400> SEQUENCE: 9

Ala Tyr Asn Ile His
1               5

<210> SEQ ID NO 10
```

```
<211> LENGTH: 17
<212> TYPE: PRT
<213> ORGANISM: Mus musculus

<400> SEQUENCE: 10

Tyr Ile Tyr Pro Asn Asn Gly Gly Ser Gly Tyr Asn Gln Lys Phe Met
1               5                   10                  15

Asn

<210> SEQ ID NO 11
<211> LENGTH: 10
<212> TYPE: PRT
<213> ORGANISM: Mus musculus

<400> SEQUENCE: 11

Phe Asp Tyr Asp Glu Ala Trp Phe Ile Tyr
1               5                   10

<210> SEQ ID NO 12
<211> LENGTH: 10
<212> TYPE: PRT
<213> ORGANISM: Mus musculus

<400> SEQUENCE: 12

Ser Ala Ser Ser Ser Val Ser Tyr Met His
1               5                   10

<210> SEQ ID NO 13
<211> LENGTH: 7
<212> TYPE: PRT
<213> ORGANISM: Mus musculus

<400> SEQUENCE: 13

Asp Thr Ser Lys Leu Ala Ser
1               5

<210> SEQ ID NO 14
<211> LENGTH: 9
<212> TYPE: PRT
<213> ORGANISM: Mus musculus

<400> SEQUENCE: 14

Phe Gln Gly Ser Gly Ser Pro Tyr Thr
1               5

<210> SEQ ID NO 15
<211> LENGTH: 5
<212> TYPE: PRT
<213> ORGANISM: Mus musculus

<400> SEQUENCE: 15

Thr Tyr Tyr Ile His
1               5

<210> SEQ ID NO 16
<211> LENGTH: 17
<212> TYPE: PRT
<213> ORGANISM: Mus musculus

<400> SEQUENCE: 16

Trp Ile Tyr Pro Gly Asn Val Asn Thr Lys Asn Asn Glu Lys Phe Lys
1               5                   10                  15

Val
```

```
<210> SEQ ID NO 17
<211> LENGTH: 8
<212> TYPE: PRT
<213> ORGANISM: Mus musculus

<400> SEQUENCE: 17

Ser Asn Pro Tyr Val Met Asp Tyr
1               5

<210> SEQ ID NO 18
<211> LENGTH: 11
<212> TYPE: PRT
<213> ORGANISM: Mus musculus

<400> SEQUENCE: 18

Lys Ala Ser Gln Ser Val Ser Asn Asp Val Ala
1               5                   10

<210> SEQ ID NO 19
<211> LENGTH: 7
<212> TYPE: PRT
<213> ORGANISM: Mus musculus

<400> SEQUENCE: 19

Tyr Ala Ser Asn Arg Tyr Thr
1               5

<210> SEQ ID NO 20
<211> LENGTH: 9
<212> TYPE: PRT
<213> ORGANISM: Mus musculus

<400> SEQUENCE: 20

Gln Gln Asp Tyr Ser Ser Pro Tyr Thr
1               5

<210> SEQ ID NO 21
<211> LENGTH: 408
<212> TYPE: DNA
<213> ORGANISM: Mus musculus

<400> SEQUENCE: 21
atgggatgga gccggatctt tctcttcctc ctgtcaataa ttgcaggtgt ccattgccag      60
gtccagctgc agcagtctgg acctgaactg gtgaagcctg agacttcagt gaagatatcc     120
tgcaaggctt ctggctacac cttcacaagt tactatatac actgggtgaa acagaggcct     180
ggacagggac ttgagtggat tggctggatt tatcctggaa atgttaatac taagtataat     240
gagaggttta agggcaaggc cactctgact gcagacaaat cctccaacac agcccacatg     300
cagctcacca gcctgacctc tgaggactct gcggtctatt tctgtgcaag atcgaacccc     360
tatgttatgg actactgggg tcaaggaacc tcagtcaccg tctcctca                  408

<210> SEQ ID NO 22
<211> LENGTH: 136
<212> TYPE: PRT
<213> ORGANISM: Mus musculus

<400> SEQUENCE: 22

Met Gly Trp Ser Arg Ile Phe Leu Phe Leu Leu Ser Ile Ile Ala Gly
1               5                   10                  15

Val His Cys Gln Val Gln Leu Gln Gln Ser Gly Pro Glu Leu Val Lys
            20                  25                  30
```

Pro Glu Thr Ser Val Lys Ile Ser Cys Lys Ala Ser Gly Tyr Thr Phe
           35                  40                  45

Thr Ser Tyr Tyr Ile His Trp Val Lys Gln Arg Pro Gly Gln Gly Leu
 50                  55                  60

Glu Trp Ile Gly Trp Ile Tyr Pro Gly Asn Val Asn Thr Lys Tyr Asn
 65                  70                  75                  80

Glu Arg Phe Lys Gly Lys Ala Thr Leu Thr Ala Asp Lys Ser Ser Asn
                 85                  90                  95

Thr Ala His Met Gln Leu Thr Ser Leu Thr Ser Glu Asp Ser Ala Val
                100                 105                 110

Tyr Phe Cys Ala Arg Ser Asn Pro Tyr Val Met Asp Tyr Trp Gly Gln
            115                 120                 125

Gly Thr Ser Val Thr Val Ser Ser
            130                 135

<210> SEQ ID NO 23
<211> LENGTH: 381
<212> TYPE: DNA
<213> ORGANISM: Mus musculus

<400> SEQUENCE: 23
atgaagtcac agacccaggt cttcgtattt ctactgctct gtgtgtctgg tgctcatggg      60
agtattgtga tgacccagac tcccaaattc ctgcttgtat cagcaggaga cagagtcacc     120
ataacctgca aggccagtca gagtgtgaat aatgatgtgg cttggtatca acagaagcca     180
gggctgtctc ctgaactgct tatgtattat gcatccaatc gcttcactgg agtccctgat     240
cgcttcactg gcagtggata tgggacggat tcacttttca ccatcagctc tgtgcaggct     300
gaagacctgg caatttattt ctgtcagcag gcttataggt ctccgtacac gttcggaggg     360
gggaccaagc tggaaattca a                                               381

<210> SEQ ID NO 24
<211> LENGTH: 127
<212> TYPE: PRT
<213> ORGANISM: Mus musculus

<400> SEQUENCE: 24

Met Lys Ser Gln Thr Gln Val Phe Val Phe Leu Leu Leu Cys Val Ser
 1               5                  10                  15

Gly Ala His Gly Ser Ile Val Met Thr Gln Thr Pro Lys Phe Leu Leu
                 20                  25                  30

Val Ser Ala Gly Asp Arg Val Thr Ile Thr Cys Lys Ala Ser Gln Ser
             35                  40                  45

Val Asn Asn Asp Val Ala Trp Tyr Gln Gln Lys Pro Gly Leu Ser Pro
 50                  55                  60

Glu Leu Leu Met Tyr Tyr Ala Ser Asn Arg Phe Thr Gly Val Pro Asp
 65                  70                  75                  80

Arg Phe Thr Gly Ser Gly Tyr Gly Thr Asp Phe Thr Phe Thr Ile Ser
                 85                  90                  95

Ser Val Gln Ala Glu Asp Leu Ala Ile Tyr Phe Cys Gln Gln Ala Tyr
            100                 105                 110

Arg Ser Pro Tyr Thr Phe Gly Gly Gly Thr Lys Leu Glu Ile Gln
            115                 120                 125

<210> SEQ ID NO 25
<211> LENGTH: 5

```
<212> TYPE: PRT
<213> ORGANISM: Mus musculus

<400> SEQUENCE: 25

Ser Tyr Tyr Ile His
1               5

<210> SEQ ID NO 26
<211> LENGTH: 17
<212> TYPE: PRT
<213> ORGANISM: Mus musculus

<400> SEQUENCE: 26

Trp Ile Tyr Pro Gly Asn Val Asn Thr Lys Tyr Asn Glu Arg Phe Lys
1               5                   10                  15

Gly

<210> SEQ ID NO 27
<211> LENGTH: 8
<212> TYPE: PRT
<213> ORGANISM: Mus musculus

<400> SEQUENCE: 27

Ser Asn Pro Tyr Val Met Asp Tyr
1               5

<210> SEQ ID NO 28
<211> LENGTH: 11
<212> TYPE: PRT
<213> ORGANISM: Mus musculus

<400> SEQUENCE: 28

Lys Ala Ser Gln Ser Val Asn Asn Asp Val Ala
1               5                   10

<210> SEQ ID NO 29
<211> LENGTH: 7
<212> TYPE: PRT
<213> ORGANISM: Mus musculus

<400> SEQUENCE: 29

Tyr Ala Ser Asn Arg Phe Thr
1               5

<210> SEQ ID NO 30
<211> LENGTH: 9
<212> TYPE: PRT
<213> ORGANISM: Mus musculus

<400> SEQUENCE: 30

Gln Gln Ala Tyr Arg Ser Pro Tyr Thr
1               5

<210> SEQ ID NO 31
<211> LENGTH: 774
<212> TYPE: DNA
<213> ORGANISM: Artificial Sequence
<220> FEATURE:
<223> OTHER INFORMATION: Synthetic sequence

<400> SEQUENCE: 31
atgggatgga gctgtatcat cctcttcttg gtagcaacag ctacaggtgt gcattcacag      60
gtccagctgc agcagtctgg acctgaactg gtgaagcctg agacttcagt gaagatttcc     120
```

-continued

```
tgcaaggctt ctggctacac cttcacaagt tactatatac actgggtgaa acagaggcct    180
ggacagggac ttgagtggat tggctggatt tatcctggaa atgttaatac taagtataat    240
gagaggttta agggcaaggc cactctgact gcagacaaat cctccaacac agcccacatg    300
cagctcacca gcctgacctc tgaggactct gcggtctatt tctgtgcaag atcgaacccc    360
tatgttatgg actactgggg tcaaggaacc tcagtcaccg tctcctcagg tggaggtggc    420
tccggaggag gtggttctgg aggaggtggt tctgatatcg tgatgaccca gactcccaaa    480
ttcctgcttg tatcagcagg agacagagtc accataacct gcaaggccag tcagagtgtg    540
aataatgatg tggcttggta tcaacagaag ccagggctgt ctcctgaact gcttatgtat    600
tatgcatcca atcgcttcac tggagtccct gatcgcttca ctggcagtgg atatgggacg    660
gatttcactt tcaccatcag ctctgtgcag gctgaagacc tggcaattta tttctgtcag    720
caggcttata ggtctccgta cacgttcgga ggggggacca agctggaaat tcaa          774
```

<210> SEQ ID NO 32
<211> LENGTH: 258
<212> TYPE: PRT
<213> ORGANISM: Artificial Sequence
<220> FEATURE:
<223> OTHER INFORMATION: Synthetic sequence

<400> SEQUENCE: 32

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Glu Leu Val Lys
            20                  25                  30

Pro Glu Thr Ser Val Lys Ile Ser Cys Lys Ala Ser Gly Tyr Thr Phe
        35                  40                  45

Thr Ser Tyr Tyr Ile His Trp Val Lys Gln Arg Pro Gly Gln Gly Leu
    50                  55                  60

Glu Trp Ile Gly Trp Ile Tyr Pro Gly Asn Val Asn Thr Lys Tyr Asn
65                  70                  75                  80

Glu Arg Phe Lys Gly Lys Ala Thr Leu Thr Ala Asp Lys Ser Ser Asn
                85                  90                  95

Thr Ala His Met Gln Leu Thr Ser Leu Thr Ser Glu Asp Ser Ala Val
            100                 105                 110

Tyr Phe Cys Ala Arg Ser Asn Pro Tyr Val Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Asp Ile Val Met Thr Gln Thr Pro Lys
145                 150                 155                 160

Phe Leu Leu Val Ser Ala Gly Asp Arg Val Thr Ile Thr Cys Lys Ala
                165                 170                 175

Ser Gln Ser Val Asn Asn Asp Val Ala Trp Tyr Gln Gln Lys Pro Gly
            180                 185                 190

Leu Ser Pro Glu Leu Leu Met Tyr Tyr Ala Ser Asn Arg Phe Thr Gly
        195                 200                 205

Val Pro Asp Arg Phe Thr Gly Ser Gly Tyr Gly Thr Asp Phe Thr Phe
    210                 215                 220

Thr Ile Ser Ser Val Gln Ala Glu Asp Leu Ala Ile Tyr Phe Cys Gln
225                 230                 235                 240

Gln Ala Tyr Arg Ser Pro Tyr Thr Phe Gly Gly Gly Thr Lys Leu Glu
                245                 250                 255
```

Ile Gln

<210> SEQ ID NO 33
<211> LENGTH: 774
<212> TYPE: DNA
<213> ORGANISM: Artificial Sequence
<220> FEATURE:
<223> OTHER INFORMATION: Synthetic sequence

<400> SEQUENCE: 33

```
atgggatgga gctgtatcat cctcttcttg gtagcaacag ctacaggtgt gcattcacag    60
gtccagctgc agcagtctgg acctgagctg gtgaagcctg gggcttcagt gaggatatcc   120
tgcaaggcct ctggctacac cttcacaacc tactatatac actgggtgaa gcagaggcct   180
ggacagggac ttgagtggat tggatggatt tatcctggaa atgttaatac taagaacaat   240
gagaagttca aggtcaaggc cacactgact gcagacaaat cctccagcac agcctacatg   300
cagctcagca gcctgacctc tgaggactct gcggtctatt tctgtgcaag atcgaacccc   360
tatgttatgg actactgggg tcagggaacc tcagtcaccg tctcctcagg tggaggtggc   420
tccggaggag gtggttctgg aggaggtggt tctagtattg tgatgaccca gactcccaaa   480
ttcctgcttg tatcagcagg agacagggtt accataacct gcaaggccag tcagagtgtg   540
agtaatgatg tagcttggta ccaacagaag ccagggcagt ctcctaaact gctgatatac   600
tatgcatcca atcgctacac tggagtccct gatcgcttca ctggcagtgg atatgggacg   660
gatttcactt tcaccatcag cgctgtgcag gctgaagacc tggcagttta tttctgtcag   720
caggattata gctctccgta cacgttcgga ggggggacca agctggaaat aaaa         774
```

<210> SEQ ID NO 34
<211> LENGTH: 258
<212> TYPE: PRT
<213> ORGANISM: Artificial Sequence
<220> FEATURE:
<223> OTHER INFORMATION: Synthetic sequence

<400> SEQUENCE: 34

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Glu Leu Val Lys
            20                  25                  30

Pro Gly Ala Ser Val Arg Ile Ser Cys Lys Ala Ser Gly Tyr Thr Phe
        35                  40                  45

Thr Thr Tyr Tyr Ile His Trp Val Lys Gln Arg Pro Gly Gln Gly Leu
    50                  55                  60

Glu Trp Ile Gly Trp Ile Tyr Pro Gly Asn Val Asn Thr Lys Asn Asn
65                  70                  75                  80

Glu Lys Phe Lys Val Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Asn Pro Tyr Val Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Ser Ile Val Met Thr Gln Thr Pro Lys
145                 150                 155                 160
```

```
Phe Leu Leu Val Ser Ala Gly Asp Arg Val Thr Ile Thr Cys Lys Ala
                    165                 170                 175

Ser Gln Ser Val Ser Asn Asp Val Ala Trp Tyr Gln Lys Pro Gly
            180                 185                 190

Gln Ser Pro Lys Leu Leu Ile Tyr Tyr Ala Ser Asn Arg Tyr Thr Gly
            195                 200                 205

Val Pro Asp Arg Phe Thr Gly Ser Gly Tyr Gly Thr Asp Phe Thr Phe
    210                 215                 220

Thr Ile Ser Ala Val Gln Ala Glu Asp Leu Ala Val Tyr Phe Cys Gln
225                 230                 235                 240

Gln Asp Tyr Ser Ser Pro Tyr Thr Phe Gly Gly Gly Thr Lys Leu Glu
            245                 250                 255

Ile Lys

<210> SEQ ID NO 35
<211> LENGTH: 119
<212> TYPE: PRT
<213> ORGANISM: Mus musculus

<400> SEQUENCE: 35

Glu Val Gln Leu Gln Gln Ser Gly Pro Glu Leu Val Lys Pro Gly Ala
1               5                   10                  15

Ser Val Lys Ile Ala Cys Arg Ala Ser Gly Tyr Thr Phe Thr Ala Tyr
                20                  25                  30

Asn Ile His Trp Val Ser Gln Arg His Gly Lys Ser Leu Glu Trp Ile
            35                  40                  45

Gly Tyr Ile Tyr Pro Asn Asn Gly Gly Ser Gly Tyr Asn Gln Lys Phe
    50                  55                  60

Met Asn Lys Ala Thr Leu Thr Val Asp His Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ala Ile Phe Asp Tyr Asp Glu Ala Trp Phe Ile Tyr Trp Gly Gln Gly
                100                 105                 110

Thr Leu Val Thr Val Ser Ala
            115

<210> SEQ ID NO 36
<211> LENGTH: 106
<212> TYPE: PRT
<213> ORGANISM: Mus musculus

<400> SEQUENCE: 36

Glu Asn Val Leu Thr Gln Ser Pro Glu Ile Met Ser Ala Ser Pro Gly
1               5                   10                  15

Glu Glu Val Thr Met Thr Cys Ser Ala Ser Ser Ser Val Ser Tyr Met
                20                  25                  30

His Trp Phe Gln Gln Lys Ser Thr Ile Ser Pro Lys Leu Trp Ile Tyr
            35                  40                  45

Asp Thr Ser Lys Leu Ala Ser Gly Val Pro Gly Arg Phe Ser Gly Ser
    50                  55                  60

Gly Ser Gly Lys Ser Tyr Ser Leu Thr Ile Arg Asn Met Glu Ala Glu
65                  70                  75                  80

Asp Val Ala Thr Tyr Tyr Cys Phe Gln Gly Ser Gly Ser Pro Tyr Thr
                85                  90                  95

Phe Gly Gly Gly Thr Lys Leu Glu Ile Lys
```

<210> SEQ ID NO 37
<211> LENGTH: 117
<212> TYPE: PRT
<213> ORGANISM: Mus musculus

<400> SEQUENCE: 37

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Thr Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Asn Asn Glu Lys Phe
    50                  55                  60

Lys Val Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Asn Pro Tyr Val Met Asp Tyr Trp Gly Gln Gly Thr Ser
            100                 105                 110

Val Thr Val Ser Ser
        115

<210> SEQ ID NO 38
<211> LENGTH: 107
<212> TYPE: PRT
<213> ORGANISM: Mus musculus

<400> SEQUENCE: 38

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Ala Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 39
<211> LENGTH: 117
<212> TYPE: PRT
<213> ORGANISM: Mus musculus

<400> SEQUENCE: 39

Gln Val Gln Leu Gln Gln Ser Gly Pro Glu Leu Val Lys Pro Glu Thr
1               5                   10                  15

Ser Val Lys Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Arg Phe
        50                  55                  60

Lys Gly Lys Ala Thr Leu Thr Ala Asp Lys Ser Ser Asn Thr Ala His
 65                  70                  75                  80

Met Gln Leu Thr Ser Leu Thr Ser Glu Asp Ser Ala Val Tyr Phe Cys
                85                  90                  95

Ala Arg Ser Asn Pro Tyr Val Met Asp Tyr Trp Gly Gln Gly Thr Ser
                100                 105                 110

Val Thr Val Ser Ser
        115

<210> SEQ ID NO 40
<211> LENGTH: 107
<212> TYPE: PRT
<213> ORGANISM: Mus musculus

<400> SEQUENCE: 40

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Asn Asn Asp
                20                  25                  30

Val Ala Trp Tyr Gln Gln Lys Pro Gly Leu Ser Pro Glu Leu Leu Met
            35                  40                  45

Tyr Tyr Ala Ser Asn Arg Phe Thr Gly Val Pro Asp Arg Phe Thr Gly
 50                  55                  60

Ser Gly Tyr Gly Thr Asp Phe Thr Phe Thr Ile Ser Ser Val Gln Ala
 65                  70                  75                  80

Glu Asp Leu Ala Ile Tyr Phe Cys Gln Gln Ala Tyr Arg Ser Pro Tyr
                85                  90                  95

Thr Phe Gly Gly Gly Thr Lys Leu Glu Ile Gln
                100                 105

<210> SEQ ID NO 41
<211> LENGTH: 357
<212> TYPE: DNA
<213> ORGANISM: Mus musculus

<400> SEQUENCE: 41
gaggtccaac ttcagcagtc aggacctgaa ctggtgaaac ctggggcctc agtgaagatt      60
gcctgcaggg cctctggata cacattcact gcctacaata tccactgggt gagccagaga     120
catgaaaaga ccttgaatg gattggatat atctatccta acaatggtgg ttctggctac     180
aaccagaaat tcatgaacaa ggccacattg actgtagacc attcctccaa tacagcctac     240
atggagctcc gcagcctgac gtctgaggac tctgcagtct attactgtgc aatatttgat     300
tacgacgagg cctggtttat ttactggggc caagggactc tggtcactgt ctctgca       357

<210> SEQ ID NO 42
<211> LENGTH: 318
<212> TYPE: DNA
<213> ORGANISM: Mus musculus

<400> SEQUENCE: 42
gaaaatgttc tcacccagtc tccagaaatc atgtctgcat ctcccgggga gaggtcacc       60 atgacctgta gtgccagctc aagtgttagt tacatgcact ggttccagca gaagtcaact     120
atctccccca aactctggat ttatgacaca tccaaactgg cttctggagt ccccggtcgc     180

```
ttcagtggca gtgggtctgg caagtcttac tctctcacga tcagaaacat ggaggctgaa    240
gatgttgcca cctattactg ttttcagggg agtgggagcc cgtacacgtt cggaggggggg   300 accaagctgg aaattaaa                                                   318

<210> SEQ ID NO 43
<211> LENGTH: 357
<212> TYPE: DNA
<213> ORGANISM: Mus musculus

<400> SEQUENCE: 43
gaggtccaac ttcagcagtc aggacctgaa ctggtgaaac ctggggcctc agtgaagatt     60
gcctgcaggg cctctggata cacattcact gcctacaata tccactgggt gagccagaga   120
catggaaaga gccttgaatg gattggatat atctatccta acaatggtgg ttctggctac   180
aaccagaaat tcatgaacaa ggccacattg actgtagacc attcctccaa tacagcctac   240
atggagctcc gcagcctgac gtctgaggac tctgcagtct attactgtgc aatatttgat   300
tacgacgagg cctggtttat ttactggggc caagggactc tggtcactgt ctctgca      357

<210> SEQ ID NO 44
<211> LENGTH: 321
<212> TYPE: DNA
<213> ORGANISM: Mus musculus

<400> SEQUENCE: 44
agtattgtga tgacccagac tcccaaattc ctgcttgtat cagcaggaga cagggttacc     60
ataacctgca aggccagtca gagtgtgagt aatgatgtag cttggtacca acagaagcca   120
gggcagtctc ctaaactgct gatatactat gcatccaatc gctacactgg agtccctgat   180
cgcttcactg gcagtggata tgggacggat ttcactttca ccatcagcgc tgtgcaggct   240
gaagacctgg cagtttattt ctgtcagcag gattatagct ctccgtacac gttcggaggg   300
gggaccaagc tggaaataaa a                                              321

<210> SEQ ID NO 45
<211> LENGTH: 351
<212> TYPE: DNA
<213> ORGANISM: Mus musculus

<400> SEQUENCE: 45
caggtccagc tgcagcagtc tggacctgaa ctggtgaagc ctgagacttc agtgaagata     60
tcctgcaagg cttctggcta caccttcaca agttactata tacactgggt gaaacagagg   120
cctggacagg gacttgagtg gattggctgg atttatcctg gaaatgttaa tactaagtat   180
aatgagaggt ttaagggcaa ggccactctg actgcagaca aatcctccaa cacagcccac   240
atgcagctca ccagcctgac ctctgaggac tctgcggtct atttctgtgc aagatcgaac   300
ccctatgtta tggactactg gggtcaagga acctcagtca ccgtctcctc a             351

<210> SEQ ID NO 46
<211> LENGTH: 321
<212> TYPE: DNA
<213> ORGANISM: Mus musculus

<400> SEQUENCE: 46
agtattgtga tgacccagac tcccaaattc ctgcttgtat cagcaggaga cagagtcacc     60
ataacctgca aggccagtca gagtgtgaat aatgatgtgg cttggtatca acagaagcca   120
gggctgtctc ctgaactgct tatgtattat gcatccaatc gcttcactgg agtccctgat   180
```

| | | | | |
|---|---|---|---|---|
| cgcttcactg | gcagtggata | tgggacggat | ttcactttca | ccatcagctc | tgtgcaggct | 240 |
| gaagacctgg | caatttattt | ctgtcagcag | gcttataggt | ctccgtacac | gttcggaggg | 300 |
| gggaccaagc | tggaaattca | a | | | | 321 |